(12) United States Patent
Ikeda et al.

(10) Patent No.: US 9,174,979 B2
(45) Date of Patent: *Nov. 3, 2015

(54) PHENANTHROINDOLIZIDINE COMPOUND AND NFκB INHIBITOR CONTAINING SAME AS ACTIVE INGREDIENT

(75) Inventors: Takashi Ikeda, Minato-ku (JP); Seigo Sawada, Minato-ku (JP); Takashi Yaegashi, Minato-ku (JP); Takeshi Matsuzaki, Minato-ku (JP); Shusuke Hashimoto, Minato-ku (JP); Ryuta Yamazaki, Minato-ku (JP)

(73) Assignee: KABUSHIKI KAISHA YAKULT HONSHA, Tokyo (JP)

( * ) Notice: Subject to any disclaimer, the term of this patent is extended or adjusted under 35 U.S.C. 154(b) by 279 days.

This patent is subject to a terminal disclaimer.

(21) Appl. No.: 13/125,698

(22) PCT Filed: Oct. 23, 2009

(86) PCT No.: PCT/JP2009/005594
§ 371 (c)(1),
(2), (4) Date: Apr. 22, 2011

(87) PCT Pub. No.: WO2010/047127
PCT Pub. Date: Apr. 29, 2010

(65) Prior Publication Data
US 2011/0201638 A1    Aug. 18, 2011

(30) Foreign Application Priority Data
Oct. 23, 2008  (JP) .................................. 2008-273610

(51) Int. Cl.
| | | |
|---|---|---|
| C07D 471/04 | (2006.01) | |
| A61K 31/437 | (2006.01) | |
| A61P 29/00 | (2006.01) | |
| A61P 35/00 | (2006.01) | |
| C07D 491/147 | (2006.01) | |

(52) U.S. Cl.
CPC .......... *C07D 471/04* (2013.01); *C07D 491/147* (2013.01)

(58) Field of Classification Search
None
See application file for complete search history.

(56) References Cited

U.S. PATENT DOCUMENTS

2005/0222418 A1* 10/2005 Baker et al. ................... 546/138
2006/0014772 A1    1/2006 Lee et al.

FOREIGN PATENT DOCUMENTS

| CN | 101189968 A | 6/2008 |
|---|---|---|
| CN | 101348483 A | 1/2009 |
| EP | 1 604 990 A1 | 12/2005 |
| JP | 2005-530691 | 10/2005 |
| WO | WO 01/23384 A1 | 4/2001 |
| WO | WO 2006/003676 A1 | 1/2006 |

OTHER PUBLICATIONS

Rao, K.V. Journal of Pharmaceutical Sciences, vol. 59, No. 11 (Nov. 1970), pp. 1608-1611.*
Golub et al. "Molecular Classification of Cancer: Class Discovery and Class Prediction by Gene Expression Monitoring." Science (1999), vol. 286, 531-537.*
Johnson et al. "Relationships between drug activity in NCI preclinical in vitro and in vivo models and early clinical trials." British Journal of Cancer (2001), 84(10), 1424-1431.*
Lala et al. "Role of nitric oxide in tumor progression: Lessons from experimental tumors." Cancer and Metastasis Reviews (1998), 17(1), 91-106.*
Sausville et al. "Contributions of Human Tumor Xenografts to Anticancer Drug Development." Cancer Res. 2006, 66(7), Apr. 1, 2006.*
International Search Report issued Dec. 22, 2009, in Patent Application No. PCT/JP2009/005594.
Wenli Gao, et al., "Structure-activity studies of phenanthroindolizidine alkaloids as potential antitumor agents", Bioorganic & Medicinal Chemistry Letters, vol. 17, No. 15, 2007, pp. 4338-4342.

(Continued)

*Primary Examiner* — Alicia L Otton
(74) *Attorney, Agent, or Firm* — Oblon, McClelland, Maier & Neustadt, L.L.P.

(57) ABSTRACT

A novel compound having an excellent NFκB inhibitory effect is provided and specifically disclosed is a compound represented by the following formula (1) or a salt thereof:
wherein, $R^1$ represents a hydrogen atom, a lower alkyl group, a lower alkyloxy group, or a halogen atom;
$R^2$ represents a hydroxyl group, or a lower alkyloxy group;
$R^3$ represents a hydrogen atom, a lower alkyl group, or a halogen atom;
$R^4$ represents a hydrogen atom or a lower alkyloxy group;
$R^5$ represents a hydrogen atom, a lower alkyloxy group, a halogen atom, a hydroxyl group, or a methylenedioxy group formed together with $R^6$ or an isopropylidenedioxy group formed together with $R^6$;
$R^6$ represents a hydrogen atom, a lower alkyloxy group, or a methylenedioxy group formed together with $R^5$ or an isopropylidenedioxy group formed together with $R^5$;
$R^7$ represents a hydrogen atom or a lower alkyl group; and
$R^8$ represents a hydrogen atom, a hydroxyl group, an amino group, or a lower alkylcarbonyloxy group (excluding the case where $R^1$, $R^3$, $R^4$ and $R^7$ are hydrogen atoms, $R^2$ and $R^8$ are hydroxyl groups, and $R^5$ and $R^6$ are methoxy groups).

(1)

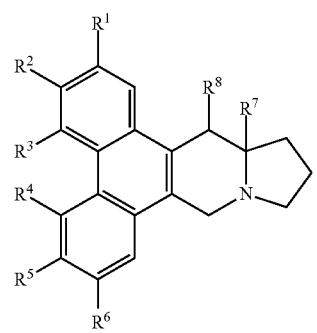

24 Claims, 2 Drawing Sheets

(56) References Cited

OTHER PUBLICATIONS

Ye Fu, et al., "Synthesis and structure-activity studies of antofine analogues as potential anticancer agents", Bioorganic & Medicinal Chemistry Letters, vol. 17, No. 1, 2007, pp. 97-100.

N. B. Mulchandani, et al., "Alkaloids of Pergularia Pallida", Phytochemistry, vol. 15, No. 10, 1976, pp. 1561-1563.

B. Chauncy, et al., "Synthesis of Phenanthroindolizidines: II. The Synthesis of (±;-Tylocrebrine, (±)-Antofine, and (±)-2,3-Dimethoxyphenanthroindolizidine", Australian Journal of Chemistry, vol. 23, No. 12, Dec. 1970, pp. 2503-2516.

Zaiguo Li, et al., "Isolation, Total Synthesis and Biological Activity of Phenanthroindolizidine and Phenanthroquinolizidine Alkaloids", Synthesis, No. 16, 2001, pp. 2365-2378.

Kosuke Takeuchi, et al., "Synthesis of 13a-methylphenanthroindolizidines using radical cascade cvclization: synthetic studies toward (±)-hypoestestatin 1", Tetrahedron, vol. 63, Issue 45, 2007, pp. 11101-11107.

K. K. Bhutani, et al., "Plant Based Antiamoebic Drugs; Part I. Antiamoebic Activity of Phenanthroindolizidine Alkaloids; Common Structural Determinants of Activity with Emetine", Planta Medica, vol. 53, Issue 6, 1987, pp. 532-536.

T. R. Govindachari, et al., "Chemical Examination of Tylophora Asthmatica-V[1]. Structure of Tylophorinine[2]", Tetrahedron, vol. 14, 1961, pp. 288-295.

Wenli Gao, et al., "Structural analogs of tylophora alkaloids may not be functional analogs", Bioorganic & Medicinal Chemistry Letters, vol. 18, No. 2, 2008, pp. 704-709.

Timothy S. Blackwell, et al., "The Role of Nuclear Factor-$_\kappa$B in Cytokine Gene Regulation", American Journal of Respiratory Cell and Molecular Biology, vol. 17, 1997, pp. 3-9.

Peter J. Barnes, et al., "Mechanisms of Disease", The New England Journal of Medicine, vol. 336, No. 15, Apr. 10, 1997, pp. 1066-1071.

Gary Nebel, et al., "An inducible transcription factor activates expression of human immunodeficiency virus in T cells", Letters to Nature, vol. 326, Apr. 16, 1987, pp. 711-713.

George Mosialos, "The role of Rel/NF-$_\kappa$B proteins in viral oncogenesis and the regulation of viral transcription", Seminars in Cancer Biology, vol. 8, 1997, pp. 121-129.

Béatrice Rayet, et al., "Aberrant *rel/nfkb* genes and activity in human cancer", Oncogene, vol. 18, 1999, pp. 6938-6947.

HJ Kim, et al., "NF-$_\kappa$B and IKK as therapeutic targets in cancer", Cell Death and Differentiation, vol. 13, 2006, pp. 738-474.

Ryuichi Morishita, et al., "In vivo transfection of *cis* element "decoy" against nuclear factor-$_\kappa$B binding site prevents myocardial infarction", Nature Medicine, vol. 3, No. 8, Aug. 1997, pp. 894-899.

C. Behl, et al., "Mechanism of amyloid β protein induced neuronal cell death: current concepts and future perspectives", Journal of Neural Transmission Supplementum, vol. 49, 1997, pp. 125-134.

Daniel G. Remick, "Applied Molecular Biology of Sepsis", Journal of Critical Care, vol. 10, No. 4, Dec. 1995, pp. 198-212.

Gabriele E. Sonnenberg, et al., "A Novel Pathway to the Manifestations of Metabolic Syndrome", Obesity Research, vol. 12, No. 2, Feb. 2004, pp. 180-186.

Emery Gellert, "Structure and Synthesis of Phenanthroindolizidine Alkaloids and Some Related Compounds", Alkaloids: Chemical and Biological Perspectives, vol. 5, 1987, pp. 55-132.

Beat Baumgartner, et al., "An Antimicrobial Alkaloid From *Ficus Septica*", Phytochemistry, vol. 29, No. 10, 1990, pp. 3327-3330.

Matthew Suffness, et al., "Miscellaneous Natural Products with Antitumor Activity", Anticancer Agents Based on Natural Product Models, 1980, pp. 465-487.

Wenli Gao, et al., "Novel Mode of Action of Tylophorine Analogs as Antitumor Compounds", Cancer Research, vol. 64, Jan. 15, 2004, pp. 678-688.

Hajime Komatsu, et al., "Phenanthroindolizidine Alkaloids as Cytotoxic Substances in a Danaid Butterfly, *Ideopsis similis*, against Human Cancer Cells", Journal of Medicinal Chemistry, vol. 44, No. 11, 2001, pp. 1833-1836.

U.S. Appl. No. 13/124,554, filed Apr. 15, 2011, Ikeda, et al.

Office Action issued on Dec. 12, 2012 in the corresponding Chinese Patent Application No. 200980141088.6 (with English Translation).

Office Action issued Feb. 18, 2014 in corresponding Japanese Patent Application No. 2010-534720 with English translation, 9 pp.

Kinuko Iwasa, et al., "The Preparation of the Biosynthetic Precursor 3,7-Dihydroxy-2,6-Dimethoxyphenanthroindolizidine", Journal of Natural Products, 1988, 51(1), pp. 172-175.

\* cited by examiner

PHENANTHROINDOLIZIDINE COMPOUND AND NFκB INHIBITOR CONTAINING SAME AS ACTIVE INGREDIENT

TECHNICAL FIELD

The present invention relates to a Nuclear Factor-κB (hereinafter, may be referred to as NFκB) inhibitor. In more detail, the present invention relates to a novel phenanthroindolizidine alkaloid compound or a salt thereof inhibiting NFκB, and a medicine containing the same.

BACKGROUND ART

NFκB exists as a dimer formed by various combinations of p50, p65/RelA, c-Rel, Rel-B, and p52, all of which are members of the NFκB family. Among them, the most well-known dimer is a heterodimer composed of a 50 kDa subunit (p50) and a 65 kDa subunit (p65).

Usually, this heterodimer is present in an inactive state in cytoplasmas through binding to an inhibitor of NFκB (IκB). However, once the cells are stimulated by inflammatory cytokines, cell growth factors, and the like, IκB kinase is activated via the AKT signal transduction pathway and the like, leading to phosphorylation of IκB. The phosphorylated IκB is ubiquitinated and then decomposed by proteasome. As a result, NFκB is detached from IκB and migrate into the nucleus, where it binds to the NFκB responsive element to activate transcription of various target genes.

The target genes include many genes associated with inflammation and immune response (Non Patent Document 1), and the activation of NFκB is known to be associated with diseases such as rheumatoid arthritis, osteoarthritis, inflammatory bowel disease, atopic dermatitis, and asthma (Non Patent Document 2).

Also, various viruses such as HIV are known to activate NFκB in host cells, from which NFκB is considered to contribute to viral infection (Non Patent Documents 3 and 4).

Furthermore, recently, NFκB is known to be often constitutively activated in various tumor, and thus it is considered that NFκB may possibly be involved also in the induction of expression of various genes associated with the progression of cancer, such as carcinogenesis, metastasis, anti-apoptosis, and cell proliferation, and the resistance against anti cancer agent therapy (Non Patent Documents 5 and 6).

Further, NFκB is also known to be associated with diseases such as ischemic heart disease (Non Patent Document 7), Alzheimer's disease (Non Patent Document 8), ichorrhemia (Non Patent Document 9), and metabolic syndrome (Non Patent Document 10).

Accordingly, a compound inhibiting NFκB is useful as a preventive or therapeutic agent for chronic inflammatory disease, autoimmune disease, viral disease, immune disease, novel cancer therapy, and other diseases attributable to the activation of NFκB, and such a compound is actively developed.

Meanwhile, tylophorine represented by the following formula (A) and an analog thereof are called phenanthroindolizidine alkaloid, which is a compound mainly obtained from a plant belonging to the family Asclepiadaceae (the genera *Tylophora*, *Vincetoxicum*, *Pergularia*, and *Cynanchum*) (Non Patent Document 11).

Also, some of the aforementioned plants belonging to the genus *Tylophora* are known as raw materials for anti-inflammatory drugs, antiasthma drugs, and antiameba drugs (Non Patent Document 12). Also, tylophorine is known to exhibit a potent cytotoxic activity, and a research on the synthetic method thereof is also vigorously conducted (Non Patent Document 13). Further, among the above-noted phenanthroindolizidine alkaloid, tylocrebrine represented by the following formula (B) is known to have neurotoxicity (Non Patent Document 14). Also, recently, it is known that tylophorine analogs represented by the following formulas (C) and (D) have consistently exhibited a potent cytotoxic activity in the NCI-60 tumor cell panel study, and that the mechanism of action of those tylophorine analogs is different from that of existing antitumor agents (Non Patent Document 15). Further, a compound represented by the following formula (E), which is phenanthroindolizidine alkaloid derived from the insect, is known to have a potent cytotoxic activity (Non Patent Document 16).

Furthermore, phenanthroindolizidine alkaloid is known to inhibit transcription mediated by NFκB, which is a transcription factor (Non Patent Document 15).

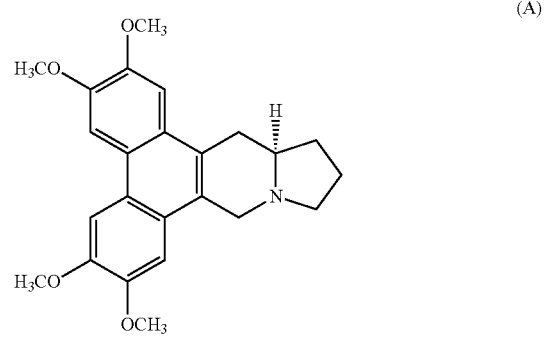

(A)

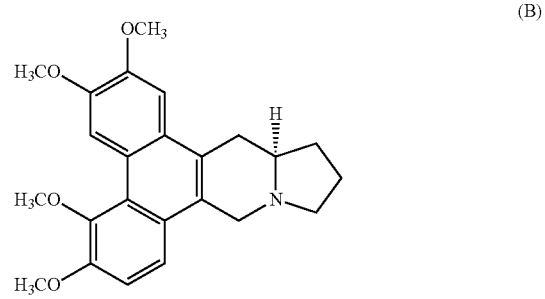

(B)

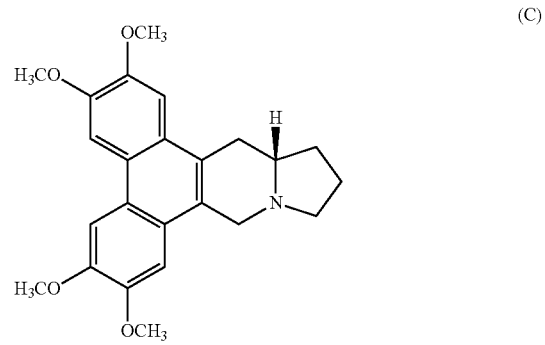

(C)

-continued

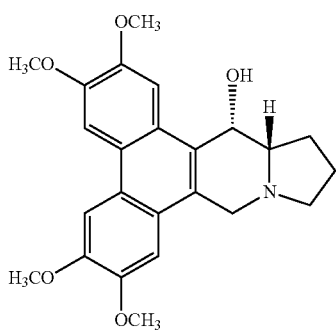

(D)

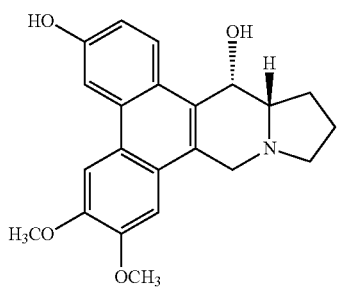

(E)

PRIOR ART DOCUMENT

Non Patent Document

[Non Patent Document 1] Am. J. Respir. Cell Mol. Biol. 1997, 17, 3-9
[Non Patent Document 2] N. Engl. J. Med. 1997, 336, 1066-1071
[Non Patent Document 3] Nature 1987, 326, 711-713
[Non Patent Document 4] Semin. Cancer Biol. 1997, 8, 121-129
[Non Patent Document 5] Oncogene 1999, 18, 6938-6947
[Non Patent Document 6] Cell Death Differ. 2006, 13, 738-747
[Non Patent Document 7] Nat. Med. 1997, 3, 894-899
[Non Patent Document 8] J. Neural Transm. Suppl. 1997, 49, 125-134
[Non Patent Document 9] J Crit Care. 1995, 10, 198-212
[Non Patent Document 10] Obes Res. 2004, 12, 180-186.
[Non Patent Document 11] The Alkaloids, Chemistry and Biological Perspectives 1987, pp 55-132
[Non Patent Document 12] Phytochemisty 1990, 3327-3330
[Non Patent Document 13] Synthesis 2001, 2365-2378
[Non Patent Document 14] Anticancer Agents Based on Natural Product Models 1980, pp 465-487
[Non Patent Document 15] Cancer Research 2004, 678-688
[Non Patent Document 16] J. Med. Chem. 2001, 1833-1836
[Non Patent Document 17] Bioorg. Med. Chem. Lett. 2007, 4338-4342

SUMMARY OF THE INVENTION

Problem to be Solved by the Invention

Accordingly, it is an object of the present invention to provide a novel compound having an excellent NFκB inhibitory action.

Means of Solving the Problem

Despite the fact that phenanthroindolizidine alkaloid has a potent cytotoxic activity and an interesting mechanism of action as described above, there are very few reports on the systemic and comprehensive assessment of the biological activity, particularly the assessment of the in vivo antitumor activity, of such alkaloid (Non Patent Documents 15 and 17).

Under such a circumstance, the present inventors conducted an intensive research to achieve the aforementioned object. As a result, they have found that a compound represented by the following formula (1) or a salt thereof have excellent NFκB inhibitory action, antitumor action, and anti-inflammatory action, while having few side effects and excellent solubility, and thus is useful as a medicine such as an anticancer agent, whereby completing the present invention.

That is, the present invention provides a compound represented by the following formula (1) or a salt thereof:

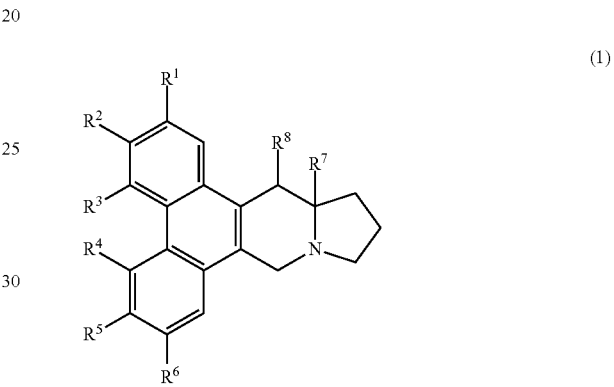

(1)

wherein, $R^1$ represents a hydrogen atom, a lower alkyl group, a lower alkyloxy group, or a halogen atom;
$R^2$ represents a hydroxyl group, or a lower alkyloxy group;
$R^3$ represents a hydrogen atom, a lower alkyl group, or a halogen atom;
$R^4$ represents a hydrogen atom or a lower alkyloxy group;
$R^5$ represents a hydrogen atom, a lower alkyloxy group, a halogen atom, a hydroxyl group, or a methylenedioxy group formed together with $R^6$ or an isopropylidenedioxy group formed together with $R^6$;
$R^6$ represents a hydrogen atom, a lower alkyloxy group, or a methylenedioxy group formed together with $R^5$ or an isopropylidenedioxy group formed together with $R^5$;
$R^7$ represents a hydrogen atom or a lower alkyl group; and
$R^8$ represents a hydrogen atom, a hydroxyl group, an amino group, or a lower alkylcarbonyloxy group;
provided that the following cases are excluded: the case where $R^1$, $R^3$, $R^4$, and $R^7$ are hydrogen atoms; $R^2$ and $R^8$ are hydroxyl groups and $R^5$ and $R^6$ are methoxy groups; the case where $R^1$, $R^3$, $R^4$, and $R^7$ are hydrogen atoms, $R^2$, $R^5$, and $R^6$ are methoxy groups, and $R^8$ is a hydroxyl group; the case where $R^1$, $R^3$, $R^4$, $R^7$, and $R^8$ are hydrogen atoms and $R^2$, $R^5$, and $R^6$ are methoxy groups; the case where $R^1$, $R^3$, $R^4$, and $R^7$ are hydrogen atoms, $R^2$, $R^5$, and $R^8$ are hydroxyl groups, and $R^6$ is a methoxy group; the case where $R^1$, $R^3$, $R^4$, and $R^7$ are hydrogen atoms, $R^2$ and $R^6$ are methoxy groups, and $R^5$ and $R^8$ are hydroxyl groups; the case where $R^1$, $R^3$, $R^4$, $R^7$, and $R^8$ are hydrogen atoms, $R^2$ and $R^6$ are methoxy groups, and $R^5$ is a hydroxyl group; the case where $R^1$, $R^2$, $R^5$, and $R^6$ are methoxy groups and $R^3$, $R^4$, $R^7$, and $R^8$ are hydrogen atoms; the case where $R^1$, $R^2$, $R^4$, and $R^5$ are methoxy groups and $R^3$, $R^6$, $R^7$, and $R^8$ are hydrogen atoms; the case where $R^1$, $R^2$, $R^5$, and $R^6$ are methoxy groups, $R^3$, $R^4$, and $R^7$ are hydrogen atoms, and $R^8$ is a hydroxyl group; the case where $R^1$ and $R^2$ are methoxy groups, $R^3$, $R^4$, $R^6$, $R^7$, and $R^8$ are hydrogen atoms, and $R^5$ is a hydroxyl group; the case where $R^1$, $R^2$, and $R^5$ are methoxy groups, and $R^3$, $R^4$, $R^6$, $R^7$, and $R^8$ are hydrogen atoms; the case where $R^1$, $R^2$, and $R^5$ are methoxy groups, $R^3$, $R^4$, $R^6$, and $R^7$ are hydrogen atoms, and $R^8$ is a hydroxyl group; the case where $R^1$, $R^2$, and $R^5$ are methoxy groups, $R^3$, $R^4$, $R^6$, and $R^8$ are hydrogen atoms, and $R^7$ is a methyl group; the case where $R^1$, $R^2$, and $R^5$ are methoxy groups, $R^3$, $R^4$, and $R^6$ are hydrogen atoms, $R^7$ is a methyl group, and $R^8$ is a hydroxyl group; the case where $R^1$, $R^2$, and $R^6$ are methoxy groups, $R^3$, $R^4$, $R^7$, and $R^8$ are hydrogen atoms, and $R^5$ is a hydroxyl group; and the case where $R^1$, $R^2$, and $R^4$ are methoxy groups, $R^3$, $R^6$, $R^7$, and $R^8$ are hydrogen atoms, and $R^5$ is a hydroxyl group.

The present invention also provides a medicine containing a compound represented by the above formula (1) or a salt thereof as an active ingredient.

The present invention also provides a pharmaceutical composition containing a compound represented by the above formula (1) or a salt thereof and a pharmaceutically acceptable carrier.

The present invention further provides use of a compound represented by the above formula (1) or a salt thereof for the production of a medicine.

The present invention further provides a method for preventing or treating diseases associated with accelerated NFκB activity, cancer or inflammatory disease characterized by administering a compound represented by the above formula (1) or a salt thereof.

Effects of the Invention

The compound represented by the formula (1) or the salt thereof of the present invention has excellent NFκB inhibitory action, antitumor action, and anti-inflammatory action, while having few side effects and excellent solubility, thus it is useful as a medicine, an NFκB inhibitor, a preventive or therapeutic agent for diseases associated with accelerated NFκB activity including anticancer agents (proliferation or metastasis of cancer), resistance against anticancer agents, inflammatory disease (rheumatoid arthritis, osteoarthritis, atopic dermatitis, bronchial asthma, psoriasis, inflammatory bowel disease, and the like), cardiovascular disease (ischemic disease, vascular restenosis after percutaneous transluminal coronary angioplasty (PTCA), and the like), pulmonary fibrosis, diabetes, autoimmune disease, viral disease, Alzheimer's disease, ichorrhemia, metabolic syndrome, and the like. More specifically, the compound of the present invention represented by the formula (1) or the salt thereof is useful as an anticancer agent and a preventive or therapeutic agent for various inflammatory diseases.

MODE FOR CARRYING OUT THE INVENTION

Figure 1:
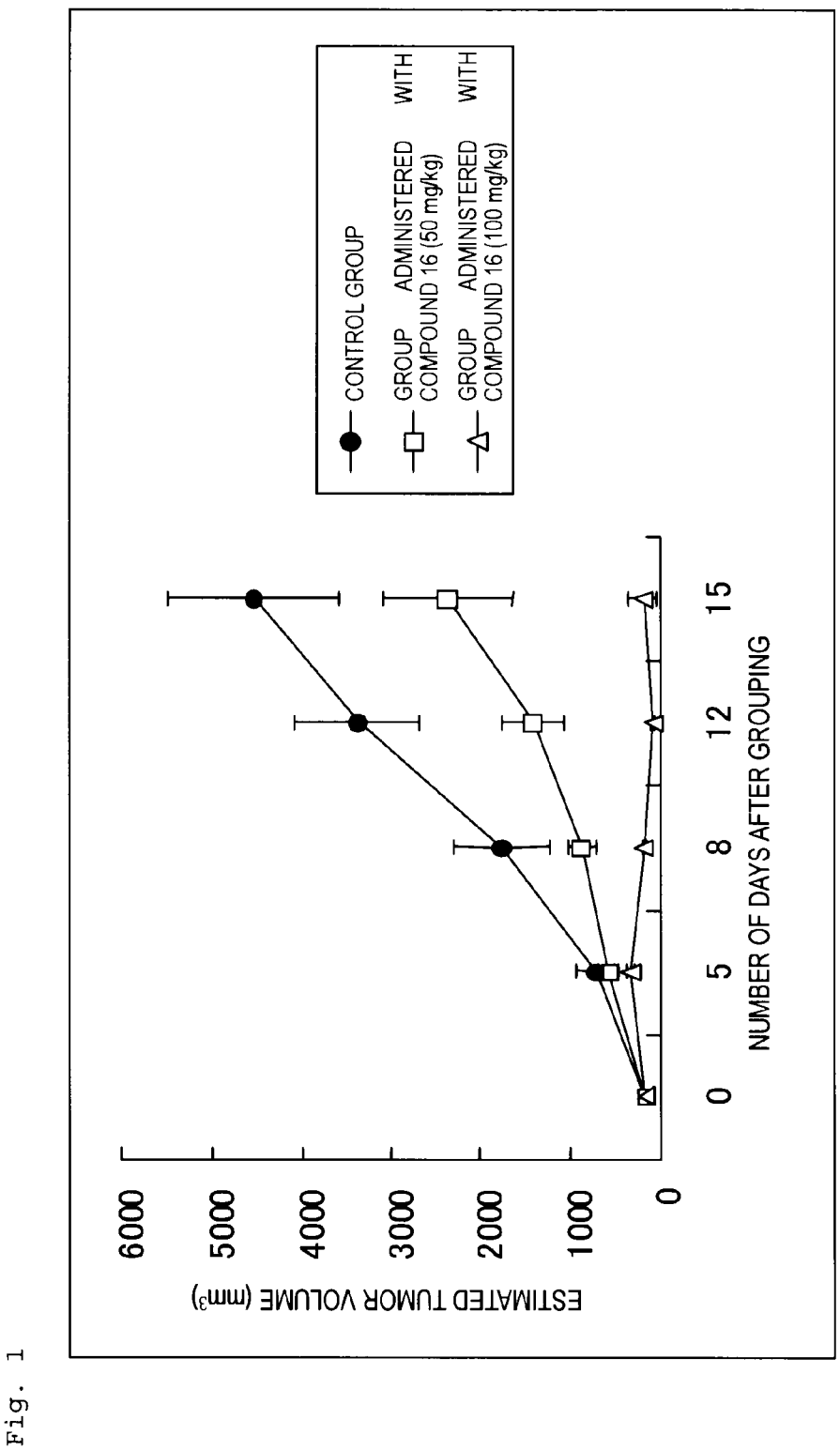
FIG. 1 is a graph showing the antitumor effect of the compound of the present invention in mice transplanted with human promyelocytic leukemia HL-60 cells.

In the general formula (1), examples of $R^1$ include a hydrogen atom, a lower alkyl group, a lower alkyloxy group, and a halogen atom, of which a hydrogen atom, or the following functional groups are particularly preferable.

Examples of the lower alkyl group include an alkyl group with a carbon number of 1 to 6. Specific examples thereof include a methyl group, an ethyl group, a propyl group, a butyl group, a pentyl group, and a hexyl group. Among these, a methyl group is particularly preferable.

Examples of the lower alkyloxy group include an alkyloxy group with a carbon number of 1 to 6. Specific examples thereof include a methoxy group, an ethoxy group, a propoxy group, a butoxy group, a pentyloxy group, and a hexyloxy group. Among these, a methoxy group is particularly preferable.

Also, examples of the halogen atom include a chlorine atom, a bromine atom, a fluorine atom, and an iodine atom. Among these, a chlorine atom and a fluorine atom are particularly preferable.

That is, in the general formula (1), as $R^1$, a hydrogen atom, a methyl group, a methoxy group, a chlorine atom, or a fluorine atom is particularly preferable.

In the general formula (1), examples of $R^2$ include a hydroxyl group and a lower alkyloxy group. Among these, a hydroxyl group or the following functional groups are particularly preferable.

Examples of the lower alkyloxy group include an alkyloxy group with a carbon number of 1 to 6. Specific examples thereof include a methoxy group, an ethoxyl group, a propoxy group, a butoxy group, a pentyloxy group, and a hexyloxy group. Among these, a methoxy group is particularly preferable.

That is, in the general formula (1), as $R^2$, a hydroxyl group or a methoxy group is particularly preferable.

In the general formula (1), examples of $R^3$ include a hydrogen atom, a lower alkyl group, and a halogen atom. Among these, a hydrogen atom or the following functional groups are particularly preferable.

Examples of the lower alkyl group include an alkyl group with a carbon number of 1 to 6. Specific examples thereof include a methyl group, an ethyl group, a propyl group, a butyl group, a pentyl group, and a hexyl group. Among these, a methyl group is particularly preferable.

Also, examples of the halogen atom include a chlorine atom, a bromine atom, a fluorine atom, and an iodine atom. Among these, a chlorine atom or a fluorine atom is particularly preferable.

That is, in the general formula (1), as $R^3$, a hydrogen atom, a methyl group, a chlorine atom, or a fluorine atom is particularly preferable.

In the general formula (1), examples of $R^4$ include a hydrogen atom and a lower alkyloxy group. Among these, a hydrogen atom or the following functional groups are particularly preferable.

Examples of the lower alkyloxy group include an alkyloxy group with a carbon number of 1 to 6. Specific examples thereof include a methoxy group, an ethoxyl group, a propoxy group, a butoxy group, a pentyloxy group, and a hexyloxy group. Among these, a methoxy group is particularly preferable.

That is, in the general formula (1), as $R^4$, a hydrogen atom or a methoxy group is particularly preferable.

In the general formula (1), examples of $R^5$ include a hydrogen atom, a lower alkyloxy group, a halogen atom, a hydroxyl group, a methylenedioxy group formed together with $R^6$, and an isopropylidenedioxy group formed together with $R^6$. Among these, a hydrogen atom, a hydroxyl group, a methylenedioxy group formed together with $R^6$, and an isopropylidenedioxy group formed together with $R^6$, or the following functional groups are particularly preferable.

Examples of the lower alkyloxy group include an alkyloxy group with a carbon number of 1 to 6. Specific examples thereof include a methoxy group, an ethoxyl group, a propoxy group, a butoxy group, a pentyloxy group, and a hexyloxy group, and among these, a methoxy group and an ethoxy group are particularly preferable.

Also, examples of the halogen atom include a chlorine atom, a bromine atom, a fluorine atom, and an iodine atom, and among these, a fluorine atom is particularly preferable.

That is, in the general formula (1), as $R^5$, a hydrogen atom, a methoxy group, an ethoxy group, a fluorine atom, a hydroxyl group, a methylenedioxy group formed together with $R^6$, or an isopropylidenedioxy group formed together with $R^6$ is particularly preferable.

In the general formula (1), examples of $R^6$ include a hydrogen atom, a lower alkyloxy group, a methylenedioxy group formed together with $R^5$, or an isopropylidenedioxy group formed together with $R^5$. Among these, a hydrogen atom, a methylenedioxy group formed together with $R^5$, an isopropylidenedioxy group formed together with $R^5$, or the following functional groups are particularly preferable.

Examples of the lower alkyloxy group include an alkyloxy group with a carbon number of 1 to 6. Specific examples thereof include a methoxy group, an ethoxy group, a propoxy group, a butoxy group, a pentyloxy group, and a hexyloxy group, and among these, a methoxy group and an ethoxy group are particularly preferable.

That is, in the general formula (1), as $R^6$, a hydrogen atom, a methoxy group, an ethoxy group, a methylenedioxy group formed together with $R^5$, or an isopropylidenedioxy group formed together with $R^5$ is particularly preferable.

In the general formula (1), examples of $R^7$ include a hydrogen atom and a lower alkyl group, and among these, a hydrogen atom or the following functional groups are particularly preferable.

Examples of the lower alkyl group include an alkyl group with a carbon number of 1 to 6. Specific examples thereof include a methyl group, an ethyl group, a propyl group, a butyl group, a pentyl group, and a hexyl group, and among these, a methyl group is particularly preferable.

That is, in the general formula (1), as $R^7$, a hydrogen atom or a methyl group is particularly preferable.

In the general formula (1), examples of $R^8$ include a hydrogen atom, a hydroxyl group, an amino group, and a lower alkylcarbonyloxy group. Particularly, a hydrogen atom, a hydroxyl group, an amino group, or the following functional groups are particularly preferable.

Examples of the lower alkylcarbonyloxy group include an alkylcarbonyloxy group with a carbon number of 1 to 6. Specific examples thereof include an acetoxy group, a propionyloxy group, and a butyryloxy group, and among these, an acetoxy group is particularly preferable.

That is, in the general formula (1), as $R^8$, a hydrogen atom, a hydroxyl group, an amino group, or an acetoxy group is particularly preferable.

A compound of the general formula (1), wherein $R^1$ is a hydrogen atom; $R^2$ is a hydroxyl group; $R^3$ is a hydrogen atom; $R^4$ is a hydrogen atom; $R^5$ is a methoxy group; $R^6$ is a methoxy group; $R^7$ is a hydrogen atom; and $R^8$ is a hydrogen atom, is more preferable.

In the present invention, the compound of the above formula (1) has two stereocenters (carbon atoms at which $R^7$ and $R^8$ are substituted). Because these stereocenters could take either an R configuration or an S configuration, four kinds of stereoisomers are possible. However, all of such stereoisomers and a mixture of various combinations of stereoisomers are encompassed by the scope of the present invention.

Examples of the isomer include (a configuration in which $R^7$=S, $R^8$=S), (a configuration in which $R^7$=R, $R^8$=R), (a configuration in which $R^7$=S, $R^8$=R), and (a configuration in which $R^7$=R, $R^8$=S). Among these, (a configuration in which $R^7$=S, $R^8$=S) is particularly preferable since a compound having such a configuration strongly inhibits NFκB without inducing unfavorable side effects.

In the present invention, a compound of the following formula (2) or a pharmaceutically acceptable salt thereof is more preferable since such a compound or salt strongly inhibits NFκB without inducing unfavorable side effects.

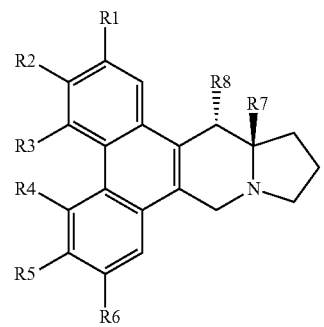

(2)

wherein, $R^1$, $R^2$, $R^3$, $R^4$, $R^5$, $R^6$, $R^7$, and $R^8$ are the same as above.

When the compound represented by the formula (1) has a conformation represented by the formula (2), the compound preferably has a hydrogen atom at $R^8$ since such a compound strongly inhibits NFκB without inducing unfavorable side effects.

In the present invention, specific examples of a particularly preferable compound or a salt thereof include one selected from the group consisting of (12aS,13S)-5,6,7-trimethoxy-9,10,11,12,12a,13-hexahydro-9a-aza-cyclopenta[b]triphenylene-3,13-diol;

(12aR,13R)-5,6,7-trimethoxy-9,10,11,12,12a,13-hexahydro-9a-aza-cyclopenta[b]triphenylene-3,13-diol;

(12aS,13S)-9,10,11,12,12a,13-hexahydro-9a-aza-cyclopenta[b]triphenylene-3,13-diol;

(12aS,13S)-6-fluoro-9,10,11,12,12a,13-hexahydro-9a-aza-cyclopenta[b]triphenylene-3,13-diol;

acetic acid(12aS,13S)-3-hydroxy-6,7-dimethoxy-9,10,11,12,12a,13-hexahydro-9a-aza-cyclopenta[b]triphenylene-13-yl ester;

6,7-dimethoxy-12a-methyl-9,10,11,12,12a,13-hexahydro-9a-aza-cyclopenta[b]triphenylene-3,13-diol;

(S)-13-amino-6,7-dimethoxy-9,10,11,12,12a,13-hexahydro-9a-aza-cyclopenta[b]triphenylene-3-ol;

(12aS,13S)-6,7-methylenedioxy-9,10,11,12,12a,13-hexahydro-9a-aza-cyclopenta[b]triphenylene-3,13-diol;

(12aS,13S)-6,7-isopropylidenedioxy-9,10,11,12,12a,13-hexahydro-9a-aza-cyclopenta[b]triphenylene-3,13-diol;

(12aS,13S)-6,7-diethoxy-9,10,11,12,12a,13-hexahydro-9a-aza-cyclopenta[b]triphenylene-3,13-diol;

(S)-6,7-dimethoxy-9,10,11,12,12a,13-hexahydro-9a-aza-cyclopenta[b]triphenylene-3-ol;

(R)-6,7-dimethoxy-9,10,11,12,12a,13-hexahydro-9a-aza-cyclopenta[b]triphenylene-3-ol;

(S)-6,7-methylenedioxy-9,10,11,12,12a,13-hexahydro-9a-aza-cyclopenta[b]triphenylene-3-ol;

(S)-6,7-diethoxy-9,10,11,12,12a,13-hexahydro-9a-aza-cyclopenta[b]triphenylene-3-ol;

(12aS,13S)-2,3-dimethoxy-9,10,11,12,12a,13-hexahydro-9a-aza-cyclopenta[b]triphenylene-6,13-diol;

(S)-2-chloro-6,7-dimethoxy-9,10,11,12,12a,13-hexahydro-9a-aza-cyclopenta[b]triphenylene-3-ol;

(S)-4-chloro-6,7-dimethoxy-9,10,11,12,12a,13-hexahydro-9a-aza-cyclopenta[b]triphenylene-3-ol;

(S)-2,4-dichloro-6,7-dimethoxy-9,10,11,12,12a,13-hexahydro-9a-aza-cyclopenta[b]triphenylene-3-ol;

(S)-4-fluoro-6,7-dimethoxy-9,10,11,12,12a,13-hexahydro-9a-aza-cyclopenta[b]triphenylene-3-ol;

(S)-2-fluoro-6,7-dimethoxy-9,10,11,12,12a,13-hexahydro-9a-aza-cyclopenta[b]triphenylene-3-ol; and (S)-6,7-dimethoxy-2,4-dimethyl-9,10,11,12,12a,13-hexahydro-9a-aza-cyclopenta[b]triphenylene-3-ol.

In the present invention, a salt of a compound represented by the general formulas (1) or (2) may be a pharmaceutically acceptable salt. Examples thereof include an inorganic acid salt such as hydrochloride, sulfate, phosphate, hydrobromide, hydroiodide, nitrate, pyrosulfate, and metaphosphate; an organic acid salt such as citrate, oxalate, benzoate, acetate, trifluoroacetate, propionate, succinate, fumarate, lactate, maleate, tartrate, glutarate, citrate, sulfonate (for example, methanesulfonate, p-toluenesulfonate, and naphthalenesulfonate); and a metal salt such as a lithium salt, a sodium salt, a potassium salt, a magnesium salt, and a calcium salt.

The compound of the present invention can be produced, for example, in accordance with the following reaction formula (a compound in which $R^7$=H, $R^8$=OH (compound j) and a compound in which $R^7$=$R^8$=H (compound 1) in the general formula (1) or (2) will be shown as examples).

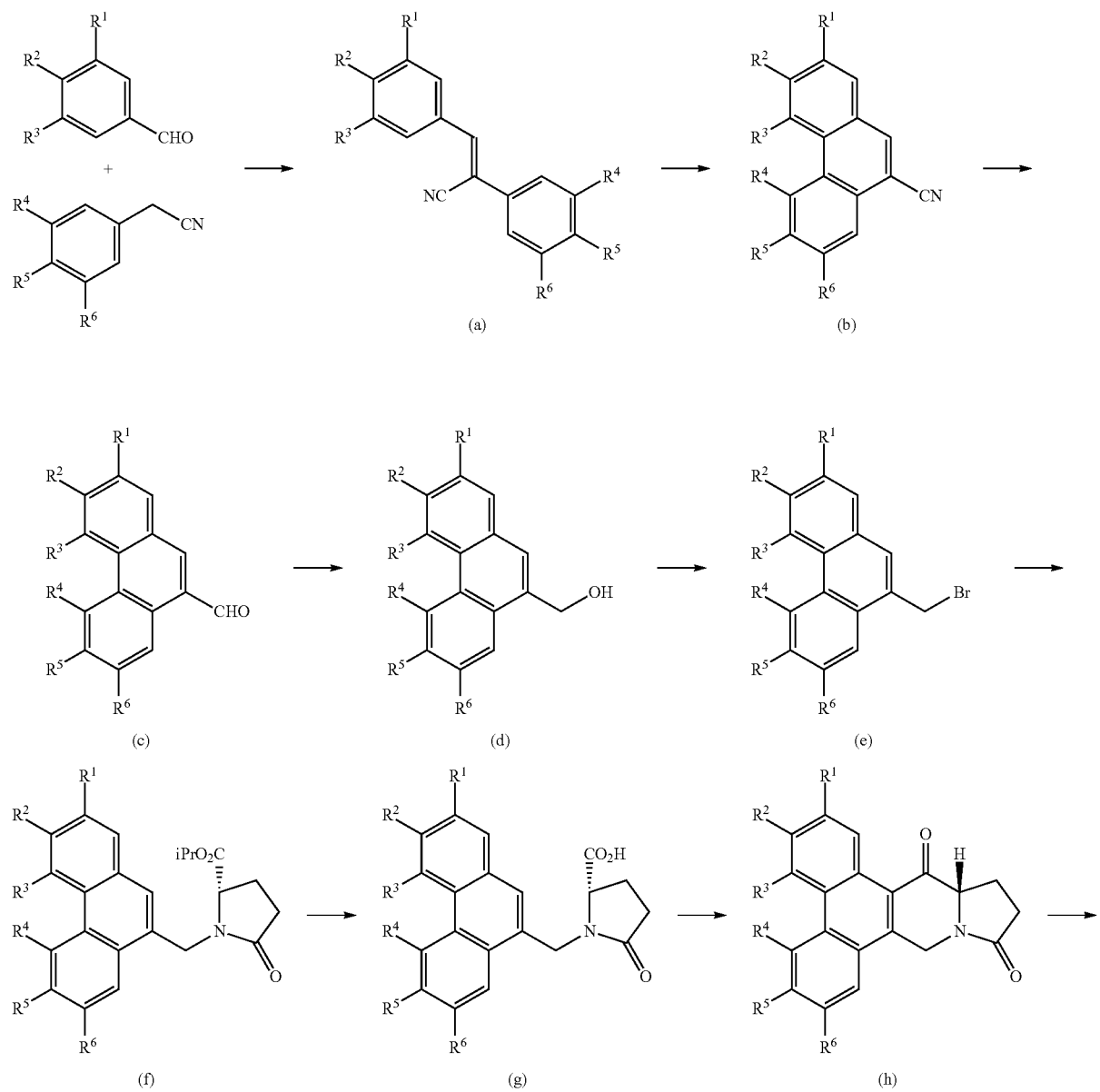

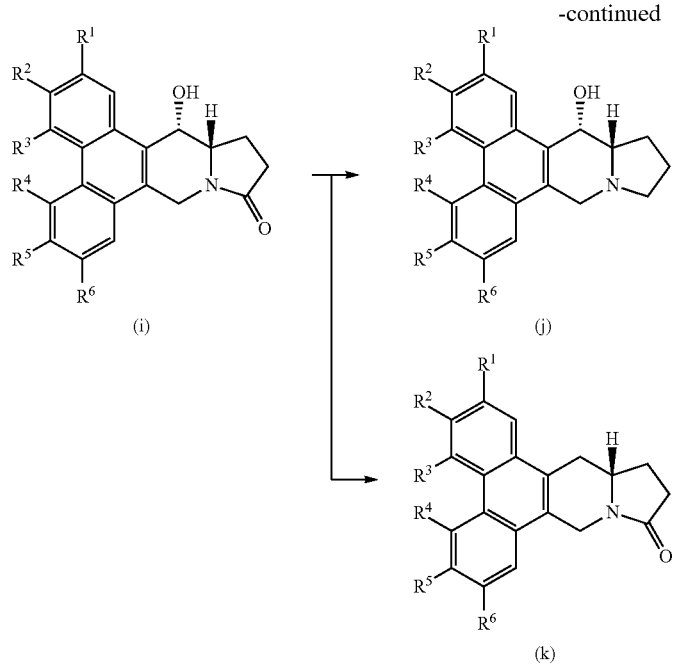

(i)

(j)

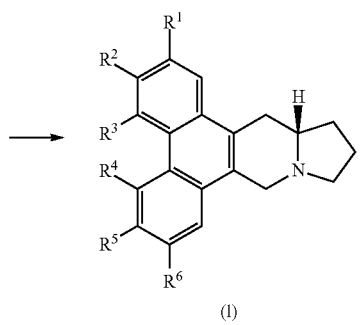

(k)

(l)

wherein, the groups $R^1$ to $R^6$ represent the same groups as mentioned above, or if there is a functional group involved in the reaction, such a group may be appropriately protected.

That is, benzaldehyde was reacted with benzyl cyanide to give a compound (a), which was cyclized to give a compound (b). Subsequently, a cyano group was reduced, whereby aldehyde (c) was obtained. After that, a carbonyl group was reduced to give alcohol (d), which was brominated to give (e), and then, the (e) was reacted with glutamic acid ester, followed by cyclization, whereby (f) was obtained. The (f) was hydrolyzed to give (g), from which (h) was obtained through intramolecular acylation. After that, a carbonyl group was reduced to give (i), followed by reduction of lactam, whereby phenanthroindolizidine (j) having a hydroxyl group at $R^8$ was obtained. The hydroxyl group at $R^8$ of the compound (i) was reductively removed to give (k), followed by reduction of lactam, whereby phenanthroindolizidine (l) having a hydrogen atom at $R^8$ was obtained.

The reaction of benzaldehyde with benzyl cyanide is preferably carried out in alcohol in the presence of a base. At this point, specific examples of the base include sodium methoxide and sodium ethoxide.

The cyclization of the compound (a) is preferably carried out by photoirradiation in the presence of iodine and propylene oxide. Also, a cyclization reaction involving treatment with vanadium (V) or thallium (III) may be employed.

The reduction of the compound (b) is preferably carried out by reacting diisobutylaluminum hydride. Also, the reduction of the compound (c) is preferably carried out by reacting sodium borohydride.

The bromination of the compound (d) is preferably carried out by reacting phosphorous tribromide in the presence of triethylamine. Also, the bromination may be carried out by allowing carbon tetrabromide to act in the presence of triphenylphosphine.

The amination-lactamization of the compound (e) with L-glutamic acid diisopropyl ester is preferably carried out in a solvent such as dimethylformamide in the presence of a base such as potassium carbonate, and allowing an acid such as acetic acid to act on the resulting aminated product in alcohol such as methanol. At this point, when D-glutamic acid diisopropyl ester is used, a corresponding enantiomer is obtained.

The hydrolysis of the compound (f) is preferably carried out using a base in a solvent such as methanol. At this point, specific examples of the base include potassium hydroxide and sodium hydroxide.

The intramolecular Friedel-Crafts reaction of the compound (g) is preferably carried out in a solvent such as methylene chloride by converting the compound (g) to acid chloride by oxalyl chloride within a system, followed by treatment with a Lewis acid. At this point, specific examples of the Lewis acid include tin chloride and aluminum chloride.

The reduction of the compound (h) is preferably carried out using a reducing agent such as sodium borohydride and lithium tri-secondary butyl borohydride. For stereoselective reduction, the reduction is preferably carried out using a reducing agent such as lithium tri-secondary butyl borohydride.

The reduction of the lactam of the compound (i) is preferably carried out using a reducing agent such as borane and lithium aluminum hydride.

The reduction of the hydroxyl group of the compound (i) is preferably carried out by a combination of an acid and a reducing agent. As the acid, trifluoroacetic acid, a boron trifluoride-diethyl ether complex, and the like are preferable. As the reducing agent, triethylsilane is preferable.

The reduction of the lactam of the compound (k) is preferably carried out using a reducing agent such as borane and lithium aluminum hydride.

As will be shown in the following Examples, a compound represented by the formula (1) or a salt thereof have excellent NFκB inhibitory action, antitumor action and anti-inflammatory action.

Accordingly, the compound or the salt thereof of the present invention is useful as a medicine, an NFκB inhibitor, an anticancer agent (proliferation or metastasis of cancer), and a preventive or therapeutic agent for diseases associated with accelerated NFκB activity including resistance against anticancer agents, inflammatory disease (rheumatoid arthritis, osteoarthritis, atopic dermatitis, bronchial asthma, psoriasis, inflammatory bowel disease, and the like), cardiovascular disease (ischemic disease, vascular restenosis after percutaneous transluminal coronary angioplasty (PTCA), and the like), pulmonary fibrosis, diabetes, autoimmune disease, viral disease, Alzheimer's disease, ichorrhemia, metabolic syndrome, and the like.

In the present invention, no particular limitation is imposed on the "NFκB inhibitor" as long as it has an inhibitory action on NFκB. More specifically, an NFκB inhibitor exhibits an $IC_{50}$ value of the inhibitory action on NFκB of preferably 2000 ng/mL or less, more preferably 500 ng/mL or less, and particular preferably 100 ng/mL or less, as measured by the method of Example 2 described below.

Also, an NFκB inhibitor exhibits an $IC_{50}$ value of the inhibitory action on cancer proliferation of preferably 2000 ng/mL or less, more preferably 500 ng/mL or less, and particular preferably 100 ng/mL or less, as measured by the method of Example 3 described below.

When a compound represented by the formula (1) or a salt thereof is used as a medicine, one kind of the compound or the salt thereof may be used alone or plural kinds thereof may be used in combination. Further, a compound represented by the formula (1) or a salt thereof may also be used in combination with other therapeutically advantageous compounds, and the mechanism of action of these therapeutically advantageous compounds may be the same as or different from that of the compound of the present invention.

When the compound of the present invention is used as a medicine, it can be administered in any dosage form. Examples thereof include an orally administered agent such as a tablet, a capsule, a granule, a sugar-coated tablet, a pill, a fine granule, powder, a dust formulation, a sustained-release formulation, a suspension, an emulsion, syrup, an emulsified formulation, a lyophilized preparation, a liquid, and an elixir; and a parenterally administered agent including an injection such as an intravenous injection, an intramuscular injection, a subcutaneous injection, or a drip infusion, an external agent such as an endermic liniment or a patch, a suppository, an infusion solution, a percutaneous agent, a transmucosal agent, a nasal agent, an inhalant, a bolus, and the like.

When the compound is used as a medicine, a preparation can be produced by an ordinary method, in which the compound represented by the formula (1) or the salt thereof of the present invention may be employed alone or in combination with a pharmaceutically acceptable carrier. Examples of the pharmaceutically acceptable carrier include an excipient, a binder, a disintegrant, a surfactant, a lubricant, a fluidity promoter, a corrigent, a colorant, a flavor, a diluent, a disinfecting agent, an osmotic pressure adjuster, a pH adjuster, an emulsifying agent, a preservative, a stabilizer, an absorption aid, an antioxidant, an ultraviolet absorber, a humectant, a viscosity enhancer, a glazing agent, an activity enhancer, an anti-inflammatory agent, a tonicity agent, a soothing agent, and a flavoring agent.

Examples of the binder include starch, dextrin, powder gum arabic, gelatin, hydroxypropyl starch, methylcellulose, sodium carboxymethylcellulose, hydroxypropylcellulose, crystalline cellulose, ethylcellulose, polyvinylpyrrolidone, and macrogol.

Examples of the disintegrant include starch, hydroxypropyl starch, sodium carboxymethylcellulose, calcium carboxymethylcellulose, carboxymethylcellulose, low-substituted hydroxypropylcellulose.

Examples of the surfactant include sodium lauryl sulfate, soy lecithin, sucrose fatty acid ester, and polysorbate 80.

Examples of the lubricant include talc, waxes, hydrogenated vegetable oil, sucrose fatty acid ester, magnesium stearate, calcium stearate, aluminum stearate, and polyethylene glycol.

Examples of the fluidity promoter include light anhydrous silicic acid, dried aluminum hydroxide gel, synthesized aluminum silicate, and magnesium silicate.

Examples of the diluent include distilled water for injection, physiological saline, an aqueous solution of glucose, olive oil, sesame oil, peanut oil, soybean oil, corn oil, propylene glycol, and polyethylene glycol.

When a medicine containing a compound represented by the formula (1) or a salt thereof as an active ingredient is systemically administered, a preferable dosage form is an injection or an orally administered agent, and as the injection, an intravenous injection is particularly preferable. In that case, the medicine can be administered via other injection routes such as a subcutaneous, intramuscular, or intraperitoneal injection, or the medicine can be administered transmucosally or percutaneously using a penetrant such as bile salt or fuchsin acid, or other surfactants. The aforementioned administration of a pharmaceutical composition may be given locally or in the form of an ointment, a paste, a gel, and the like.

The NFκB inhibitor of the present invention can be used not only as the pharmaceutical products as described above but also as foods, drinks, and the like. In that case, the phenanthroindolizidine alkaloid compound or the salt thereof of the present invention may be contained in foods and drinks as-is or together with various nutritional components. The foods and drinks obtained in such a manner can be utilized as food products for health use or foodstuff which are useful for improvement, prevention, etc. of proliferation or metastasis of cancer, resistance against anticancer agents, inflammatory disease (rheumatoid arthritis, osteoarthritis, atopic dermatitis, bronchial asthma, psoriasis, inflammatory bowel disease, and the like), cardiovascular disease (ischemic disease, vascular restenosis after percutaneous transluminal coronary angioplasty (PTCA), and the like), pulmonary fibrosis, diabetes, autoimmune disease, viral disease, Alzheimer's disease, ichorrhemia, metabolic syndrome, and the like. These foods and drinks or a container thereof may display that the foods and drinks have the aforementioned effects. Specifically, when the NFκB inhibitor of the present invention is added to foods and drinks, they may be shaped into a form suitable for ingestion, for example, a granule, a grain, a tablet, a capsule, and a paste, by ordinary means using additives permitted for use in foods and drinks, if desired. Also, the NFκB inhibitor of the present invention may be added to various food products, for example, a processed meat product such as ham and sausage, a processed seafood product such as cooked minced fish or fish sausage, bread, confectionery, butter, dry milk, and fermented foods and drinks, or the NFκB inhibitor of the present invention may also be added to drinks such as water, fruit juice, milk, a soft drink, and a tea drink. It is to be noted that the foods and drinks also include feed for the animal.

Further, as the foods and drinks, fermented milk products such as fermented milk, fermented bacterial drinks, fermented soymilk, fermented fruit juice, and fermented vegetable juice containing the phenanthroindolizidine alkaloid compound or a salt thereof as an active ingredient are preferably employed. These fermented milk foods and drinks may be produced by an ordinary method. For example, fermented milk is obtained by inoculating lactic acid bacteria and bifidobacteria into a sterilized milk medium and culturing them, and subjecting the resulting product to homogenization treatment to give a fermented milk base. Subsequently, a separately-prepared syrup solution and the phenanthroindolizidine alkaloid compound or a salt thereof are added and mixed, and the resulting product is homogenized using a homogenizer and the like, and a flavor is further added to prepare the final product. The fermented milk foods and drinks obtained in such a manner may also be provided in the form of, for example, any of plain type, soft type, fruit-flavored type, solid, and liquid products.

No strict limitation is imposed on the dosage amount of the phenanthroindolizidine alkaloid compound or a salt thereof, which is the active ingredient of the NFκB inhibitor of the present invention. Because the effects achieved vary depending on various usage patterns involving the subject of administration, indication, and the like, the dosage amount is desirably determined for each case, and a dosage amount of the phenanthroindolizidine alkaloid compound or a salt thereof is preferably 1 mg to 10 g, more preferably 10 mg to 1 g, per day.

The NFκB inhibitor of the present invention can be applied to all kinds of mammals including human.

EXAMPLES

As described hereinbelow, while the present invention will be further described in detail with Examples, the present invention is not limited thereto.

The phenanthroindolizidine alkaloid of the present invention was synthesized in accordance with a reaction pathway including the following steps 1 to 10. When any of the substituents represented by R needed to be protected for the reaction to proceed, a suitable protecting group was used to carry out the reaction.

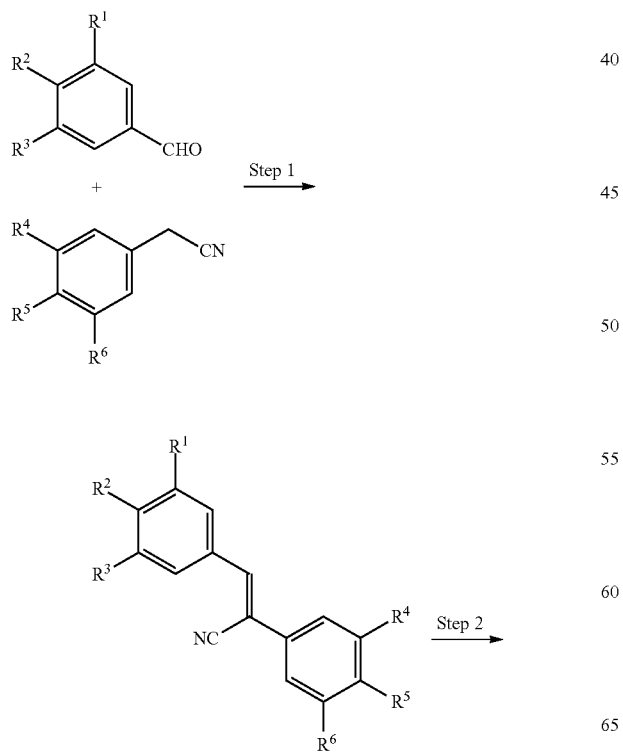

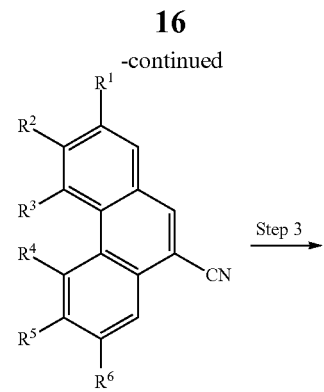

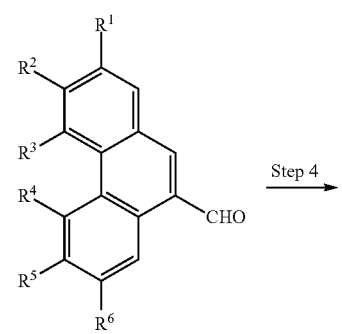

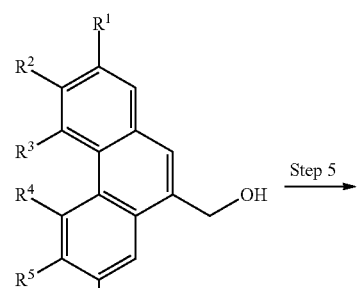

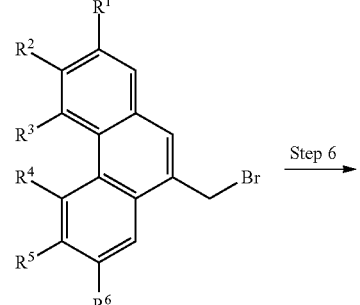

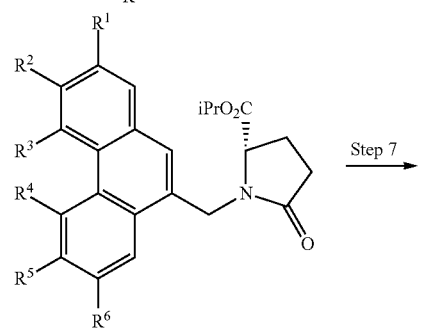

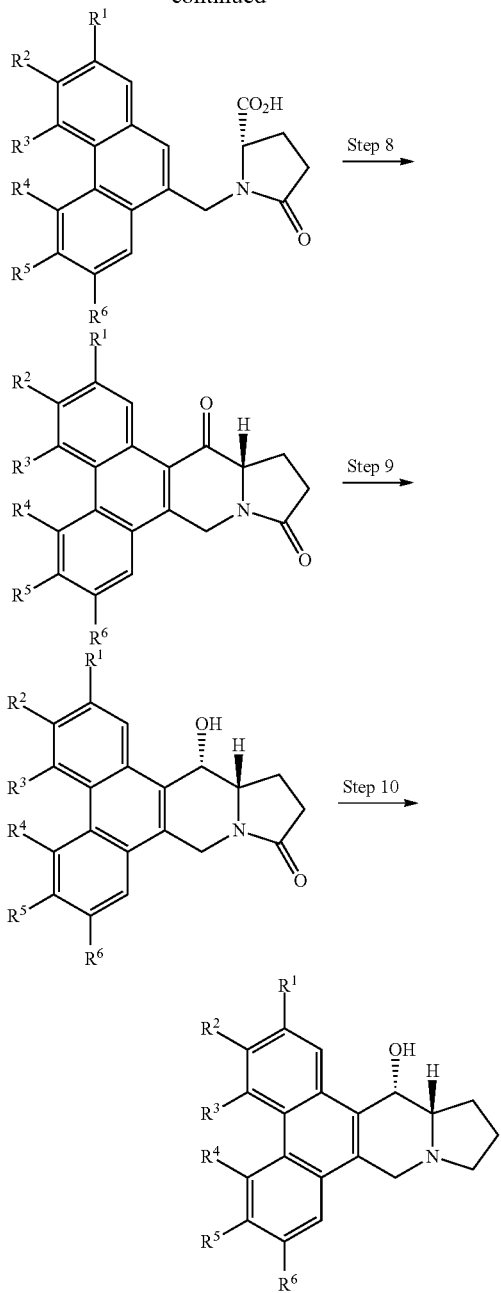

Synthesis Example 1

A compound having the following groups at $R^1$ to $R^6$ was synthesized. The operations of the steps 1 to 10 will be described below.

TABLE 1

| Compound 1 | | | | | |
|---|---|---|---|---|---|
| $R^1$ | $R^2$ | $R^3$ | $R^4$ | $R^5$ | $R^6$ |
| H | OH | H | $OCH_3$ | $OCH_3$ | $OCH_3$ |

Step 1: Synthesis of Stilbene

In a round-bottom flask, 160 mg (2.4 mmol, 0.1 eq.) of sodium ethoxide was added to a suspension of 5.0 g (24.1 mmol) of 3,4-5-trimethoxybenzyl cyanide and 5.1 g (24.1 mmol, 1.0 eq.) of 4-hydroxybenzaldehyde in 150 mL of ethanol under an argon atmosphere at room temperature while stirring, and the resulting mixture was heated to reflux (the oil bath temperature: 85° C.). After three hours, the disappearance of the raw materials was confirmed, and the resulting reaction liquid was cooled on ice to precipitate a solid. The solid was then collected by suction filtration using a Büchner funnel and a filtering flask, which was then washed with 100 mL of methanol twice. The solid was dried under reduced pressure at 60° C. to give 9.3 g (97%) of light yellow powder.

$^1$HNMR (400 MHz, $CDCl_3$) δ 3.87 (s, 3H), 3.91 (s, 6H), 5.12 (s, 2H), 6.83 (s, 2H), 7.04 (d, J=8.8 Hz, 2H), 7.30-7.45 (m, 6H), 7.85 (d, J=8.8 Hz, 2H)

Step 2: Synthesis of Phenanthrene by Photoinduced Electrocyclic Reaction

In a photoreaction container, argon was infused into a solution of 4.0 g (10.0 mmol) of stilbene in 7 L of acetonitrile at room temperature while stirring. After 10 minutes, 2.5 g (10.0 mmol, 1.0 eq.) of iodine and 28 mL (400.0 mmol, 40 eq.) of propylene oxide were added, followed by irradiation of light at room temperature while stirring. After 72 hours of irradiation, the disappearance of the raw materials was confirmed, and the resulting reaction liquid was concentrated. The residual product was dissolved in 500 mL of chloroform, followed by washing with 1 L of saturated sodium thiosulfate and 500 mL of brine. The organic layer was dried over magnesium sulfate, and then the solvent was distilled under reduced pressure to give a solid. The solid was collected by suction filtration using a Büchner funnel and a filtering flask, which was then washed with 50 mL of methanol twice. The solid was dried under reduced pressure at 60° C. to give 2.6 g (64%) of light brown powder.

$^1$HNMR (400 MHz, $CDCl_3$) δ 3.87 (s, 3H), 4.04 (s, 3H), 4.08 (s, 3H), 5.31 (s, 2H), 7.33 (dd, J=2.7, 8.8 Hz, 1H), 7.34-7.53 (m, 5H), 7.49 (s, 1H), 7.82 (d, J=8.8 Hz, 1H), 8.12 (s, 1H), 9.13 (d, J=2.7 Hz, 1H)

Step 3: Reduction of a Cyano Group by Diisobutylaluminum Hydride

In a round-bottom flask, a solution of 5.1 mL of 1.0 M diisobutylaluminum hydride in methylene chloride (5.1 mmol, 1.3 eq.) was added dropwise to a solution of 1.6 g (3.9 mmol) of cyanide in 200 mL of methylene chloride under an argon atmosphere while stirring with cooling on ice. During the dropwise addition, the mixture turned into a yellow suspension. The suspension was stirred for one hour on ice, and then for three hours at room temperature, and then the disappearance of the raw materials was confirmed. The resulting reaction liquid was cooled on ice, and 100 mL of 10% hydrochloric acid was slowly added to the liquid. The reaction liquid turned into a suspension, which was dissolved in a solution of chloroform-methanol=4:1. The organic layer was separated and the aqueous layer was extracted with a solution of chloroform-methanol=4:1. The organic layer was combined and the resulting mixture was dried over magnesium sulfate. The solvent was then removed under reduced pressure to give 1.4 g (90%) of a yellow solid.

$^1$HNMR (400 MHz, $CDCl_3$) δ 3.87 (s, 3H), 4.05 (s, 3H), 4.08 (s, 3H), 5.33 (s, 2H), 7.34 (dd, J=2.4, 8.8 Hz, 1H), 7.36-7.56 (m, 5H), 7.93 (d, J=8.8 Hz, 1H), 8.12 (s, 1H), 8.96 (s, 1H), 9.18 (d, J=2.4 Hz, 1H), 10.24 (s, 1H)

Step 4: Reduction of Aldehyde by Sodium Borohydride

In a round-bottom flask, 148 mg (3.9 mmol, 1.1 eq.) of sodium borohydride was added to a suspension of 1.4 g (3.5 mmol) of aldehyde in 40 mL of methanol and 80 mL of 1,4-dioxane under an argon atmosphere while stirring with cooling on ice. After one hour, the disappearance of the raw materials was confirmed, and 100 mL of brine was added to the resulting reaction liquid. Further, a solution of chloroform-methanol=4:1 was added to give a complete solution, and then, the organic layer was separated and the aqueous layer was extracted with a solution of chloroform-methanol=4:1. The organic layer was combined and the resulting mixture was dried over magnesium sulfate. The solvent was then removed under reduced pressure to give 1.5 g (quant) of a light brown solid.

$^1$HNMR (400 MHz, CDCl$_3$) δ 3.87 (s, 3H), 4.037 (s, 3H), 4.044 (s, 3H), 5.10 (s, 2H), 5.29 (s, 2H), 7.28 (dd, J=2.4, 8.8 Hz, 1H), 7.30-7.56 (m, 5H), 7.44 (s, 1H), 7.64 (s, 1H), 7.76 (s, 1H), 7.76 (d, J=8.8 Hz, 1H), 9.13 (d, J=2.4 Hz, 1H)

Step 5: Bromination of a Hydroxyl Group

In a recovery flask, 492 µL (3.5 mmol, 1 eq.) of triethylamine was added to a suspension of 1.5 g (3.5 mmol) of alcohol in 50 mL of chloroform under an argon atmosphere. And then, while stirring with cooling on ice, 336 µL (3.5 mmol, 1.0 eq.) of phosphorus tribromide was slowly added dropwise. After two hours, the disappearance of the raw materials was confirmed, and 30 mL of water was slowly added dropwise to precipitate a solid. After 30 minutes, the solid was dissolved in a solution of chloroform-methanol=4:1. The organic layer was separated and the aqueous layer was extracted with a solution of chloroform-methanol=4:1. The organic layer was collected and dried over magnesium sulfate, and then, the solvent was removed under reduced pressure to give 1.6 g (95%) of the reaction product.

Step 6: Introduction of a Glutamic Acid Unit

In a round-bottom flask, 491 mg (2.1 mmol, 1.25 eq.) of L-glutamic acid diisopropyl ester and 588 mg (4.3 mmol, 2.5 eq.) of potassium carbonate were added to a solution of 783 mg (1.7 mmol) of bromide in 20 mL of DMF and 20 mL of benzene, followed by stirring while heating at 80° C. After two hours, the disappearance of the raw materials was confirmed. The resulting reaction liquid was cooled on ice, and 100 mL of water and 100 mL of brine were added to the liquid. Further, 200 mL of ethyl acetate was added, and then the organic layer was washed with each of a saturated aqueous solution of sodium bicarbonate and saturated saline. The resulting solution was dried over magnesium sulfate, and the solvent was removed under reduced pressure to give an aminated crude product.

A solution of the crude product obtained in such a manner in 16 mL of methanol, 16 mL of 1,4-dioxane, and 8 mL of acetic acid was stirred at 45° C. After 16 hours, the disappearance of the raw materials was confirmed. The resulting reaction liquid was allowed to stand to cool, and 100 mL of brine was added to the liquid. Further, a saturated aqueous solution of sodium bicarbonate was gradually added to make the aqueous layer weakly basic. The aqueous layer was extracted with ethyl acetate, and the organic layer was dried over magnesium sulfate. The solvent was then removed under reduced pressure. The residual product was purified by silica gel column chromatography (hexane:ethyl acetate=1:1) to give 153 mg (15%) of a white solid.

Step 7: Hydrolysis of Pyroglutamic Acid Ester

In a round-bottom flask, an aqueous solution of potassium hydroxide (KOH: 70 mg (1.2 mmol, 4.5 eq.), H$_2$O:5 mL) was added to a solution of 153 mg (0.3 mmol) of ester in 10 mL of methanol and 20 mL of 1,4-dioxane at room temperature while stirring. After one hour, the disappearance of the raw materials was confirmed, and the solvent was distilled under reduced pressure. To the remaining aqueous solution, 1 mol/L hydrochloric acid was added little by little while stirring with cooling on ice to achieve a pH of 2 to 3 to precipitate a white solid. The white solid was collected by suction filtration using a Büchner funnel and a filtering flask, which was washed with 50 mL of purified water twice. The receiver was replaced by another filtering flask, and the solid was dissolved in a solution of chloroform-methanol=4:1. The resulting solution was transferred to a separatory funnel, and the organic layer was separated and dried over magnesium sulfate. Thereafter, the solvent was removed under reduced pressure to give 114 mg (81%) of a yellow to white solid. The results of the steps 5 to 7 will be described below.

$^1$HNMR (400 MHz, DMSO-d$_6$) δ 1.80-1.92 (m, 1H), 2.06-2.22 (m, 1H), 2.30-2.40 (m, 2H), 3.65-3.71 (m, 1H), 3.80 (s, 3H), 3.88 (s, 3H), 3.90 (s, 3H), 4.23 (d, J=14.7 Hz, 1H), 5.29 (s, 2H), 5.34 (d, J=14.7 Hz, 1H), 7.28-7.36 (m, 2H), 7.38-7.46 (m, 3H), 7.50-7.56 (m, 3H), 7.84 (d, J=8.8 Hz, 1H), 8.97 (d, J=2.4 Hz, 1H)

Step 8: Intramolecular Friedel-Crafts Acylation Reaction

In a round-bottom flask, 41 µL (0.5 mmol, 2.0 eq.) of oxalyl chloride and one drop of DMF were added to a suspension of 114 mg (0.2 mmol) of carboxylic acid in 20 mL of methylene chloride under an argon atmosphere at room temperature while stirring. After one hour, 690 µL (0.7 mmol, 3.0 eq.) of 1.0 M tin chloride (IV) in methylene chloride was slowly added. Upon completion of the dropwise addition, the resulting mixture was heated to reflux. After four hours, the disappearance of the raw materials was confirmed. The resulting reaction mixture (a brown to orange suspension) was cooled on ice, and 50 mL of 1 mol/L hydrochloric acid was added, followed by stirring for 30 minutes. A solution of chloroform-methanol=4:1 was added to turn the mixture into a solution, and subsequently the organic layer was washed with each of 1 mol/L hydrochloric acid, a saturated aqueous solution of sodium bicarbonate, and brine. The organic layer was dried over magnesium sulfate and the solvent was removed under reduced pressure. The residual product was purified by silica gel column chromatography (chloroform-methanol=50:1) to give 70 mg (60%) of a yellow solid.

Step 9: Diastereoselective Reduction of Ketone by Lithium Tri-Secondary Butyl Borohydride In a round-bottom flask, 300 µl (2.0 eq.) of lithium tri-secondary butyl borohydride (1.0 M solution in THF) was added to 20 mL (70 mg (0.15 mmol)) of Ketone in THF at −78° C. under an argon atmosphere. After one hour, the disappearance of the raw materials was confirmed, and saturated aqueous ammonium chloride was then added to the resulting reaction liquid to quench the reaction. The aqueous layer was extracted with ethyl acetate, and the organic layer was dried over anhydrous magnesium sulfate. The solvent was removed under reduced pressure, and the residual product was purified by silica gel column chromatography (chloroform-methanol=100:1) to give 39 mg (52%) of a brown solid. The results of the steps 8 and 9 will be described below.

$^1$HNMR (400 MHz, CDCl$_3$) δ 2.26-2.42 (m, 1H), 2.50-2.63 (m, 2H), 2.68-2.83 (m, 1H), 3.90-4.20 (m, 1H), 3.92 (s, 3H), 3.99 (s, 6H), 4.45 (d, J=17.4 Hz, 1H), 5.16-5.23 (m, 1H), 5.39 (d, J=17.4 Hz, 1H), 7.00 (s, 1H), 7.20 (dd, J=8.8, 2.4 Hz, 1H), 8.15 (d, J=8.8 Hz, 1H), 9.00 (d, J=2.4 Hz, 1H)

Step 10: Reduction of Lactam

In a round-bottom flask, 320 µL (0.32 mmol, 4.0 eq.) of 1.0 M BH$_3$.THF in THF was added dropwise to a solution of 40 mg (0.08 mmol) of lactam in 30 mL of THF under an argon atmosphere while stirring with cooling on ice. After two hours, the disappearance of the raw materials was confirmed. The resulting reaction liquid was cooled on ice, and 49 µL (0.32 mmol, 4.0 eq.) of N,N,N',N'-tetramethylethylenediamine was added to the liquid while stirring. After 16 hours, the disappearance of an amine-borane complex was confirmed, and the solvent was removed under reduced pressure, and then, the residual product was purified by silica gel column chromatography (chloroform-methanol=50:1) to give 16 mg (38%) of a white solid.

yield: 38%, 98.9% ee (HPLC condition B)
$^1$HNMR (400 MHz, CDCl$_3$) δ 1.82-2.12 (m, 4H), 2.26-2.56 (m, 3H), 3.24-3.36 (m, 2H), 3.90 (s, 6H), 4.06 (s, 3H), 5.03 (s, 1H), 6.48-6.55 (m, 1H), 7.20 (dd, J=8.8, 2.4 Hz, 1H), 8.38 (d, J=8.8 Hz, 1H), 8.99 (d, J=2.4 Hz, 1H)

The reactions were carried out using D-glutamic acid isopropyl ester instead of L-glutamic acid diisopropyl ester in the aforementioned step 6, and then in the subsequent steps, the reactions were carried out in the same manner as that mentioned above to give an enantiomer. The following enantiomers were also produced in the same manner.
<Enantiomer> (Compound 2)
yield: 13%, 95.8% ee Synthesis Example 2

A compound having the following groups at R$^1$ to R$^6$ was synthesized. The operations and the yield of each operation are shown below.

TABLE 2

| Compound 3 | | | | | |
|---|---|---|---|---|---|
| R$^1$ | R$^2$ | R$^3$ | R$^4$ | R$^5$ | R$^6$ |
| H | OH | H | H | H | H |

Step 1
yield: 92.0%
$^1$HNMR (400 MHz, CDCl$_3$) δ: 5.14 (2H, s), 7.02-7.08 (2H, m), 7.32-7.48 (9H, m), 7.62-7.68 (2H, m), 7.85-7.92 (2H, m)
Step 2
yield: 84.3%
$^1$HNMR (400 MHz, CDCl$_3$) δ: 5.32 (2H,), 7.30-7.56 (7H, m), 7.68-7.80 (2H, m). 7.82-7.90 (1H, m), 8.13 (1H, s), 8.18-8.21 (1H, m), 8.24-8.33 (1H, m), 8.54-8.64 (1H, m)
Step 3
yield: 94.2%
$^1$HNMR (400 MHz, CDCl$_3$) δ: 5.33 (2H, s), 7.34-7.57 (5H, m), 7.41 (1H, dd, J=2.44, 8.80 Hz), 7.68-7.77 (2H, m), 7.98 (1H, d, J=8.80 Hz), 8.14 (1H, d, J=2.44 Hz), 8.54-8.64 (1H, m), 8.21 (11H, s), 9.36-9.44 (1H, m), 10.33 (1H, s)
Step 4
yield: 98.8%
$^1$HNMR (400 MHz, CDCl$_3$) δ: 5.18 (2H, s), 5.30 (2H, s), 7.32 (1H, dd, J=2.56, 8.64 Hz), 7.35-7.47 (3H, m), 7.52-7.57 (2H, m), 7.63-7.70 (2H, m), 7.74 (1H, s), 7.81 (1H, d, J=8.64 Hz), 8.14 (1H, d, J=2.56 Hz), 8.13-8.22 (1H, m), 8.58-8.65 (1H, m)
Step 5
yield: 51.7%
$^1$HNMR (400 MHz, CDCl$_3$) δ: 5.02 (2H, s), 5.30 (2H, s), 7.32 (1H, dd, J=2.56, 8.68 Hz), 7.34-7.48 (3H, m), 7.50-7.57 (2H, m), 7.64-7.74 (2H, m), 7.79 (1H, d, J=8.68 Hz), 7.80 (1H, s), 8.12 (1H, d, J=2.56 Hz), 8.17-8.24 (1H, m), 8.58-8.65 (1H, m)
Step 6
yield: 34.8%, 93% ee (HPLC condition C)
$^1$HNMR (400 MHz, CDCl$_3$) δ: 1.17 (3H, d, J=6.21 Hz), 1.18 (3H, d, J=6.21 Hz), 1.90-2.00 (1H, m), 2.06-2.12 (1H, m), 2.37-2.48 (1H, m), 2.52-2.65 (1H, m), 3.72 (1H, dd, J=3.20, 9.28 Hz), 4.37 (1H, d, J=14.52 Hz), 5.00 (1H, heptet, J=6.21 Hz), 5.30 (2H, s), 5.63 (1H, d, J=14.52 Hz), 7.32 (1H, dd, J=2.44, 8.80 Hz), 7.33-7.46 (3H, m), 7.53 (1H, s), 7.50-7.56 (2H, m), 8.13 (1H, dd, J=2.44 Hz), 8.57-8.63 (1H, m)
Step 7
yield: 78.6%
$^1$HNMR (400 MHz, DMSO-d$_6$) δ: 1.85-1.96 (1H, m), 2.08-2.24 (1H, m), 2.28-2.47 (2H, m), 3.75 (1H, dd, J=3.04, 9.40 Hz), 4.31 (1H, d, J=27.0 Hz), 5.37 (2H, s), 5.39 (1H, d, J=27.0 Hz), 7.30-7.45 (5H, m), 7.52-7.57 (1H, m), 7.60 (1H, s), 7.62-7.72 (2H, m), 7.90 (1H, d, J=8.80 Hz), 8.03-8.06 (1H, m), 8.32 (1H, d, J=2.20 Hz), 8.84-8.89 (1H, m)
Step 8
yield: 16.4%, 97.0% ee (HPLC condition D)
$^1$HNMR (400 MHz, CDCl$_3$) δ: 2.48-3.00 (4H, m), 4.51-4.61 (1H, m), 4.79 (1H, d, J=18.18 Hz), 5.56 (1H, d, J=18.18 Hz), 7.15-7.20 (1H, m), 7.70-7.85 (2H, m), 8.01-8.07 (1H, m), 8.17-8.24 (1H, m), 8.60-8.67 (1H, m), 9.06-9.12 (1H, m)
Step 9
yield: 55.6%, [α]$_D^{28}$+121.03 (c=0.05, CH$_3$OH)
$^1$HNMR (400 MHz, CDCl$_3$) δ: 2.26-2.38 (1H, m), 2.48-2.68 (2H, m), 2.71-2.84 (1H, m), 3.87-3.93 (1H, m), 4.45 (1H, d, J=17.70 Hz), 5.04-5.10 (1H, m), 5.47 (1H, d, J=17.70 Hz), 6.50-6.58 (1H, m), 7.13 (1H, dd, J=2.32-8.91 Hz), 7.51-7.68 (3H, m), 7.84-7.90 (1H, m), 7.96 (1H, d, J=8.91 Hz), 8.11-8.17 (1H, m)
Step 10
yield: 49.0%, 97.4% ee (HPLC condition D), [α]$_D^{28}$+97.1 (c=0.04, CH$_3$OH:CHCl$_3$=1:1)
$^1$HNMR (400 MHz, DMSO-d$_6$) δ: 1.76-1.90 (3H, m), 2.12-2.25 (1H, m), 2.30-2.48 (2H, m), 3.25-3.47 (1H, m), 3.49 (1H, d, J=15.87 Hz), 4.60 (1H, d, J=15.87 Hz), 4.64-4.69 (0.5H, m), 4.90-4.96 (1H, m), 7.16 (1H, dd, J=2.44, 8.79 Hz), 7.57-7.66 (2H, m), 7.90-7.96 (1H, m), 8.01 (1H, d, J=2.44 Hz), 8.18 (1H, d, J=8.79 Hz), 8.55-8.62 (1H, m)

Synthesis Example 3

A compound having the following groups at R$^1$ to R$^6$ was synthesized. The operation and the yield of each operation are shown below.

TABLE 3

| Compound 4 | | | | | |
|---|---|---|---|---|---|
| R$^1$ | R$^2$ | R$^3$ | R$^4$ | R$^5$ | R$^6$ |
| H | OH | H | H | F | H |

Step 1
yield: >99%
$^1$HNMR (400 MHz, CDCl$_3$) δ: 5.14 (2H, s), 7.03-7.17 (4H, m), 7.32-7.48 (6H, m), 7.58-7.67 (2H, m), 7.82-7.90 (2H, m)
Step 2
yield: 37.0%
$^1$HNMR (400 MHz, CDCl$_3$) δ: 5.32 (2H, s), 7.54-7.83 (6H, m), 7.52 (1H, s), 7.89 (1H, d, J=8.8 Hz), 7.98 (1H, d, J=2.4 Hz), 8.17 (1H, s), 8.19 (1H, dd, J=2.4, 10.7 Hz), 8.28 (1H, dd, J=5.4, 8.8 Hz)
Step 3
yield: 96.5%
$^1$HNMR (400 MHz, CDCl$_3$) δ: 5.33 (2H, s), 7.35-7.50 (5H, m), 7.51-7.57 (2H, m), 7.95-8.02 (2H, m), 8.14-8.22 (2H, m), 9.42-9.50 (1H, m), 10.28 (1H, s)

Step 4
  yield: 95.0%
  $^1$HNMR (400 MHz, CDCl$_3$) δ: 5.15 (2H, d, J=5.6 Hz), 5.29 (2H, s), 7.30-7.49 (5H, m), 7.51-7.57 (2H, m), 7.68 (1H, s), 7.81 (1H, d, J=8.80 Hz), 7.98 (1H, d, J=2.44 Hz), 8.15-8.24 (2H, m)
Step 5
  yield: 92.6%
  $^1$HNMR (400 MHz, CDCl$_3$) δ: 4.98 (2H, s), 5.29 (2H, s), 7.35 (1H, dd, J=2.44, 8.79 Hz), 7.30-7.58 (6H, m), 7.74 (1H, s), 7.79 (1H, d, J=8.79 Hz), 7.96 (1H, d, J=2.44 Hz), 8.14-8.24 (2H, m)
Step 6
  yield: 56.3%
  $^1$HNMR (400 MHz, CDCl$_3$) δ: 1.15 (3H, d, J=6.34 Hz), 1.17 (3H, d, J=6.34 Hz), 1.91-2.16 (2H, m), 2.36-2.48 (1H, m), 2.52-2.64 (1H, m), 4.38 (1H, d, J=14.65 Hz), 5.29 (2H, s), 5.56 (1H, d, J=14.65 Hz), 7.34 (1H, dd, J=2.44, 8.79 Hz), 7.32-7.56 (7H, m), 7.74 (1H, d, J=8.79 Hz), 7.96 (1H, d, J=2.44 Hz), 8.07-8.22 (2H, m)
Step 7
  yield: 77.8%
  $^1$HNMR (400 MHz, DMSO-d$_6$) δ: 1.82-1.96 (1H, m), 2.08-2.25 (1H, m), 2.28-2.48 (2H, m), 3.70-3.80 (1H, m), 4.32 (1H, d, J=14.89 Hz), 5.32 (1H, d, J=14.89 Hz), 5.37 (2H, s), 7.37 (1H, dd, J=2.20, 8.78 Hz), 7.31-7.46 (3H, m), 7.50-7.60 (4H, m), 7.90 (1H, d, J=8.78 Hz), 8.30 (1H, d, J=2.20 Hz), 8.07-8.15 (1H, m), 8.68-8.75 (1H, m)
Step 8
  yield: 28.1%, $[α]_D^{29}$+79.6 (c=0.11, CHCl$_3$)
  $^1$HNMR (400 MHz, CDCl$_3$) δ: 2.48-2.67 (4H, m), 4.40-4.50 (1H, m), 4.73 (1H, d, J=18.55 Hz), 5.30 (2H, s), 5.80 (1H, d, J=18.55 Hz), 7.33-7.57 (7H, m), 7.98 (1H, d, J=2.68 Hz), 8.10-8.23 (2H, m), 9.31 (1H, d, J=9.28 Hz)
Step 9
  yield: 37.2%
  $^1$HNMR (400 MHz, CDCl$_3$) δ: 2.19-2.34 (1H, m), 2.42-2.62 (2H, m), 2.61-2.78 (1H, m), 3.85-4.00 (1H, m), 4.39 (1H, d, J=17.82 Hz), 5.10-5.20 (1H, m), 5.26 (2H, s), 5.27 (1H, d, J=17.82 Hz), 7.30-7.56 (7H, m), 7.68-7.82 (1H, m), 7.88-7.96 (1H, m), 8.02-8.13 (1H, m), 8.15-8.25 (1H, m)
Step 10
  yield: 47.9%, $[α]_D^{28}$+112.9 (c=0.08, CHCl$_3$)
  $^1$HNMR (400 MHz, CDCl$_3$) δ: 1.82-2.04 (3H, m), 2.25-2.44 (2H, m), 2.42-2.55 (1H, m), 3.18-3.32 (1H, m), 3.32-3.46 (1H, m), 5.31 (2H, s), 4.98-5.07 (1H, m), 3.90-4.12 (1H, m), 7.41 (1H, dd, J=2.44, 9.03 Hz), 7.32-7.49 (4H, m), 7.02-7.20 (1H, m), 7.50-7.58 (2H, m), 7.94 (1H, d, J=2.44 Hz), 8.01-8.10 (1H, m), 8.37 (1H, d, J=9.03 Hz)
Step 11: Hydrogenolysis of Benzyl Ether
  To a suspension of 25 mg (0.06 mmol) of the compound obtained by the step 10 in 10 mL of methanol, 5 mg of 10% palladium on carbon was added, followed by stirring under a hydrogen atmosphere. After 24 hours, the disappearance of the raw materials was confirmed, and the palladium on carbon was removed by filtration. The resulting filtrate was evaporated under reduced pressure and the residual product was purified by column chromatography (chloroform:methanol=40:1) to give 7 mg (28.6%) of a white solid. $[α]_D^{28}$+124.0 (c=0.28, CHCl$_3$)
  $^1$HNMR (400 MHz, CDCl$_3$) δ: 1.86-2.06 (3H, m), 2.24-2.38 (1H, m), 2.40-2.52 (1H, m), 2.54-2.65 (1H, m), 3.32-3.41 (1H, m), 3.59 (1H, d, J=15.13 Hz), 4.44 (1H, d, J=15.13 Hz), 5.04-5.13 (1H, m), 7.20-7.25 (1H, m), 7.27-7.33 (1H, m), 7.68-7.78 (1H, m), 7.87 (1H, d, J=2.44 Hz), 8.08-8.15 (1H, m), 8.30 (1H, d, J=9.03 Hz)

Synthesis Example 4

A compound having the following groups at $R^1$ to $R^6$ was synthesized. The operation and the yield of each operation are shown below.

TABLE 4

| Compound 8 | | | | | |
| --- | --- | --- | --- | --- | --- |
| $R^1$ | $R^2$ | $R^3$ | $R^4$ | $R^5$ | $R^6$ |
| H | OH | H | H | —OCH$_2$O— | |

Step 1
  yield: 93%
  $^1$HNMR (400 MHz, CDCl$_3$) δ: 5.13 (2H, s), 6.02 (2H, s), 6.86 (1H, d, J=8.0 Hz), 7.04 (2H, d, J=8.8 Hz), 7.10 (1H, d, J=1.6 Hz), 7.17 (1H, dd, J=1.6, 8.0 Hz), 7.30-7.48 (6H, m), 7.84 (2H, d, J=8.8 Hz)
Step 2
  yield: 78%
  $^1$HNMR (400 MHz, CDCl$_3$) δ: 5.29 (2H, s), 6.17 (2H, s), 7.32 (1H, dd, J=2.4, 8.8 Hz), 7.35-7.39 (1H, m), 7.42-7.51 (1H, m), 7.51-7.53 (1H, m), 7.63 (1H, s), 7.82 (1H, d, J=8.8 Hz), 7.86 (1H, d, J=2.4 Hz), 7.88 (1H, s), 8.08 (1H, s)
Step 3
  yield: 95%
  $^1$HNMR (400 MHz, CDCl$_3$) δ: 5.31 (2H, s), 6.14 (2H, s), 7.32 (1H, dd, J=2.4, 8.8 Hz), 7.36-7.39 (1H, m), 7.42-7.46 (2H, m), 7.52-7.54 (2H, m), 7.88 (1H, d, J=2.4 Hz), 7.90 (1H, s), 7.93 (1H, d, J=8.8 Hz), 8.09 (1H, s), 8.92 (1H, s), 10.23 (1H, s)
Step 4
  yield: quant
  $^1$HNMR (400 MHz, CDCl$_3$) δ: 5.07 (2H, s), 5.27 (2H, s), 6.11 (2H, s), 7.26 (1H, dd, J=2.4, 8.8 Hz), 7.31-7.46 (3H, m), 7.49-7.57 (3H, m), 7.62 (1H, s), 7.76 (1H, d, J=8.8 Hz), 7.88 (1H, d, J=2.4 Hz), 7.92 (1H, s)
Step 5
  yield: 96.3%
  $^1$HNMR (400 MHz, CDCl$_3$) δ: 4.93 (2H, s), 6.14 (2H, s), 7.26 (1H, dd, J=2.4, 8.8 Hz), 7.32-7.38 (1H, m), 7.40-7.45 (2H, m), 7.49-7.56 (2H, m), 7.55 (1H, s), 7.70 (1H, s), 7.76 (1H, d, J=8.8 Hz), 7.87 (1H, d, J=2.4 Hz), 7.93 (1H, s)
Step 6
  yield: 68.0%, $[α]_D^{29}$+49.34
  $^1$HNMR (400 MHz, CDCl$_3$) δ: 1.16 (3H, d, J=6.3 Hz), 1.18 (3H, d, J=6.3 Hz), 1.82-2.00 (1H, m), 2.06-2.17 (1H, m), 2.39-2.48 (1H, m), 2.52-2.64 (1H, m), 3.71 (1H, dd, J=3.2, 9.3 Hz), 4.31 (1H, d, J=14.6 Hz), 5.27 (2H, s), 4.99 (1H, heptet, J=6.3 Hz), 5.49 (1H, d, J=14.6 Hz), 6.10 (2H, s), 7.24 (1H, dd, J=2.4, 8.8 Hz), 7.32-7.38 (1H, m), 7.39-7.46 (3H, m), 7.48 (1H, s), 7.49-7.54 (2H, m), 7.70 (1H, d, J=8.8 Hz), 7.87 (1H, d, J=2.4 Hz), 7.91 (1H, s)
Step 7
  yield: 90.3%
  $^1$HNMR (400 MHz, DMSO-d$_6$) δ: 1.83-1.93 (1H, m), 2.04-2.18 (1H, m), 2.26-2.42 (2H, m), 3.64-3.73 (1H, m), 4.21 (1H, d, J=14.6 Hz), 5.25 (1H, d, J=14.6 Hz), 5.34 (2H, s), 6.19 (2H, d, J=4.2 Hz), 7.25 (1H, dd, J=2.4, 8.8 Hz), 7.31-7.36 (1H, m), 7.38-7.43 (2H, m), 7.48-7.49 (2H, m), 7.51-7.56 (2H, m), 7.82 (1H, d, J=8.8 Hz), 8.16 (1H, d, J=2.2 Hz), 8.36 (1H, s)

Step 8
  yield: 36.6%
  $^1$HNMR (400 MHz, CDCl$_3$) δ: 2.26-2.49 (4H, m), 4.50-4.58 (1H, m), 4.69 (1H, d, J=18.1 Hz), 5.42 (1H, d, J=18.1 Hz), 6.27 (2H, d, J=1.5 Hz), 7.15 (1H, dd, J=2.4-9.3 Hz), 7.70 (1H, s), 7.90 (1H, d, J=2.4 Hz), 8.11 (1H, s), 9.08 (1H, d, J=9.3 Hz), 9.96 (1H, brs)

Step 9
  yield: 45.9%
  $^1$HNMR (400 MHz, DMSO-d$_6$) δ: 2.09-2.21 (1H, m), 2.25-2.46 (3H, m), 3.84-3.90 (1H, m), 4.40 (1H, d, J=17.3 Hz), 5.03-5.07 (1H, m), 5.06 (1H, d, J=17.3 Hz), 5.39 (1H, d, J=7.1 Hz), 6.19 (2H, dd, J=0.7, 7.1 Hz), 7.41 (1H, s), 7.13 (1H, dd, J=2.4, 9.0 Hz), 7.87 (1H, d, J=2.4 Hz), 8.05 (1H, s), 8.05 (1H, d, J=9.0 Hz), 9.80 (1H, brs)

Step 10
  yield: 41.2%
  $^1$HNMR (400 MHz, DMSO-d$_6$) δ: 1.75-1.87 (3H, m), 2.08-2.24 (1H, m), 2.30-2.41 (2H, m), 3.27-3.32 (1H, m), 3.39 (1H, d, J=15.4 Hz), 4.47 (1H, d, J=15.4 Hz), 4.58 (1H, d, J=10.0 Hz), 4.89 (1H, dd, J=1.9, 10.0 Hz), 6.17 (2H, d, J=4.0 Hz), 7.10 (1H, dd, J=2.4, 8.8 Hz), 7.33 (1H, s), 7.82 (1H, d, J=2.4 Hz), 8.01 (1H, s), 8.12 (1H, d, J=8.8 Hz), 9.73 (1H, brs)

Synthesis Example 5

A compound having the following groups at R$^1$ to R$^6$ was synthesized. The operation and the yield of each operation are shown below.

TABLE 5

| Compound 15 | | | | | |
|---|---|---|---|---|---|
| R$^1$ | R$^2$ | R$^3$ | R$^4$ | R$^5$ | R$^6$ |
| OCH$_3$ | OCH$_3$ | H | H | OH | H |

Step 1
  yield: quant
  $^1$HNMR (400 MHz, CDCl$_3$) δ: 3.94 (3H, s), 3.97 (3H, s), 5.12 (2H, s), 6.92 (1H, d, J=8.8 Hz), 7.01-7.06 (2H, m), 7.33 (1H, dd, J=2.0, 8.8 Hz), 7.33-7.47 (6H, m), 7.55-7.64 (2H, m), 7.68 (1H, d, J=2.0 Hz)

Step 2
  yield: 30.7%
  $^1$HNMR (400 MHz, CDCl$_3$) δ: 4.05 (3H, s), 4.12 (3H, s), 5.31 (2H, s), 7.23 (1H, s), 7.35-7.48 (4H, m), 7.51-7.57 (2H, m), 7.78 (1H, s), 7.96 (1H, d, J=2.4 Hz), 8.02 (1H, s), 8.21 (1H, d, J=9.0 Hz)

Step 3
  yield: 99.8%
  $^1$HNMR (400 MHz, CDCl$_3$) δ: 4.07 (3H, s), 4.13 (3H, s), 5.31 (2H, s), 7.33-7.48 (5H, m), 7.51-7.57 (2H, m), 7.81 (1H, s), 7.98 (1H, d, J=2.7 Hz), 8.04 (1H, s), 9.34 (1H, d, J=9.3 Hz), 10.28 (1H, s)

Step 4
  yield: 93.0%
  $^1$HNMR (400 MHz, CDCl$_3$) δ: 4.03 (3H, s), 4.09 (3H, s), 5.14 (2H, s), 5.30 (2H, s), 7.21 (1H, s), 7.30-7.48 (4H, m), 7.51-7.57 (3H, m), 7.79 (1H, s), 7.99 (1H, d, J=2.4 Hz), 8.11 (1H, d, J=9.0 Hz)

Steps 5 and 6
  yield: 52.5%
  $^1$HNMR (400 MHz, CDCl$_3$) δ: 1.17 (3H, d, J=6.2 Hz), 1.18 (1H, d, J=6.2 Hz), 1.90-2.05 (1H, m), 2.05-2.23 (1H, m), 2.36-2.52 (1H, m), 2.52-2.64 (1H, m), 3.73 (1H, dd, J=3.4, 9.3 Hz), 4.02 (3H, s), 4.09 (3H, s), 4.33 (1H, d, J=14.6 Hz), 5.07 (1H, heptet, J=6.2 Hz), 5.28 (2H, s), 5.59 (1H, d, J=14.6 Hz), 7.13 (1H, s), 7.31 (1H, dd, J=2.7, 9.0 Hz), 7.33-7.38 (2H, m), 7.39-7.46 (2H, m), 7.51-7.58 (2H, m), 7.79 (1H, s), 7.98 (1H, d, J=2.7 Hz), 8.02 (1H, d, J=9.0 Hz)

Step 7
  yield: 62.8%
  $^1$HNMR (400 MHz, DMSO-d$_6$) δ: 1.85-1.98 (1H, m), 2.10-2.23 (1H, m), 2.25-2.43 (2H, m), 3.72 (1H, dd, J=3.2, 9.3 Hz), 3.90 (3H, s), 4.01 (3H, s), 4.22 (1H, d, J=15.1 Hz), 5.36 (1H, d, J=15.1 Hz), 5.36 (2H, s), 7.29 (1H, dd, J=2.2, 9.0 Hz), 7.32-7.45 (5H, m), 7.54-7.61 (2H, m), 7.95 (1H, d, J=9.0 Hz), 8.01 (1H, s), 8.20 (1H, d, J=2.2 Hz)

Step 8
  yield: 75.4%
  $^1$HNMR (400 MHz, DMSO-d$_6$) δ: 2.28-2.45 (4H, m), 3.90 (3H, s), 4.01 (3H, s), 4.51-4.60 (1H, m), 4.78 (1H, d, J=18.2 Hz), 5.55 (1H, d, J=18.2 Hz), 7.23 (1H, dd, J=2.3, 9.2 Hz), 7.95 (1H, s), 8.02 (1H, d, J=2.3 Hz), 8.15 (1H, d, J=9.2 Hz), 8.99 (1H, s), 10.41 (1H, s)

Step 9
  yield: 45.6%
  $^1$HNMR (400 MHz, DMSO-d$_6$) δ: 2.10-2.24 (1H, m), 2.28-2.46 (3H, m), 3.86-3.93 (1H, m), 3.94 (3H, s), 3.99 (3H, s), 4.47 (1H, d, J=17.9 Hz), 5.04-5.10 (1H, m), 5.15 (1H, d, J=17.9 Hz), 5.40-5.49 (1H, m), 7.12-7.16 (1H, m), 7.59 (1H, s), 7.83 (1H, d, J=9.3 Hz), 7.93 (1H, s), 7.95-8.01 (1H, m), 9.84 (1H, s)

Step 10
  yield: 63.0%
  $^1$HNMR (400 MHz, DMSO-d$_6$) δ: 1.74-1.90 (3H, m), 2.10-2.27 (1H, m), 2.28-2.46 (2H, m), 3.26-3.40 (1H, m), 3.45 (1H, d, J=15.4 Hz), 3.91 (3H, s), 3.98 (3H, s), 4.57 (1H, d, J=15.4 Hz), 4.65 (1H, d, J=10.0 Hz), 4.91 (1H, dd, J=2.1, 10.0 Hz), 7.08 (1H, dd, J=2.4, 8.9 Hz), 7.78 (1H, d, J=8.9 Hz), 7.89 (1H, s), 7.94 (1H, d, J=2.4 Hz), 9.74 (1H, s)

Derivatives in which stilbene was synthesized by a method different from that described above were synthesized through the synthetic pathway shown in the following steps 12 to 17. The reactions after the step 17 were carried out under similar reaction conditions to those used for the reactions after the step 5 described above.

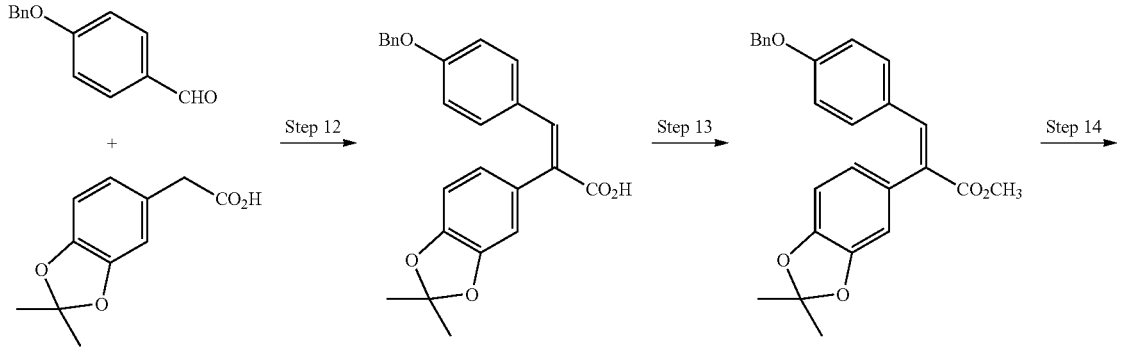

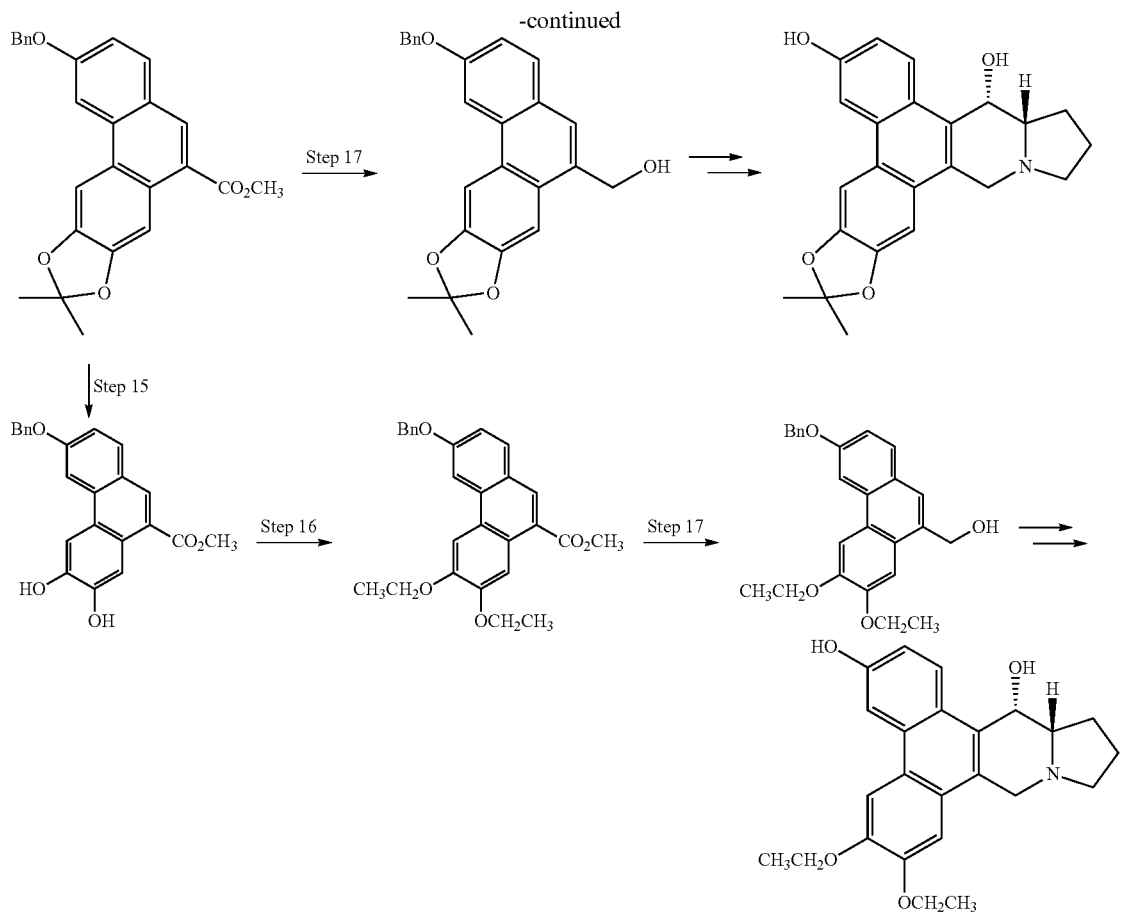

Synthesis Example 6

A compound having the following groups at $R^1$ to $R^6$ was synthesized. The operation and the yield of each operation are shown below.

TABLE 6

| Compound 9 | | | | | |
|---|---|---|---|---|---|
| $R^1$ | $R^2$ | $R^3$ | $R^4$ | $R^5$ | $R^6$ |
| H | OH | H | H | | —OC(CH$_3$)$_2$O— |

Step 12: Synthesis of Stilbene

In a round-bottom flask, 8.6 g (41.4 mmol) of 3,4-isopropylidenedioxyphenyl acetate, 13.2 g (62.2 mmol, 1.5 eq.) of 4-benzyloxybenzaldehyde, 8.6 mL (62.2 mmol, 1.5 eq.) of triethylamine, and 20 mL (207 mmol, 5 eq.) of anhydrous acetic acid were added, followed by stirring while heating. After six hours, the disappearance of the raw materials was confirmed. The resulting reaction liquid was allowed to stand to cool and water was then added to quench the reaction. Diluted hydrochloric acid was added and the resulting liquid was then extracted with ethyl acetate. The organic layer was dried over anhydrous magnesium sulfate, and then the solvent was removed under reduced pressure. The residual product was purified by column chromatography (hexane:ethyl acetate=5:1→1:1) to give 7.5 g (44.8%) of an oily product.

$^1$HNMR (400 MHz, CDCl$_3$) δ: 1.71 (6H, s), 5.04 (2H, s), 6.60-6.83 (6H, m), 7.08-7.12 (2H, m), 7.36-7.40 (4H, m), 7.79 (1H, s)

Step 13: Methyl Esterification

In a round-bottom flask, 2.4 mL (27.5 mmol, 1.5 eq.) of oxalyl chloride was added to a solution of 7.3 g (18.4 mmol) of carboxylic acid in 70 mL of methylene chloride, which was the raw material, under an argon atmosphere. After 30 minutes, the production of acid chloride was confirmed, and then the reaction was cooled to 0° C., followed by addition of 3 mL (73.6 mmol, 4 eq.) of methanol. After one hour, the disappearance of the raw materials was confirmed, and brine was added to the resulting reaction liquid. The aqueous layer was extracted with chloroform, and the organic layer was collected and dried over anhydrous magnesium sulfate. The solvent was then removed under reduced pressure to give 8.8 g (quant) of a crude product.

$^1$HNMR (400 MHz, CDCl$_3$) δ: 1.71 (6H, s), 3.78 (3H, s), 5.02 (2H, s), 6.59-6.81 (6H, m), 7.04-7.07 (2H, m), 7.36-7.40 (4H, m), 7.74 (1H, s)

Step 14: Synthesis of Phenanthrene by Photoinduced Electrocyclic Reaction

In a photoreaction container, argon was infused into a solution of 8.7 g (18.4 mmol) of stilbene in 7 L of acetonitrile for approximately 10 minutes at room temperature while stirring. After 10 minutes, 4.7 g (18.4 mmol, 1.0 eq.) of iodine and 52 mL (736.0 mmol, 40 eq.) of propylene oxide were added, followed by irradiation of light at room temperature while stirring. After 72 hours of irradiation, the disappearance of the raw materials was confirmed, and the resulting reaction liquid was concentrated. The residual product was dissolved in 500 mL of chloroform, followed by washing with 1 L of saturated sodium thiosulfate and 500 mL of saturated saline.

The organic layer was dried over magnesium sulfate, and then the solvent was removed under reduced pressure to give a solid. The solid was collected by suction filtration using a Büchner funnel and a filtering flask, which was then washed with 50 mL of methanol twice. The solid was then dried under reduced pressure at 60° C. to give 6.3 g (66.5%) of light brown powder.

$^1$HNMR (400 MHz, CDCl$_3$) δ: 1.77 (6H, s), 4.00 (3H, s), 5.28 (2H, s), 7.27 (1H, dd, J=2.4, 8.8 Hz), 7.34-7.46 (4H, m), 7.50-7.54 (2H, m), 7.83 (1H, s), 7.84 (1H, d, J=8.8 Hz), 7.86 (1H, d, J=2.4 Hz), 8.34-8.36 (1H, m)

Step 17: Reduction of Ester

Under an argon atmosphere, a solution of 9.6 mL of 1.0 M diisobutylaluminum hydride in toluene (9.6 mmol, 4.4 eq.) was added dropwise to a solution of 900 mg (2.2 mmol) of methyl ester in 20 mL of methylene chloride in a round-bottom flask at 0° C. After one hour, the disappearance of the raw materials was confirmed, and 1 M hydrochloric acid was slowly added to quench the reaction. The aqueous layer was extracted with chloroform, and the organic layer was dried over anhydrous magnesium sulfate. The solvent was then removed under reduced pressure to give 988 mg (quant) of a crude product.

$^1$HNMR (400 MHz, CDCl$_3$) δ: 1.77 (6H, s), 5.07 (2H, s), 5.26 (2H, s), 7.24 (1H, dd, J=2.4, 8.8 Hz), 7.32-7.44 (3H, m), 7.47 (1H, s), 7.50-7.54 (2H, m), 7.60 (1H, s), 7.76 (1H, d, J=8.8 Hz), 7.54 (1H, s), 7.87 (1H, d, J=2.4 Hz)

Step 5
 yield: 90.2%
 $^1$HNMR (400 MHz, CDCl$_3$) δ: 1.79 (6H, s), 4.92 (2H, s), 5.26 (2H, s), 7.24 (1H, dd, J=2.4, 8.8 Hz), 7.32-7.38 (1H, m), 7.40-7.47 (3H, m), 7.49-7.54 (2H, m), 7.67 (1H, s), 7.74 (1H, d, J=8.8 Hz), 7.84 (1H, s), 7.85 (1H, d, J=2.4 Hz)

Step 6
 yield: 61.6%
 $^1$HNMR (400 MHz, CDCl$_3$) δ: 1.18 (3H, d, J=6.4 Hz), 1.19 (3H, d, J=6.4 Hz), 1.74 (3H, s), 1.77 (3H, s), 1.91-2.00 (1H, m), 2.08-2.18 (1H, m), 2.40-2.850 (1H, m), 2.53-2.64 (1H, m), 3.74 (1H, dd, J=3.2, 9.3 Hz), 4.29 (1H, d, J=14.4 Hz), 5.01 (1H, heptet, J=6.4 Hz), 5.26 (2H, s), 5.49 (1H, d, J=14.4 Hz), 7.24 (1H, dd, J=2.4, 8.8 Hz), 7.34-7.45 (5H, m), 7.50-7.54 (2H, m), 7.69 (1H, d, J=8.8 Hz), 7.83 (1H, s), 7.86 (1H, d, J=2.4 Hz)

Step 7
 yield: 95.7%
 $^1$HNMR (400 MHz, DMSO-d$_6$) δ: 1.72 (3H, s), 1.75 (3H, s), 1.83-1.94 (1H, m), 2.10-2.22 (1H, m), 2.28-2.43 (2H, m), 3.75 (1H, dd, J=3.0, 9.3 Hz), 4.20 (1H, d, J=14.9 Hz), 5.24 (1H, d, J=14.9 Hz), 5.34 (2H, s), 7.25 (1H, dd, J=2.4, 8.8 Hz), 7.31-7.36 (1H, m), 7.38-7.43 (2H, m), 7.41 (1H, s), 7.45 (1H, s), 7.51-7.57 (2H, m), 7.81 (1H, d, J=8.8 Hz), 8.12 (1H, d, J=2.4 Hz), 8.25 (1H, s)

Step 8
 yield: 84.9%
 $^1$HNMR (400 MHz, CDCl$_3$) δ: 1.80 (6H, s), 2.49-2.62 (4H, m), 4.38-4.46 (1H, m), 4.61 (1H, d, J=17.8 Hz), 5.27 (2H, s), 5.67 (1H, d, J=17.8 Hz), 7.30-7.45 (5H, m), 7.34 (1H, dd, J=2.7, 9.3 Hz), 7.50-7.54 (2H, m), 7.82 (1H, s), 7.88 (1H, d, J=2.7 Hz), 9.31 (1H, d, J=9.3 Hz)

Step 9
 yield: 50.9%
 $^1$HNMR (400 MHz, CDCl$_3$) δ: 1.77 (3H, s), 1.78 (3H, s), 2.22-2.35 (1H, m), 2.50-2.60 (2H, m), 2.67-2.78 (1H, m), 3.91-3.98 (1H, m), 4.44 (1H, d, J=17.3 Hz), 5.23 (1H, d, J=2.0 Hz), 5.26 (2H, s), 5.35 (1H, d, J=17.3 Hz), 7.20 (1H, s), 7.30-7.37 (2H, m), 7.40-7.46 (2H, m), 7.49-7.54 (2H, m), 7.81 (1H, s), 7.89 (1H, d, J=2.4 Hz), 8.16 (1H, d, J=9.0 Hz)

Step 10
 yield: 76.1%
 $^1$HNMR (400 MHz, DMSO-d$_6$) δ: 1.72 (3H, s), 1.75 (3H, s), 1.78-1.86 (3H, m), 2.10-2.22 (1H, m), 2.28-2.41 (2H, m), 3.25-3.31 (1H, m), 3.40 (1H, d, J=15.6 Hz), 4.48 (1H, d, J=15.6 Hz), 4.61 (1H, d, J=9.8 Hz), 4.91 (1H, dd, J=2.0, 9.8 Hz), 5.34 (2H, s), 7.27 (1H, dd, J=2.4, 9.0 Hz), 7.27 (1H, s), 7.30-7.36 (1H, m), 7.38-7.44 (2H, m), 7.51-7.55 (2H, m), 8.10 (1H, d, J=2.4 Hz), 8.20 (1H, d, J=9.0 Hz), 8.21 (1H, s)

Step 11
 yield: 46.4%
 $^1$HNMR (400 MHz, DMSO-d$_6$) δ: 1.71 (3H, s), 1.74 (3H, s), 1.76-1.86 (3H, m), 2.09-2.21 (1H, m), 2.30-2.40 (2H, m), 3.25-3.31 (1H, m), 3.39 (1H, d, J=15.1 Hz), 4.46 (1H, d, J=15.1 Hz), 4.54 (1H, d, J=9.8 Hz), 4.89 (1H, dd, J=2.2, 9.8 Hz), 7.08 (1H, dd, J=2.4, 9.0 Hz), 7.25 (1H, s), 7.80 (1H, d, J=2.4 Hz), 7.91 (1H, s), 8.11 (1H, d, J=9.0 Hz), 9.67 (1H, brs)

Synthesis Example 7

A compound having the following groups at $R^1$ to $R^6$ was synthesized. The operation and the yield of each operation are shown below.

TABLE 7

| Compound 10 | | | | | |
|---|---|---|---|---|---|
| $R^1$ | $R^2$ | $R^3$ | $R^4$ | $R^5$ | $R^6$ |
| H | OH | H | H | CH$_3$CH$_2$O | CH$_3$CH$_2$O |

Step 15: Deprotection of Acetonide

To 2 g (4.8 mmol) of raw materials in a round-bottom flask, 20 mL of 6 N hydrochloric acid and 20 mL of acetic acid were added, followed by heating under reflux. After four hours, the disappearance of the raw materials was confirmed. The resulting reaction liquid was cooled on ice, and brine was added thereto. The aqueous layer was extracted with ethyl acetate, and the organic layer was dried over anhydrous magnesium sulfate. The solvent was then removed under reduced pressure. Chloroform was added to the residual product to precipitate a solid, which was collected by filtration using a Kiriyama funnel. The thus-obtained solid was dried under reduced pressure to give 956 mg (52.9%) of a reaction product.

$^1$HNMR (400 MHz, DMSO-d$_6$) δ: 3.91 (3H, s), 5.37 (2H, s), 7.26 (1H, dd, J=2.4, 8.8 Hz), 7.32-7.38 (1H, m), 7.40-7.45 (2H, m), 7.51-7.58 (2H, m), 7.96 (1H, d, J=8.8 Hz), 7.96 (1H, d, J=2.4 Hz), 8.05 (1H, s), 8.25 (1H, s), 8.26 (1H, s), 9.51 (1H, s), 9.90 (1H, s)

Step 16: Ethyl Etherification of a Phenolic Hydroxyl Group

In a round-bottom flask, 2.2 g (15.6 mmol, 6 eq.) of K$_2$CO$_3$ and 1.2 mL (15.6 mmol, 6 eq.) of ethyl bromide were added to a solution of 956 mg (2.6 mmol) of diol in 30 mL of acetone, followed by heating under reflux. After 12 hours, the disappearance of the raw materials was confirmed, and acetone was removed under reduced pressure. And then, brine was added to the residual product. The aqueous layer was extracted with ethyl acetate, and the organic layer was dried over anhydrous magnesium sulfate. The solvent was removed under reduced pressure, and the residual product was purified through column chromatography (hexane:ethyl acetate=3:1) to give 654 mg (76.9%) of a white solid.

$^1$HNMR (400 MHz, CDCl$_3$) δ: 1.57 (3H, t, J=7.0 Hz), 1.59 (3H, t, J=7.0 Hz), 4.00 (3H, s), 4.31 (2H, q, J=7.0 Hz), 4.32 (2H, q, J=7.0 Hz), 5.29 (2H, s), 7.27 (1H, dd, J=2.4, 8.8 Hz), 7.35-7.39 (1H, m), 7.41-7.47 (2H, m), 7.50-7.56 (2H, m), 7.85 (1H, d, J=8.8 Hz), 7.85 (1H, s), 7.89 (1H, d, J=2.4 Hz), 8.43 (1H, s), 8.63 (1H, s)

Step 17 yield: 82.9%

$^1$HNMR (400 MHz, CDCl$_3$) δ: 1.56 (3H, t, J=7.0 Hz), 1.58 (3H, t, J=7.0 Hz), 4.28 (2H, q, J=7.0 Hz), 4.31 (2H, q, J=7.0 Hz), 5.09 (2H, s), 5.28 (2H, s), 7.25 (1H, dd, J=2.4, 8.8 Hz), 7.33-7.38 (1H, m), 7.40-7.45 (2H, m), 7.52-7.57 (3H, m), 7.59 (1H, s), 7.77 (1H, d, J=8.8 Hz), 7.88 (1H, s), 7.91 (1H, d, J=2.4 Hz)

Step 5 yield: 98.4%

$^1$HNMR (400 MHz, CDCl$_3$) δ: 1.58 (6H, t, J=7.0 Hz), 4.32 (2H, q, J=7.0 Hz), 4.33 (2H, q, J=7.0 Hz), 4.96 (2H, s), 5.28 (2H, s), 7.25 (1H, dd, J=2.4, 8.8 Hz), 7.32-7.38 (1H, m), 7.39-7.45 (2H, m), 7.50-7.55 (2H, m), 7.68 (1H, s), 7.76 (1H, d, J=8.8 Hz), 7.88 (1H, s), 7.89 (1H, d, J=2.4 Hz)

Step 6 yield: 62.6%

$^1$HNMR (400 MHz, CDCl$_3$) δ: 1.17 (3H, d, J=6.1 Hz), 1.19 (3H, d, J=6.1 Hz), 1.54 (3H, t, J=7.0 Hz), 1.57 (3H, t, J=7.0 Hz), 1.90-1.99 (1H, m), 2.01-2.12 (1H, m), 2.30-2.44 (1H, m), 2.53-2.65 (1H, m), 3.70 (1H, dd, J=3.6, 9.3 Hz), 4.25 (2H, q, J=7.0 Hz), 4.29 (1H, d, J=14.4 Hz), 4.31 (2H, q, J=7.0 Hz), 5.01 (1H, heptet, J=6.1 Hz), 5.28 (2H, s), 5.58 (1H, d, J=14.4 Hz), 7.25 (1H, dd, J=2.4, 8.8 Hz), 7.32-7.37 (1H, m), 7.38-7.44 (3H, m), 7.51-7.57 (3H, m), 7.70 (1H, d, J=8.8 Hz), 7.86 (1H, s), 7.91 (1H, d, J=2.4 Hz)

Step 7 yield: 87.3%

$^1$HNMR (400 MHz, DMSO-d$_6$) δ: 1.39 (3H, t, J=7.0 Hz), 1.44 (3H, t, J=7.0 Hz), 1.81-1.91 (1H, m), 2.02-2.14 (1H, m), 2.23-2.44 (2H, m), 3.64 (1H, dd, J=3.3, 9.2 Hz), 4.15 (2H, q, J=7.0 Hz), 4.20 (1H, d, J=14.4 Hz), 4.30 (2H, q, J=7.0 Hz), 5.34 (1H, d, J=14.4 Hz), 5.35 (2H, s), 7.26 (1H, dd, J=2.4, 8.8 Hz), 7.31-7.36 (1H, m), 7.37-7.43 (2H, m), 7.45 (1H, s), 7.49 (1H, s), 7.53-7.58 (2H, m), 7.81 (1H, d, J=8.8 Hz), 8.05 (1H, s), 8.12 (1H, d, J=2.4 Hz)

Step 8 yield: 81.7%

$^1$HNMR (400 MHz, CDCl$_3$) δ: 1.58 (3H, t, J=7.0 Hz), 1.60 (3H, t, J=7.0 Hz), 2.50-2.64 (4H, m), 4.28 (2H, q, J=7.0 Hz), 4.32 (2H, q, J=7.0 Hz), 4.37-4.44 (1H, m), 4.63 (1H, d, J=18.1 Hz), 5.28 (2H, s), 5.67 (1H, d, J=18.1 Hz), 7.30 (1H, s), 7.34 (1H, dd, J=2.7, 9.5 Hz), 7.34-7.39 (1H, m), 7.40-7.45 (2H, m), 7.50-7.55 (2H, m), 7.79 (1H, s), 7.89 (1H, d, J=2.7 Hz), 9.33 (1H, d, J=9.5 Hz)

Step 9 yield: 79.9%

$^1$HNMR (400 MHz, CDCl$_3$) δ: 1.52 (3H, t, J=7.0 Hz), 1.56 (3H, t, J=7.0 Hz), 2.24-2.35 (1H, m), 2.50-2.62 (2H, m), 2.67-2.78 (1H, m), 3.90-3.97 (1H, m), 4.12 (4H, q, J=7.0 Hz), 4.44 (1H, d, J=18.4 Hz), 5.22 (1H, d, J=2.2 Hz), 5.29 (2H, s), 5.30 (1H, d, J=18.4 Hz), 7.07 (1H, s), 7.33 (1H, dd, J=2.4, 9.3 Hz), 7.34-7.37 (1H, m), 7.39-7.45 (2H, m), 7.51-7.56 (2H, m), 7.75 (1H, s), 7.91 (1H, d, J=2.4 Hz), 8.19 (1H, d, J=9.3 Hz)

Step 10 yield: 66.9%

$^1$HNMR (400 MHz, DMSO-d$_6$) δ: 1.41 (3H, t, J=7.0 Hz), 1.44 (3H, t, J=7.0 Hz), 1.73-1.88 (3H, m), 2.09-2.23 (1H, m), 2.26-2.41 (2H, m), 3.20-3.30 (1H, m), 3.39 (1H, d, J=15.6 Hz), 4.17 (2H, dq, J=7.0, 11.7 Hz), 4.30 (2H, q, J=7.0 Hz), 4.45 (1H, d, J=15.6 Hz), 4.64 (1H, d, J=10.0 Hz), 4.90 (1H, dd, J=2.1, 10.0 Hz), 5.35 (2H, s), 7.15 (1H, s), 7.29 (1H, dd, J=2.6, 9.2 Hz), 7.30-7.37 (1H, m), 7.38-7.45 (2H, m), 7.53-7.58 (2H, m), 8.01 (1H, s), 8.10 (1H, d, J=2.6 Hz), 8.21 (1H, d, J=9.2 Hz)

Step 11 yield: 25.5%

$^1$HNMR (400 MHz, DMSO-d$_6$) δ: 1.41 (3H, t, J=7.0 Hz), 1.43 (3H, t, J=7.0 Hz), 1.72-1.87 (3H, m), 2.08-2.23 (1H, m), 2.28-2.42 (2H, m), 3.21-3.34 (1H, m), 3.38 (1H, d, J=15.5 Hz), 4.16 (2H, dq, J=7.0, 11.7 Hz), 4.27 (2H, q, J=7.0 Hz), 4.43 (1H, d, J=15.5 Hz), 4.60 (1H, d, J=8.9 Hz), 4.88 (1H, d, J=8.9 Hz), 7.08 (1H, dd, J=2.2, 8.8 Hz), 7.13 (1H, s), 7.88 (1H, d, J=2.2 Hz), 7.89 (1H, s), 8.11 (1H, d, J=8.8 Hz), 9.60 (1H, s)

Phenanthroindolizidine alkaloid having an alkylcarbonyloxy group at R$^2$ or R$^8$ was synthesized by acylation of phenanthroindolizidine alkaloid having a corresponding hydroxyl group. The synthetic pathway is shown in the following steps 18 and 19.

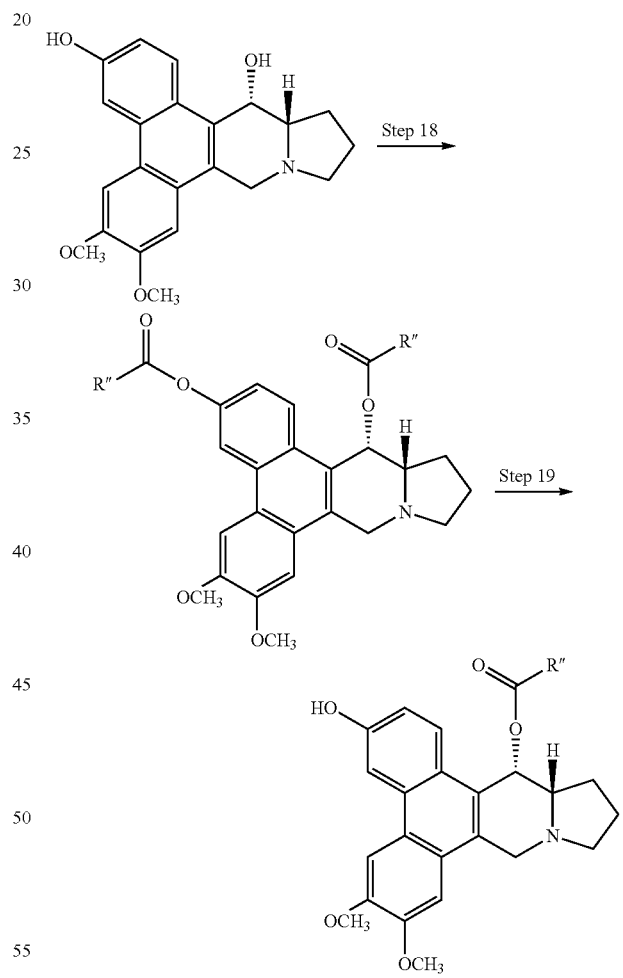

Synthesis Example 8

A compound in which R″ represents CH$_3$, which is obtained through the aforementioned steps 18 and 19, was synthesized. The operation and the yield of each operation are shown below (compound 5).

Step 18: Diacylation of Hydroxyl Groups at R$^2$ and R$^8$

In a 100 mL round-bottom flask, triethylamine (1.4 mL, 40 eq.), anhydrous acetic acid (0.95 mL, 40 eq.), and dimethylaminopyridine (3 mg, 0.1 eq.) were added to a suspension of raw materials (90 mg, 0.25 mmol) in methylene chloride (15 mL) under an argon atmosphere while stirring with cooling on ice, followed by stirring for six hours. The disappearance of the raw materials was confirmed, and then the resulting reaction liquid was concentrated and purified through column chromatography (CHCl$_3$ only) to give 47 mg (41.9%) of a light yellow solid.

$^1$HNMR (400 MHz, DMSO-d$_6$) δ: 1.48-1.77 (2H, m), 1.86-2.12 (2H, m), 2.16 (3H, s), 2.41 (3H, s), 2.40-2.52 (1H, m), 2.67-2.79 (1H, m), 3.50-3.58 (1H, m), 3.66 (1H, d, J=15.38 Hz), 4.07 (3H, s), 4.12 (3H, s), 4.81 (1H, d, J=15.38 Hz), 6.73 (1H, brs), 7.23 (1H, s), 7.31 (1H, dd, J=2.20, 9.03 Hz), 7.89 (1H, s), 7.95 (1H, d, J=9.03 Hz), 8.21 (1H, d, J=2.20 Hz)

99% ee (HPLC analysis condition B), [α]$_D^{29}$+156.9 (c=0.12, CHCl$_3$)

Step 19: Hydrolysis of Phenoxyester

In a 100 mL round-bottom flask, sodium bicarbonate (24 mg, 1.1 eq.) was added to a solution of diacetyl (114 mg, 0.26 mmol) in methanol/tetrahydrofuran/water (1:1:1) (6 mL) while stirring with cooling on ice. The disappearance of the raw materials was confirmed, and then the resulting mixture was extracted with ethyl acetate-hexane. The organic layer was dried over anhydrous magnesium sulfate, followed by removal of the solvent. The residual product was purified through column chromatography (CHCl$_3$ only→CHCl$_3$: MeOH=200:1) to give 83 mg (78.4%) of a yellow solid.

$^1$HNMR (400 MHz, DMSO-d$_6$) δ: 1.43-1.55 (1H, m), 1.74-1.94 (3H, m), 2.04 (3H, s), 2.30-2.40 (1H, m), 2.60-2.69 (1H, m), 3.10-3.40 (1H, m), 3.53 (1H, d, J=15.74 Hz), 3.94 (3H, s), 4.00 (3H, s), 4.67 (1H, d, J=15.74 Hz), 6.50 (1H, brs), 7.08 (1H, dd, J=2.44, 8.79 Hz), 7.27 (1H, s), 7.62 (1H, d, J=8.79 Hz), 7.95 (1H, s), 7.99 (1H, d, J=2.44 Hz) 99% ee (HPLC analysis condition B), [α]$_D^{28}$+172.68 (c=0.11, CH$_3$OH:CHCl$_3$=1:1)

The synthetic method for a compound obtained by reductively removing a hydroxyl group of the compound obtained by the step 9 (a hydroxyl group at the position R$^8$ in the general formula (1) or (2)) will be described. The synthesis was performed in accordance with the steps 20 and 21 shown below.

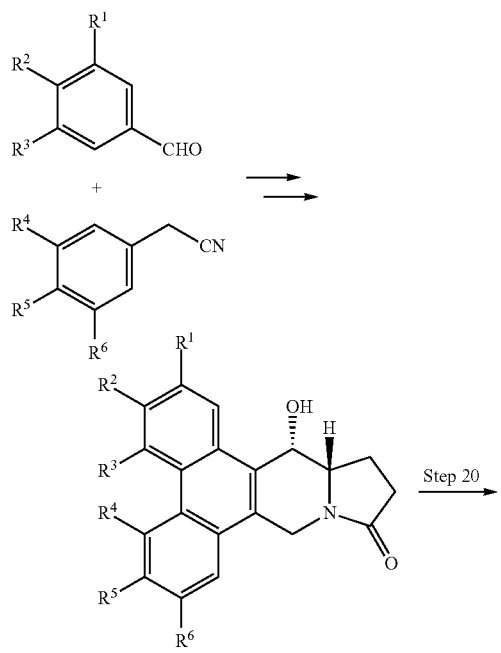

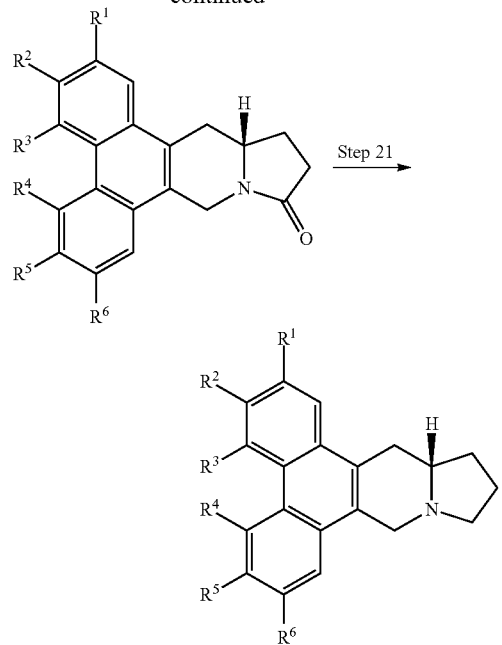

Synthesis Example 9

A compound having the following groups at R$^1$ to R$^6$ was synthesized through steps 20 and 21. The operation and the yield of each operation are shown below.

TABLE 8

| Compound 11 | | | | | |
|---|---|---|---|---|---|
| R$^1$ | R$^2$ | R$^3$ | R$^4$ | R$^5$ | R$^6$ |
| H | OH | H | H | OCH$_3$ | OCH$_3$ |

Step 1 yield: 93%

$^1$H-NMR (400 MHz, CDCl$_3$) δ: 3.93 (3H, s), 3.96 (3H, s), 5.14 (2H, s), 6.92 (1H, d, J=8.3 Hz), 7.03-7.06 (1H, m), 7.13 (1H, d, J=2.2 Hz), 7.24 (1H, dd, J=2.2, 8.3 Hz), 7.35-7.47 (5H, m), 7.36 (1H, s), 7.85-7.88 (1H, m)

Step 2 yield; 69.0%

$^1$H-NMR (400 MHz, CDCl$_3$) δ: 4.10 (3H, s), 4.11 (3H, s), 5.32 (2H, s), 7.28-7.55 (6H, m), 7.58 (1H, s), 7.80 (1H, s), 7.85 (1H, d, J=9.0 Hz), 7.91-7.92 (1H, m), 8.10 (1H, s)

Step 3 yield: 86%

$^1$H-NMR (400 MHz, CDCl$_3$) δ: 4.11 (6H, s), 5.34 (2H, s), 7.34 (1H, dd, J=2.3, 8.8 Hz), 7.38-7.46 (3H, m), 7.54-7.56 (2H, m), 7.81 (1H, s), 7.94 (1H, d, J=2.3 Hz), 7.96 (1H, d, J=8.8 Hz), 8.99 (1H, s), 10.26 (1H, s)

Step 4 yield: 96%

$^1$H-NMR (400 MHz, CDCl$_3$) δ: 4.07 (3H, s), 4.10 (3H, s), 5.12 (2H, d, J=5.9 Hz), 5.29 (2H, s), 7.25-7.29 (1H, m), 7.36-7.38 (1H, m), 7.41-7.45 (2H, m), 7.52-7.55 (2H, m), 7.57 (1H, m), 7.62 (1H, s), 7.79 (1H, d, J=8.8 Hz), 7.86 (1H, s), 7.94 (1H, d, J=2.2 Hz)

Steps 5 and 6
  yield: 79%, 99.6% ee (HPLC condition A)
  $^1$H-NMR (400 MHz, CDCl$_3$) δ: 1.19 (6H, t, J=5.9 Hz), 1.92-2.64 (4H, m), 3.72 (1H, dd, J=3.7, 9.0 Hz), 4.04 (3H, s), 4.09 (3H, s), 4.31 (1H, d, J=14.6 Hz), 4.98-5.04 (1H, m), 5.29 (2H, s), 5.60 (1H, d, J=14.6 Hz), 7.25-7.28 (1H, m), 7.34-7.45 (4H, m), 7.53-7.55 (2H, m), 7.60 (1H, s), 7.72 (1H, d, J=8.8 Hz), 7.83 (1H, s), 7.92-7.93 (1H, m)
<Enantiomer>
  yield: 99%, [α]$_D$$^{32}$-55.2° (c=0.1, CHCl$_3$)
Step 7
  yield: 99%
  $^1$H-NMR (400 MHz, CDCl$_3$) δ: 2.00-2.65 (4H, m), 3.84-3.88 (1H, m), 4.04 (3H, s), 4.09 (3H, s), 4.33 (1H, d, J=14.4 Hz), 5.27 (2H, s), 5.64 (1H, d, J=14.4 Hz), 7.24-7.54 (7H, m), 7.61 (1H, s), 7.76 (1H, d, J=8.8 Hz), 7.83 (1H, s), 7.92-7.93 (1H, m)
Step 8
  yield: 60%, 100% ee (HPLC condition B)
  $^1$H-NMR (400 MHz, CDCl$_3$) δ: 2.52-2.63 (4H, m), 4.08 (3H, s), 4.12 (3H, s), 4.41-4.44 (1H, m), 4.67 (1H, d, J=8.1 Hz), 5.30 (2H, s), 5.71 (1H, d, J=18.1 Hz), 7.30 (1H, s), 7.35-7.45 (4H, m), 7.53-7.55 (2H, m), 7.80 (1H, s), 7.93 (1H, d, J=2.4 Hz), 9.35 (1H, d, J=9.3 Hz)
<Enantiomer>
  yield: 39%, [α]$_D$$^{32}$-94.0° (c=0.06, CHCl$_3$)
Step 9
  yield: 74%
  $^1$H-NMR (400 MHz, CDCl$_3$) δ: 2.30-2.76 (4H, m), 3.97-4.02 (1H, m), 4.02 (3H, s), 4.10 (3H, s), 4.52 (1H, d, J=17.6 Hz), 5.25-5.27 (1H, m), 5.31 (2H, s), 5.41 (1H, d, J=17.6 Hz), 7.35-7.45 (5H, m), 7.52-7.55 (2H, m), 7.82 (1H, s), 7.98 (1H, d, J=2.4 Hz), 8.21 (1H, d, J=9.3 Hz)
<Enantiomer>
  yield: 48%, [α]$_D$$^{32}$-94.0° (c=0.1, CHCl$_3$)
Step 20: Reductive Removal of a Hydroxyl Group
  In a round-bottom flask, 293 μL (2.31 mmol, 1.5 eq.) of a boron trifluoride.diethyl ether complex was added to a solution of 719 mg (1.54 mmol) of alcohol in 10 mL of methylene chloride at 0° C. under an argon atmosphere. After five minutes, 984 μL (6.16 mmol, 4.0 eq.) of triethylsilane was added. After four hours, the disappearance of the raw materials was confirmed, and a solution of chloroform-methanol=4:1 was added to give a complete solution. And then, the organic layer was separated and the aqueous layer was extracted with a solution of chloroform-methanol=4:1. The organic layer was combined and the resulting mixture was dried over magnesium sulfate. The solvent was then removed under reduced pressure, and the residual product was purified through column chromatography (chloroform-methanol=50:1) to give 516 mg (74%) of a white solid. [α]$_D$$^{30}$+185.34 (c=0.1, CHCl$_3$)
  $^1$HNMR (400 MHz, CDCl$_3$) δ: 1.92-2.08 (1H, m), 2.48-2.68 (3H, m), 2.89 (1H, dd, J=11.0, 16.0 Hz), 3.58 (1H, dd, J=4.2, 16.0 Hz), 3.88-4.03 (1H, m), 4.06 (3H, s), 4.09 (3H, s), 4.57 (1H, d, J=17.5 Hz), 5.30 (2H, s), 5.33 (1H, d, J=17.5 Hz), 7.19 (1H, s), 7.31 (1H, dd, J=2.6, 9.2 Hz), 7.33-7.38 (1H, m), 7.38-7.46 (2H, m), 7.51-7.58 (2H, m), 7.85 (1H, s), 7.93 (1H, d, J=9.2 Hz), 7.99 (1H, d, J=2.6 Hz)
<Enantiomer>
  [α]$_D$$^{27}$-196.52 (c=0.1, CHCl$_3$)
Step 21: Reduction of Lactam (the Operation was Similar to that of the Step 10)
  yield: 74%, [α]$_D$$^{30}$+90.40 (c=0.1, CHCl$_3$)
  $^1$HNMR (400 MHz, DMSO-d$_6$) δ: 1.53-1.70 (1H, m), 1.75-1.94 (2H, m), 2.07-2.23 (1H, m), 2.26-2.44 (2H, m), 2.71-2.83 (1H, m), 3.26-3.42 (2H, m), 3.52 (1H, d, J=15.1 Hz), 3.93 (3H, s), 4.01 (3H, s), 4.55 (1H, d, J=15.1 Hz), 5.35 (2H, s), 7.20 (1H, s), 7.30 (1H, dd, J=2.4, 9.0 Hz), 7.32-7.37 (1H, m), 7.39-7.46 (2H, m), 7.52-7.61 (2H, m), 7.93 (1H, d, J=9.0 Hz), 8.17 (1H, d, J=2.4 Hz)
  The specific optical rotation of the enantiomer (compound 12) [α]$_D$$^{29}$-103.88 (c=0.1, CHCl$_3$)

Synthesis Example 10

A compound having the following groups at R$^1$ to R$^6$ was synthesized through steps 20 and 21, and by deprotection in step 11. The operation and the yield of each operation are shown below.

TABLE 9

| Compound 13 | | | | | |
| --- | --- | --- | --- | --- | --- |
| R$^1$ | R$^2$ | R$^3$ | R$^4$ | R$^5$ | R$^6$ |
| H | OH | H | H | —OCH$_2$O— | |

Step 20
  yield: 63.8%
  $^1$HNMR (400 MHz, CDCl$_3$) δ: 1.92-2.08 (1H, m), 2.48-2.68 (3H, m), 2.86 (1H, dd, J=11.0, 15.6 Hz), 3.54 (1H, dd, J=4.2, 15.6 Hz), 3.88-4.03 (1H, m), 4.49 (1H, d, J=17.3 Hz), 5.27 (1H, d, J=17.3 Hz), 5.28 (2H, s), 6.12 (2H, q, J=1.2 Hz), 7.28 (1H, s), 7.30 (1H, dd, J=2.7, 9.0 Hz), 7.33-7.38 (1H, m), 7.38-7.46 (2H, m), 7.51-7.58 (2H, m), 7.91 (1H, s), 7.91 (1H, d, J=9.0 Hz), 7.93 (1H, d, J=2.7 Hz)
Step 21
  yield: 95.6%
  $^1$HNMR (400 MHz, DMSO-d$_6$) δ: 1.53-1.70 (1H, m), 1.75-1.94 (2H, m), 2.07-2.23 (1H, m), 2.26-2.44 (2H, m), 2.71-2.83 (1H, m), 3.26-3.42 (2H, m), 3.47 (1H, d, J=15.0 Hz), 4.46 (1H, d, J=15.0 Hz), 5.35 (2H, s), 6.17 (2H, d, J=0.73 Hz), 7.28 (1H, dd, J=2.4, 9.0 Hz), 7.32-7.37 (1H, m), 7.32 (1H, s), 7.39-7.46 (2H, m), 7.52-7.61 (2H, m), 7.92 (1H, d, J=9.0 Hz), 8.17 (1H, d, J=2.4 Hz), 8.33 (1H, s)
Step 11
  yield: 85.9%
  $^1$HNMR (400 MHz, DMSO-d$_6$) δ: 1.52-1.68 (1H, m), 1.75-1.94 (2H, m), 2.07-2.23 (1H, m), 2.26-2.44 (2H, m), 2.71-2.83 (1H, m), 3.26-3.42 (2H, m), 3.44 (1H, d, J=15.0 Hz), 4.44 (1H, d, J=15.0 Hz), 6.15 (2H, s), 7.10 (1H, dd, J=2.4, 8.8 Hz), 7.29 (1H, s), 7.83 (1H, d, J=8.8 Hz), 7.84 (1H, d, J=2.4 Hz), 8.00 (1H, s), 9.67 (1H, s)

Synthesis Example 11

A compound having the following groups at R$^1$ to R$^6$ was synthesized through steps 20 and 21, and by deprotection in step 11. The operation and the yield of each operation are shown below.

TABLE 10

| Compound 14 | | | | | |
| --- | --- | --- | --- | --- | --- |
| R$^1$ | R$^2$ | R$^3$ | R$^4$ | R$^5$ | R$^6$ |
| H | OH | H | H | CH$_3$CH$_2$O | CH$_3$CH$_2$O |

Step 20
  yield: 53.5%
  $^1$HNMR (400 MHz, CDCl$_3$) δ: 1.56 (3H, t, J=7.1 Hz), 1.58 (3H, t, J=7.1 Hz), 1.97-2.12 (1H, m), 2.48-2.68 (3H, m), 2.88

(1H, dd, J=10.74, 15.9 Hz), 3.53 (1H, dd, J=4.2, 15.9 Hz), 4.21-4.36 (1H, m), 4.27 (2H, q, J=7.1 Hz), 4.30 (2H, q, J=7.1 Hz), 4.55 (1H, d, J=16.8 Hz), 5.29 (2H, s), 5.31 (1H, d, J=16.8 Hz), 7.21 (1H, s), 7.29 (1H, dd, J=2.4, 9.0 Hz), 7.33-7.39 (1H, m), 7.38-7.46 (2H, m), 7.51-7.57 (2H, m), 7.88 (1H, s), 7.92 (1H, d, J=9.0 Hz), 7.97 (1H, d, J=2.4 Hz)

Steps 21 and 11 yield: 52.6%

$^1$HNMR (400 MHz, DMSO-$d_6$) δ: 1.41 (3H, t, J=7.0 Hz), 1.43 (3H, q, J=7.0 Hz), 1.51-1.68 (1H, m), 1.75-1.94 (2H, m), 2.07-2.23 (1H, m), 2.32-2.40 (2H, m), 2.68-2.83 (1H, m), 3.26-3.42 (2H, m), 3.48 (1H, d, J=15.0 Hz), 4.19 (2H, dq, J=7.0, 10.0 Hz), 4.26 (2H, q, J=7.0 Hz), 4.50 (1H, d, J=15.0 Hz), 7.08 (1H, dd, J=2.3, 8.9 Hz), 7.17 (1H, s), 7.83 (1H, t, J=8.9 Hz), 7.90 (1H, d, J=2.3 Hz), 7.91 (1H, s), 9.64 (1H, s)

Synthesis Example 12

A compound having the following groups at $R^1$ to $R^6$ was synthesized. The operation and the yield of each operation are shown below.

TABLE 11

| Compound 21 | | | | | |
|---|---|---|---|---|---|
| $R^1$ | $R^2$ | $R^3$ | $R^4$ | $R^5$ | $R^6$ |
| Cl | OH | H | H | $OCH_3$ | $OCH_3$ |

TABLE 12

| Compound 22 | | | | | |
|---|---|---|---|---|---|
| $R^1$ | $R^2$ | $R^3$ | $R^4$ | $R^5$ | $R^6$ |
| H | OH | Cl | H | $OCH_3$ | $OCH_3$ |

Step 1 yield: 90.5%

$^1$HNMR (400 MHz, CDCl$_3$) δ: 3.93 (3H, s), 3.96 (3H, s), 5.24 (2H, s), 6.91 (1H, d, J=8.3 Hz), 7.50 (1H, d, J=9.3 Hz), 7.11 (1H, d, J=2.4 Hz), 7.23 (1H, dd, J=2.4, 8.3 Hz), 7.28 (1H, s), 7.32-7.50 (5H, m), 7.81-7.89 (2H, m)

Step 2 yield: 96.4%

A mixture of regioisomers with respect to the chlorine atom on the aromatic ring was isolated.

Step 3 yield: 86.3%

A mixture of regioisomers with respect to the chlorine atom on the aromatic ring was isolated.

Step 4 yield: 92.5%

A mixture of regioisomers with respect to the chlorine atom on the aromatic ring was isolated.

Steps 5 and 6 yield: 64.4%

A mixture of regioisomers with respect to the chlorine atom on the aromatic ring was isolated.

Step 7 yield: 72.4%

A mixture of regioisomers with respect to the chlorine atom on the aromatic ring was isolated.

Step 8

$R^1$=Cl, $R^3$=H (a derivative of compound 21)

yield: 31.6%

$^1$HNMR (400 MHz, CDCl$_3$) δ: 2.50-2.68 (4H, m), 4.08 (3H, s), 4.11 (3H, s), 4.40-4.47 (1H, m), 4.69 (1H, d, J=18.4 Hz), 5.41 (2H, s), 5.73 (1H, d, J=18.4 Hz), 7.32 (1H, s), 7.33-7.46 (3H, m), 7.55-7.60 (2H, m), 7.61 (1H, s), 7.83 (1H, s), 9.56 (1H, s)

$R^1$=H, $R^3$=Cl (a derivative of compound 22)

yield: 29.2%

$^1$HNMR (400 MHz, CDCl$_3$) δ: 2.50-2.68 (4H, m), 4.10 (3H, s), 4.12 (3H, s), 4.40-4.47 (1H, m), 4.68 (1H, d, J=17.8 Hz), 5.35 (2H, s), 5.72 (1H, d, J=17.8 Hz), 7.30-7.46 (5H, m), 7.52-7.57 (2H, m), 9.21-9.26 (2H, m)

Steps 9 and 20

$R^1$=Cl, $R^3$=H yield: 85.6%

$^1$HNMR (400 MHz, CDCl$_3$) δ: 1.90-2.05 (1H, m), 2.49-2.65 (3H, m), 2.72-2.83 (1H, m), 3.40-3.48 (1H, m), 3.84-3.96 (1H, m), 4.03 (3H, s), 4.08 (3H, s), 4.48 (1H, d, J=17.3 Hz), 5.26 (1H, d, J=17.3 Hz), 5.38 (2H, s), 7.11 (1H, s), 7.31-7.46 (3H, m), 7.55-7.61 (2H, m), 7.64 (1H, s), 7.96 (1H, s)

$R^1$=H, $R^3$=Cl yield: 95.3%

$^1$HNMR (400 MHz, CDCl$_3$) δ: 1.94-2.08 (1H, m), 2.50-2.63 (3H, m), 2.82-2.94 (1H, m), 3.42-3.51 (1H, m), 3.86-3.98 (1H, m), 4.07 (3H, s), 4.09 (3H, s), 4.55 (1H, d, J=17.3 Hz), 5.32 (1H, d, J=17.3 Hz), 5.33 (2H, s), 7.20 (1H, s), 7.30-7.46 (4H, m), 7.50-7.57 (2H, m), 7.88 (1H, d, J=9.0 Hz), 9.43 (1H, s)

Step 21

$R^1$=Cl, $R^3$=H yield: 80.3%

$^1$HNMR (400 MHz, DMSO-$d_6$) δ: 1.55-1.70 (1H, m), 1.74-1.92 (2H, m), 2.07-2.21 (1H, m), 2.29-2.41 (2H, m), 2.70-2.82 (1H, m), 3.25-3.36 (2H, m), 3.52 (1H, d, J=15.1 Hz), 3.94 (3H, s), 4.04 (3H, s), 4.56 (1H, d, J=15.1 Hz), 5.51 (2H, s), 7.21 (1H, s), 7.31-7.46 (3H, m), 7.55-7.64 (2H, m), 8.01 (1H, s), 8.02 (1H, s), 8.26 (1H, s)

$R^1$=H, $R^3$=Cl yield: 60.1%

$^1$HNMR (400 MHz, DMSO-$d_6$) δ: 1.55-1.70 (1H, m), 1.74-1.92 (2H, m), 2.07-2.21 (1H, m), 2.29-2.41 (2H, m), 2.70-2.86 (1H, m), 3.25-3.36 (2H, m), 3.55 (1H, d, J=15.6 Hz), 3.93 (3H, s), 3.96 (3H, s), 4.54 (1H, d, J=15.6 Hz), 5.38 (2H, s), 7.24 (1H, s), 7.32-7.46 (3H, m), 7.52-7.64 (3H, m), 8.02 (1H, d, J=9.0 Hz), 9.26 (1H, s)

Step 11 Deprotection of a Benzyl Group $R^1$=Cl, $R^3$=H (compound 21)

yield: 48.2%

$^1$HNMR (400 MHz, DMSO-$d_6$) δ: 1.55-1.70 (1H, m), 1.74-1.93 (2H, m), 2.07-2.21 (1H, m), 2.29-2.41 (2H, m), 2.70-2.82 (1H, m), 3.25-3.36 (2H, m), 3.52 (1H, d, J=15.1 Hz), 3.94 (3H, s), 4.04 (3H, s), 4.56 (1H, d, J=15.1 Hz), 5.51 (2H, s), 7.21 (1H, s), 8.01 (1H, s), 8.02 (1H, s), 8.26 (1H, s)

$R^1$=H, $R^3$=Cl (compound 22)

yield: 56.7%

$^1$HNMR (400 MHz, DMSO-$d_6$) δ: 1.55-1.70 (1H, m), 1.76-1.92 (2H, m), 2.08-2.21 (1H, m), 2.30-2.40 (2H, m), 2.71-2.83 (1H, m), 3.22-3.41 (2H, m), 3.52 (1H, d, J=15.1 Hz), 3.92 (3H, s), 3.95 (3H, s), 4.52 (1H, d, J=15.1 Hz), 7.21 (1H, s), 7.30 (1H, d, J=9.0 Hz), 7.87 (1H, d, J=9.0 Hz), 9.26 (1H, s)

Synthesis Example 13

A compound having the following groups at $R^1$ to $R^6$ was synthesized. The operation and the yield of each operation are shown below.

TABLE 13

| Compound 23 | | | | | |
|---|---|---|---|---|---|
| $R^1$ | $R^2$ | $R^3$ | $R^4$ | $R^5$ | $R^6$ |
| Cl | OH | Cl | H | $OCH_3$ | $OCH_3$ |

Step 1
 yield: 86.9%
 $^1$HNMR (400 MHz, CDCl$_3$) δ: 3.94 (3H, s), 3.96 (3H, s), 5.11 (2H, s), 6.93 (1H, d, J=8.6 Hz), 7.12 (1H, d, J=2.2 Hz), 7.26 (1H, s), 726 (1H, dd, J=2.2, 8.6 Hz), 7.35-7.46 (3H, m), 7.54-7.60 (2H, m), 7.84 (2H, m)

Step 2
 yield: 89.1%
 $^1$HNMR (400 MHz, CDCl$_3$) δ: 4.11 (3H, s), 4.12 (3H, s), 5.19 (2H, s), 7.35-7.49 (3H, m), 7.63 (1H, s), 7.63-7.67 (2H, m), 7.92 (1H, s), 8.00 (1H, s), 9.43 (1H, s)

Step 3
 yield: 84.4%
 $^1$HNMR (400 MHz, CDCl$_3$) δ: 4.11 (3H, s), 4.12 (3H, s), 5.21 (2H, s), 7.38-7.51 (3H, m), 7.62-7.71 (2H, m), 8.00 (1H, s), 8.04 (1H, s), 8.99 (1H, s), 9.40 (1H, s), 10.29 (1H, s)

Step 4
 yield: 94.0%
 $^1$HNMR (400 MHz, CDCl$_3$) δ: 4.07 (3H, s), 4.09 (3H, s), 5.13 (2H, s), 5.15 (2H, s), 7.36-7.51 (3H, m), 7.51 (1H, s), 7.54 (1H, s), 7.62-7.70 (2H, m), 7.83 (1H, s), 9.43 (1H, s)

Steps 5 and 6
 yield: 57.3%
 $^1$HNMR (400 MHz, CDCl$_3$) δ: 1.19 (3H, d, J=6.4 Hz), 1.20 (3H, d, J=6.4 Hz), 1.93-2.20 (2H, m), 2.34-2.44 (1H, m), 2.54-2.67 (1H, m), 3.72 (1H, dd, J=3.5, 9.1 Hz), 4.06 (3H, s), 4.10 (3H, s), 4.35 (1H, d, J=14.6 Hz), 5.00 (1H, heptet, J=6.4 Hz), 5.17 (2H, s), 5.59 (1H, d, J=14.6 Hz), 7.35 (1H, s), 7.37-7.48 (3H, m), 7.65 (1H, s), 7.63-7.69 (2H, m), 7.80 (1H, s), 9.43 (1H, s)

Step 7
 yield: 77.9%
 $^1$HNMR (400 MHz, DMSO-d$_6$) δ: 1.86-1.96 (1H, m), 2.17-2.28 (1H, m), 2.30-2.48 (2H, m), 3.77 (1H, dd, J=2.9, 9.2 Hz), 3.92 (3H, s), 3.97 (3H, s), 4.33 (1H, d, J=15.0 Hz), 5.12 (2H, s), 5.36 (1H, d, J=15.0 Hz), 7.37-7.48 (3H, m), 7.56-7.65 (4H, m), 8.23 (1H, s), 9.31 (1H, s)

Step 8
 yield: 75.1%
 $^1$HNMR (400 MHz, CDCl$_3$) δ: 2.51-2.67 (4H, m), 4.11 (3H, s), 4.12 (3H, s), 4.42-4.48 (1H, m), 4.71 (1H, d, J=18.1 Hz), 5.13-5.24 (2H, m), 5.75 (1H, d, J=18.1 Hz), 7.36 (1H, s), 7.34-7.48 (3H, m), 9.13 (1H, s), 9.47 (1H, s)

Steps 9 and 20
 yield: 52.6%
 $^1$HNMR (400 MHz, CDCl$_3$) δ: 1.98-2.11 (1H, m), 2.52-2.68 (3H, m), 2.83-2.96 (1H, m), 3.42-3.50 (1H, m), 3.88-3.99 (1H, m), 4.08 (3H, s), 4.09 (3H, s), 4.57 (1H, d, J=17.6 Hz), 5.18 (2H, s), 5.36 (1H, d, J=17.6 Hz), 7.23 (1H, s), 7.34-7.48 (3H, m), 7.62-7.69 (2H, m), 8.02 (1H, s), 9.31 (1H, s)

Step 21
 yield: 58.6%
 $^1$HNMR (400 MHz, DMSO-d$_6$) δ: 1.58-1.70 (1H, m), 1.76-1.95 (2H, m), 2.08-2.23 (1H, m), 2.30-2.41 (2H, m), 2.75-2.87 (1H, m), 3.28-3.42 (1H, m), 3.58 (1H, d, J=16.1 Hz), 3.95 (3H, s), 3.97 (3H, s), 4.59 (1H, d, J=16.1 Hz), 5.08-5.19 (2H, m), 7.29 (1H, s), 7.38-7.49 (3H, m), 7.59-7.65 (2H, m), 8.15 (1H, s), 9.17 (1H, s)

Step 11
 yield: 66.7%
 $^1$HNMR (400 MHz, DMSO-d$_6$) δ: 1.56-1.72 (1H, m), 1.75-1.93 (2H, m), 2.07-2.22 (1H, m), 2.29-2.40 (2H, m), 2.70-2.81 (1H, m), 3.22-3.40 (2H, m), 3.52 (1H, d, J=15.1 Hz), 3.92 (3H, s), 3.94 (3H, s), 4.51 (1H, d, J=15.1 Hz), 7.20 (1H, s), 7.95 (1H, s), 9.16 (1H, s)

Synthesis Example 14

Compounds having the following groups at $R^1$ to $R^6$ were each synthesized. The operation and the yield of each operation are shown below.

TABLE 14

| Compound 25 | | | | | |
|---|---|---|---|---|---|
| $R^1$ | $R^2$ | $R^3$ | $R^4$ | $R^5$ | $R^6$ |
| F | OH | H | H | $OCH_3$ | $OCH_3$ |

TABLE 15

| Compound 24 | | | | | |
|---|---|---|---|---|---|
| $R^1$ | $R^2$ | $R^3$ | $R^4$ | $R^5$ | $R^6$ |
| H | OH | F | H | $OCH_3$ | $OCH_3$ |

Step 1
 yield: 77.6%
 $^1$HNMR (400 MHz, CDCl$_3$) δ: 3.93 (3H, s), 3.95 (3H, s), 5.21 (2H, s), 6.91 (1H, d, J=8.6 Hz), 7.02-7.08 (1H, m), 7.11 (1H, d, J=2.2 Hz), 7.23 (1H, dd, J=2.2, 8.6 Hz), 7.29 (1H, s), 7.32-7.49 (5H, m), 7.56-7.64 (1H, m), 7.66-7.73 (1H, m)

Step 2
 yield: 55.6%
 A mixture of regioisomers with respect to the fluorine atom was isolated.

Step 3
 yield: quant.
 A mixture of regioisomers with respect to the fluorine atom was isolated.

Step 4
 yield: 99.0%
 A mixture of regioisomers with respect to the fluorine atom was isolated.

Steps 5 and 6
 $R^1$=F, $R^3$=H
 yield: 58.2%
 $^1$HNMR (400 MHz, CDCl$_3$) δ: 1.18 (3H, d, J=6.1 Hz), 1.20 (3H, d, J=6.1 Hz), 1.91-2.01 (1H, m), 2.02-2.15 (1H, m), 2.31-2.44 (1H, m), 2.52-2.64 (1H, m), 3.70 (1H, dd, J=3.8, 9.2 Hz), 4.03 (3H, s), 4.08 (3H, s), 4.32 (1H, d, J=14.4 Hz), 5.00 (1H, heptet, J=6.1 Hz), 5.38 (2H, s), 5.58 (1H, d, J=14.4 Hz), 7.33-7.48 (5H, m), 7.60 (1H, s), 7.65 (1H, s), 7.91 (1H, d, J=8.0 Hz)

$R^1$=H, $R^3$=F
 yield: 53.2%
 $^1$HNMR (400 MHz, CDCl$_3$) δ: 1.17 (6H, d, J=6.4 Hz), 1.91-2.01 (1H, m), 2.02-2.15 (1H, m), 2.31-2.44 (1H, m), 2.52-2.64 (1H, m), 3.72 (1H, dd, J=3.7, 9.3 Hz), 4.04 (3H, s), 4.08 (3H, s), 4.32 (1H, d, J=14.4 Hz), 4.99 (1H, heptet, J=6.4 Hz), 5.30 (2H, s), 5.58 (1H, d, J=14.4 Hz), 7.28-7.45 (5H, m), 7.47-7.57 (3H, m), 7.62 (1H, s), 8.62 (1H, d, J=6.3 Hz)

Step 7
$R^1$=F, $R^3$=H
yield: 96.8%
$^1$HNMR (400 MHz, DMSO-$d_6$) δ: 1.81-1.95 (1H, m), 2.01-2.18 (1H, m), 2.26-2.43 (2H, m), 3.58-3.67 (1H, m), 3.89 (3H, s), 3.93 (3H, s), 4.26 (1H, d, J=14.6 Hz), 5.33 (2H, s), 5.36 (1H, d, J=14.6 Hz), 7.31-7.44 (3H, m), 7.49-7.63 (5H, m), 7.72 (1H, d, J=9.0 Hz), 8.44 (1H, d, J=5.9 Hz)

$R^1$=H, $R^3$=F
yield: 85.8%
$^1$HNMR (400 MHz, DMSO-$d_6$) δ: 1.81-1.93 (1H, m), 2.03-2.18 (1H, m), 2.28-2.43 (2H, m), 3.60-3.71 (1H, m), 3.87 (3H, s), 4.04 (3H, s), 4.23 (1H, d, J=14.8 Hz), 5.35 (1H, d, J=14.8 Hz), 5.47 (2H, s), 7.31-7.47 (4H, m), 7.52 (1H, s), 7.56-7.62 (2H, m), 7.76 (1H, d, J=12.0 Hz), 8.03 (1H, s), 8.27-8.33 (1H, m)

Step 8
$R^1$=F, $R^3$=H
yield: 27.2%
$^1$HNMR (400 MHz, CDCl$_3$) δ: 2.50-2.67 (4H, m), 4.08 (3H, s), 4.10 (3H, s), 4.37-4.47 (1H, m), 4.69 (1H, d, J=17.8 Hz), 5.39 (2H, s), 5.73 (1H, d, J=17.8 Hz), 7.30 (1H, s), 7.33-7.46 (3H, m), 7.53-7.58 (2H, m), 7.60 (1H, s), 7.88 (1H, d, J=8.1 Hz), 9.28 (1H, d, J=15.1 Hz)

$R^1$=H, $R^3$=F
yield: 31.2%
$^1$HNMR (400 MHz, CDCl$_3$) δ: 2.50-2.67 (4H, m), 4.10 (3H, s), 4.11 (3H, s), 4.40-4.47 (1H, m), 4.70 (1H, d, J=17.9 Hz), 5.32 (2H, s), 5.74 (1H, d, J=17.9 Hz), 7.32-7.46 (5H, m), 7.50-7.58 (2H, m), 8.65 (1H, d, J=7.3 Hz), 9.12 (1H, dd, J=1.8, 9.4 Hz)

Steps 9, 20, 21, and 11
$R^1$=F, $R^3$=H
yield: 47.3%
$^1$HNMR (400 MHz, DMSO-$d_6$) δ: 1.54-1.68 (1H, m), 1.74-1.94 (2H, m), 2.06-2.21 (1H, m), 2.28-2.41 (2H, m), 2.64-2.78 (1H, m), 3.26-3.42 (2H, m), 3.51 (1H, d, J=15.2 Hz), 3.92 (3H, s), 3.97 (3H, s), 4.54 (1H, d, J=15.2 Hz), 7.19 (1H, s), 7.67 (1H, d, J=13.4 Hz), 7.85 (1H, s), 8.14 (1H, d, J=9.0 Hz), 10.20 (1H, brs)

$R^1$=H, $R^3$=F
yield: 47.3%
$^1$HNMR (400 MHz, DMSO-$d_6$) δ: 1.54-1.70 (1H, m), 1.74-1.94 (2H, m), 2.09-2.21 (1H, m), 2.26-2.43 (2H, m), 2.69-2.81 (1H, m), 3.26-3.42 (2H, m), 3.53 (1H, d, J=15.1 Hz), 3.92 (3H, s), 3.95 (3H, s), 4.55 (1H, d, J=15.1 Hz), 7.24 (1H, s), 7.27 (1H, dd, J=8.8, 8.9 Hz), 7.70 (1H, d, J=8.9 Hz), 8.44 (1H, d, J=6.1 Hz), 9.97 (1H, brs)

Synthesis Example 15

A compound having the following groups at $R^1$ to $R^6$ was synthesized. The operation and the yield of each operation are shown below.

TABLE 16

| Compound 26 | | | | | |
| --- | --- | --- | --- | --- | --- |
| $R^1$ | $R^2$ | $R^3$ | $R^4$ | $R^5$ | $R^6$ |
| CH$_3$ | OH | CH$_3$ | H | OCH$_3$ | OCH$_3$ |

Step 1
yield: 92%
$^1$HNMR (400 MHz, CDCl$_3$) δ: 2.35 (6H, s), 3.93 (3H, s), 3.96 (3H, s), 4.87 (2H, s), 6.92 (1H, d, J=8.0 Hz), 7.13 (1H, d, J=2.4 Hz), 7.24 (1H, dd, J=2.4, 8.0 Hz), 7.31-7.51 (6H, m), 7.59 (2H, s)

Step 2
yield: 47%
$^1$HNMR (400 MHz, CDCl$_3$) δ: 2.50 (3H, s), 3.03 (3H, s), 4.09 (3H, s), 4.11 (3H, s), 4.99 (2H, s), 7.37-7.49 (3H, m), 7.52-7.56 (2H, m), 7.63 (1H, s), 7.64 (1H, s), 8.04 (1H, s), 8.27 (1H, s)

Step 3
yield: quant
$^1$HNMR (400 MHz, CDCl$_3$) δ: 2.52 (3H, s), 3.03 (3H, s), 4.08 (3H, s), 4.12 (3H, s), 5.02 (2H, s), 7.37-7.49 (3H, m), 7.52-7.59 (2H, m), 7.75 (1H, s), 8.05 (1H, s), 8.22 (1H, s), 9.03 (1H, s), 10.26 (1H, s)

Step 4
yield: 93.8%
$^1$HNMR (400 MHz, CDCl$_3$) δ: 2.50 (3H, s), 3.05 (3H, s), 4.08 (6H, s), 4.98 (2H, s), 5.13 (2H, s), 7.37-7.49 (3H, m), 7.52-7.59 (4H, m), 7.60 (1H, s), 8.29 (1H, s)

Steps 5 and 6
yield: 69.3%
$^1$HNMR (400 MHz, CDCl$_3$) δ: 1.20 (3H, d, J=6.2 Hz), 1.20 (3H, d, J=6.2 Hz), 1.91-2.01 (1H, m), 2.05-2.14 (1H, m), 2.32-2.44 (1H, m), 2.49 (3H, s), 2.53-2.67 (1H, m), 3.04 (3H, s), 3.70-3.76 (1H, m), 4.05 (3H, s), 4.07 (3H, s), 4.30 (1H, d, J=14.5 Hz), 4.99 (2H, s), 5.02 (1H, heptet, J=6.2 Hz), 5.63 (1H, d, J=14.5 Hz), 7.36-7.48 (4H, m), 7.51 (1H, s), 7.52-7.59 (2H, m), 7.64 (1H, s), 8.27 (1H, s)

Step 7
yield: 82.6%
$^1$HNMR (400 MHz, DMSO-$d_6$) δ: 1.81-1.93 (1H, m), 2.08-2.20 (1H, m), 2.27-2.45 (2H, m), 2.42 (3H, s), 3.01 (3H, s), 3.61-3.68 (1H, m), 3.88 (3H, s), 3.97 (3H, s), 4.23 (1H, d, J=14.9 Hz), 4.92-5.00 (2H, m), 5.41 (1H, d, J=14.9 Hz), 7.35-7.48 (4H, m), 7.54 (1H, s), 7.55-7.61 (2H, m), 7.63 (1H, s), 8.25 (1H, s)

Step 8
yield: 51.3%
$^1$HNMR (400 MHz, CDCl$_3$) δ: 2.50 (3H, s), 2.50-2.65 (4H, m), 2.88 (3H, s), 4.08 (3H, s), 4.09 (3H, s), 4.41-4.48 (1H, m), 4.68 (1H, d, J=17.7 Hz), 5.12 (1H, s), 5.71 (1H, d, J=17.7 Hz), 7.33 (1H, s), 7.94 (1H, s), 9.02 (1H, s)

Steps 9 and 20
yield: 60.7%
$^1$HNMR (400 MHz, CDCl$_3$) δ: 1.90-2.08 (1H, m), 2.50 (3H, s), 2.50-2.65 (3H, m), 2.82-2.92 (1H, m), 2.93 (3H, s), 3.48-3.57 (1H, m), 3.89-3.96 (1H, m), 4.05 (3H, s), 4.06 (3H, s), 4.57 (1H, d, J=17.0 Hz), 5.05 (1H, s), 5.31 (1H, d, J=17.0 Hz), 7.22 (1H, s), 7.66 (1H, s), 8.05 (1H, s)

Step 21
yield: 46.7%
$^1$HNMR (400 MHz, DMSO-$d_6$) δ: 1.55-1.68 (1H, m), 1.75-1.92 (2H, m), 2.10-2.20 (1H, m), 2.28-2.39 (2H, m), 2.39 (3H, s), 2.65-2.78 (1H, m), 2.83 (3H, s), 3.25-3.34 (1H, m), 3.51 (1H, d, J=15.4 Hz), 3.92 (3H, s), 3.92 (3H, s), 4.06-4.13 (1H, m), 4.49 (1H, d, J=15.4 Hz), 7.18 (1H, s), 7.63 (1H, s), 8.02 (1H, s), 8.58 (1H, s)

Synthesis Example 16

A compound having an amino group at the position $R^8$ in the general formula (1) or (2) (compound 7) was synthesized as follows.

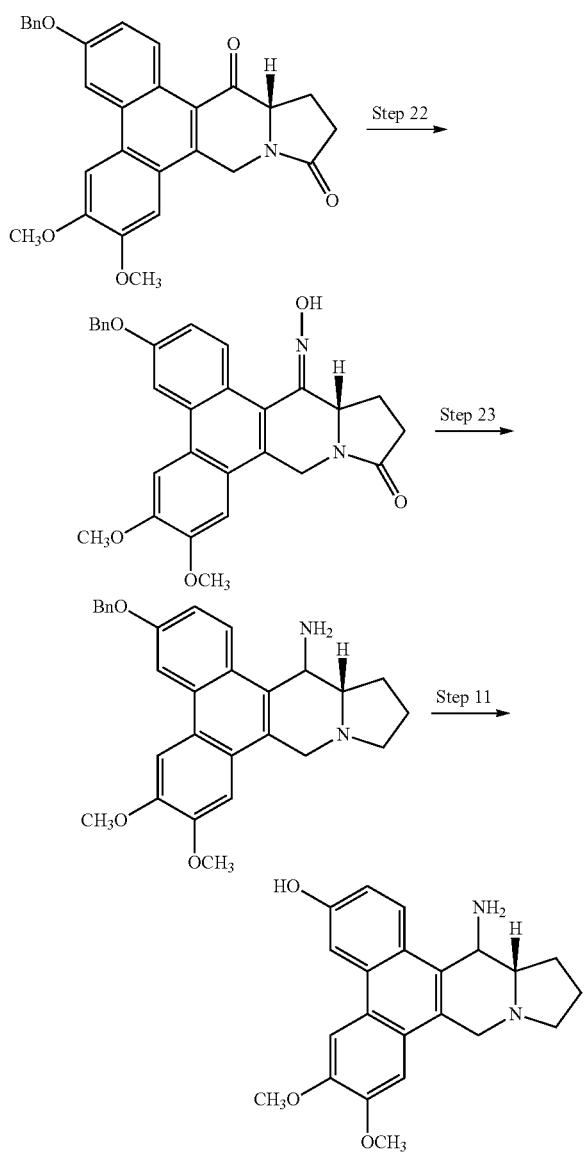

Step 22: Conversion of Ketone to Oxime

In a round-bottom flask, 1 mL of pyridine and 70 mg (1.0 mmol, 2.3 eq.) of hydroxylamine hydrochloride were added to a solution of 200 mg (0.43 mmol) of raw materials in ethanol (20 mL) and 1,4-dioxane (50 mL), and the resulting mixture was heated under reflux. After 72 hours, the disappearance of the raw materials was confirmed, and water was added to the resulting reaction liquid to quench the reaction. The aqueous layer was extracted with ethyl acetate, and the organic layer was dried over anhydrous magnesium sulfate. The solvent was then removed under reduced pressure and the residual product was purified through column chromatography (chloroform:methanol=50:1→40:1) to give 120 mg (57.8%) of a target compound.

$^1$HNMR (400 MHz, CDCl$_3$) δ: 1.92-2.06 (1H, m), 2.32-2.43 (1H, m), 2.50-2.66 (1H, m), 2.89-3.00 (1H, m), 3.78 (1H, d, J=15.6 Hz), 4.06 (6H, s), 4.06-4.13 (1H, m), 4.79 (1H, brs), 5.27 (2H, s), 5.50 (1H, d, J=15.6 Hz), 7.06 (1H, s), 7.50-7.58 (2H, m), 7.32-7.49 (5H, m), 7.68-7.73 (1H, m), 8.43-8.54 (1H, m)

Step 23: Reduction of Oxime and Lactam

Under an argon atmosphere, a solution of 50 mg (0.11 mmol) of raw materials in 20 mL of THF was added dropwise to a 440 μl of 1.0 M solution of lithium aluminium hydride in THF (0.44 mmol, 4 eq.) in a round-bottom flask while stirring with cooling on ice, and subsequently the resulting mixture was heated under reflux. After two hours, the disappearance of the raw materials was confirmed, and 0.25 mL of 15% sodium hydroxide was added to quench the reaction. The aqueous layer was extracted with ethyl acetate, and the organic layer was dried over anhydrous magnesium sulfate. The solvent was then removed under reduced pressure and the residual product was purified through column chromatography (chloroform:methanol=50:1→20:1) to give 31 mg (60.1%) of a target compound.

$^1$HNMR (400 MHz, CDCl$_3$) δ: 1.55-1.70 (1H, m), 1.82-2.26 (3H, m), 2.82-2.94 (1H, m), 3.00-3.15 (1H, m), 3.60-3.70 (1H, m), 3.94 (1H, d, J=14.0 Hz), 4.05 (6H, s), 4.06-4.10 (1H, m), 4.73 (1H, d, J=14.0 Hz), 5.29 (2H, s), 7.29 (1H, dd, J=2.4, 8.8 Hz), 7.31-7.45 (4H, m), 7.50-7.56 (2H, m), 7.77 (1H, s), 7.84 (1H, d, J=8.8 Hz), 7.96 (1H, d, J=2.4 Hz)

Step 11 yield: 22.9%

$^1$HNMR (400 MHz, DMSO-d$_6$) δ: 1.28-1.38 (2H, m), 1.65-1.78 (2H, m), 1.80-1.92 (1H, m), 2.51-2.62 (1H, m), 3.42-3.52 (1H, m), 3.65 (1H, d, J=13.9 Hz), 3.91 (3H, s), 3.93 (3H, s), 4.49 (1H, d, J=13.9 Hz), 5.70-5.80 (1H, m), 7.03 (1H, dd, J=2.4, 8.8 Hz), 7.33 (1H, s), 7.82 (1H, s), 7.88 (1H, d, J=2.4 Hz), 8.11 (1H, d, J=8.8 Hz), 9.65 (1H, brs)

Synthesis Example 17

A compound having a methyl group at the position R$^7$ in the general formula (1) or (2) (compound 6) can be synthesized by changing amino acid ester used in step 6 to α-methylglutamic acid ester.

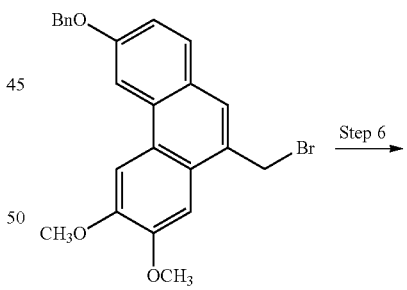

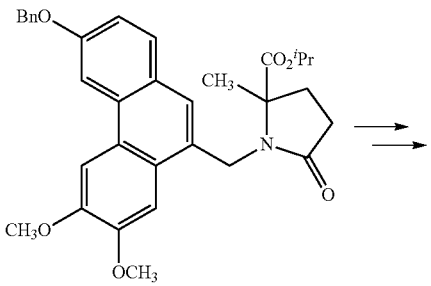

-continued

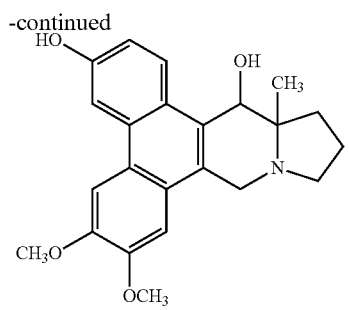

Step 6
  yield: 64.0%
  ¹HNMR (400 MHz, CDCl₃) δ: 0.74 (3H, d, J=6.1 Hz), 0.94 (3H, d, J=6.1 Hz), 1.36 (3H, s), 1.81-1.94 (1H, m), 2.15-2.27 (1H, m), 2.34-2.65 (2H, m), 4.06 (3H, s), 4.08 (3H, s), 4.50 (1H, heptet, J=6.1 Hz), 4.96 (2H, s), 5.27 (2H, s), 7.25 (1H, dd, J=2.0, 8.8 Hz), 7.30-7.45 (3H, m), 7.47 (1H, s), 7.51-7.58 (2H, m), 7.73 (1H, d, J=8.8 Hz), 7.90 (1H, d, J=2.0 Hz)
Step 7
  yield: 75.9%
  ¹HNMR (400 MHz, DMSO-d₆) δ: 1.20 (3H, s), 1.85-1.98 (1H, m), 2.13-2.25 (1H, m), 2.32-2.45 (2H, m), 3.89 (3H, s), 4.02 (3H, s), 4.58 (1H, d, J=15.6 Hz), 5.03 (1H, d, J=15.6 Hz), 5.35 (2H, s), 7.25 (1H, dd, J=2.2, 8.8 Hz), 7.31-7.46 (3H, m), 7.47-7.64 (4H, m), 7.82 (1H, d, J=8.8 Hz), 8.04 (1H, s), 8.13 (1H, d, J=2.2 Hz)
Step 8
  yield: 49.2%
  ¹HNMR (400 MHz, DMSO) δ: 1.44 (3H, s), 2.00-2.13 (1H, m), 2.20-2.36 (1H, m), 2.50-2.69 (2H, m), 4.02 (3H, s), 4.06 (3H, s), 4.82 (1H, d, J=18.8 Hz), 5.50 (1H, d, J=18.8 Hz), 7.15 (1H, dd, J=2.4, 9.3 Hz), 7.48 (1H, s), 7.98 (1H, s), 8.01 (1H, d, J=2.4 Hz), 9.11 (1H, d, J=9.3 Hz), 9.90 (1H, brs)
Steps 9 and 10
  yield: 54.1%
  ¹HNMR (400 MHz, DMSO-d₆) δ: 0.88 (3H, s), 1.72-1.98 (4H, m), 2.70-2.88 (1H, m), 2.96-3.09 (1H, m), 3.82-3.98 (1H, m), 3.92 (3H, s), 3.98 (3H, s), 4.02-4.18 (1H, m), 4.86-4.98 (1H, m), 5.05-5.18 (1H, m), 7.01 (1H, dd, J=1.5, 9.0 Hz), 7.19 (1H, s), 7.89 (2H, s), 8.43 (1H, d, J=9.0 Hz), 9.57 (1H, s)
HPLC Analysis Condition
<HPLC Condition A>
  Column: Daicel CHIRALPAK AS-RH (5 μm, 4.6×150 mm)
  Mobile phase: a mixed solution of H₂O/acetonitrile (40:60)
  Flow rate: 0.5 mL/min
  Detection: 254 nm
  Column temperature: 40° C.
  Measurement time: 30 minutes
<HPLC Condition B>
  Column: Daicel CHIRALCEL OD-RH (5 μm, 4.6×150 mm)
  Mobile phase: a mixed solution of a 20 mM (sodium) phosphate buffer (pH=5.6)/acetonitrile (40:60)
  Flow rate: 0.5 mL/min
  Detection: 254 nm
  Temperature: 40° C.
  Measurement time: 30 minutes
<HPLC Condition C>
  Column: Daicel CHIRALPAK AS-RH (5 μm, 4.6×150 mm)
  Mobile phase: a mixed solution of H₂O/CH₃CN (1:4)
  Flow rate: 0.5 ml/min
  Detection: 254 nm
  Column temperature: 40° C.
<HPLC Condition D>
  Column: Daicel CHIRALCEL OD-RH (5 μm, 4.6×150 mm)
  Mobile phase: a mixed solution of a 20 mM (sodium) phosphate buffer (pH=5.6)/CH₃CN (1:4)
  Flow rate: 0.5 ml/min
  Detection: 254 nm
  Column temperature: 40° C.

Example 1

Measurement of Solubility

In in vivo studies, the phenanthroindolizidine alkaloid compounds were used in the form of a salt.

The results of the measurement of the solubilities of (S)-6,7-dimethoxy-9,10,11,12,12a,13-hexahydro-9a-aza-cyclopenta[b]triphenylene-3-ol hydrochloride (compound 11), (S)-6,7-dimethoxy-9,10,11,12,12a,13-hexahydro-9a-aza-cyclopenta[b]triphenylene-3-ol sulfate (compound 17), (S)-6,7-dimethoxy-9,10,11,12,12a,13-hexahydro-9a-aza-cyclopenta[b]triphenylene-3-ol methanesulfonate (compound 16), and acetic acid(12aS,13S)-3-hydroxy-6,7-dimethoxy-9,10,11,12,12a,13-hexahydro-9a-aza-cyclopenta[b]triphenylene-13-yl ester methanesulfonate (compound 20) are shown below.

TABLE 17

| Compound | Solubility (mg/mL)* |
|---|---|
| 11 | 4.0 |
| 16 | 14.9 |
| 17 | 4.4 |
| 20 | 10.2 |

*the solubility in an aqueous solution of 5% glucose

The phenanthroindolizidine alkaloid compound described above exhibited good solubility in a solvent. Particularly, when its methanesulfonate salt was dissolved in an aqueous solution of 5% glucose, it exhibited a sufficient solubility for administration (>10 mg/ml).

The compounds synthesized as above were used for biological activity tests in the form of an arbitrary salt. Specifically, the salts used were as follows.

It is to be noted that because the compounds 16, 17, 18, 19 and 20, and the aforementioned compounds 11, 13, 12, and 5 are each the same in structure, but only differ in the kind of salt; therefore, the synthetic method for the former compounds is in accordance with the aforementioned synthetic method.

TABLE 18

| Compound | Compound Name |
|---|---|
| Compound 1 | (12aS,13S)-5,6,7-trimethoxy-9,10,11,12,12a,13-hexahydro-9a-aza-cyclopenta[b]triphenylene-3,13-diol hydrochloride |
| Compound 2 | (12aR,13R)-5,6,7-trimethoxy-9,10,11,12,12a,13-hexahydro-9a-aza-cyclopenta[b]triphenylene-3,13-diol hydrochloride |
| Compound 3 | (12aS,13S)-9,10,11,12,12a,13-hexahydro-9a-aza-cyclopenta[b]triphenylene-3,13-diol hydrochloride |
| Compound 4 | (12aS,13S)-6-fluoro-9,10,11,12,12a,13-hexahydro-9a-aza-cyclopenta[b]triphenylene-3,13-diol hydrochloride |

TABLE 18-continued

| Compound | Compound Name |
|---|---|
| Compound 5 | acetic acid(12aS,13S)-3-hydroxy-6,7-dimethoxy-9,10,11,12,12a,13-hexahydro-9a-aza-cyclopenta[b]triphenylene-13-yl ester hydrochloride |
| Compound 6 | 6,7-dimethoxy-12a-methyl-9,10,11,12,12a,13-hexahydro-9a-aza-cyclopenta[b]triphenylene-3,13-diol hydrochloride |
| Compound 7 | (S)-13-amino-6,7-dimethoxy-9,10,11,12,12a,13-hexahydro-9a-aza-cyclopenta[b]triphenylene-3-ol hydrochloride |
| Compound 8 | (12aS,13S)-6,7-methylenedioxy-9,10,11,12,12a,13-hexahydro-9a-aza-cyclopenta[b]triphenylene-3,13-diol hydrochloride |
| Compound 9 | (12aS,13S)-6,7-isopropylidenedioxy-9,10,11,12,12a,13-hexahydro-9a-aza-cyclopenta[b]triphenylene-3,13-diol hydrochloride |

TABLE 19

| Compound | Compound Name |
|---|---|
| Compound 10 | (12aS,13S)-6,7-diethoxy-9,10,11,12,12a,13-hexahydro-9a-aza-cyclopenta[b]triphenylene-3,13-diol hydrochloride |
| Compound 11 | (S)-6,7-dimethoxy-9,10,11,12,12a,13-hexahydro-9a-aza-cyclopenta[b]triphenylene-3-ol hydrochloride |
| Compound 12 | (R)-6,7-dimethoxy-9,10,11,12,12a,13-hexahydro-9a-aza-cyclopenta[b]triphenylene-3-ol hydrochloride |
| Compound 13 | (S)-6,7-methylenedioxy-9,10,11,12,12a,13-hexahydro-9a-aza-cyclopenta[b]triphenylene-3-ol hydrochloride |
| Compound 14 | (S)-6,7-diethoxy-9,10,11,12,12a,13-hexahydro-9a-aza-cyclopenta[b]triphenylene-3-ol hydrochloride |
| Compound 15 | (12aS,13S)-2,3-dimethoxy-9,10,11,12,12a,13-hexahydro-9a-aza-cyclopenta[b]triphenylene-6,13-diol hydrochloride |
| Compound 16 | (S)-6,7-dimethoxy-9,10,11,12,12a,13-hexahydro-9a-aza-cyclopenta[b]triphenylene-3-ol methanesulfonate |
| Compound 17 | (S)-6,7-dimethoxy-9,10,11,12,12a,13-hexahydro-9a-aza-cyclopenta[b]triphenylene-3-ol sulfate |
| Compound 18 | (S)-6,7-methylenedioxy-9,10,11,12,12a,13-hexahydro-9a-aza-cyclopenta[b]triphenylene-3-ol methanesulfonate |
| Compound 19 | (R)-6,7-dimethoxy-9,10,11,12,12a,13-hexahydro-9a-aza-cyclopenta[b]triphenylene-3-ol methanesulfonate |
| Compound 21 | (S)-2-chloro-6,7-dimethoxy-9,10,11,12,12a,13-hexahydro-9a-aza-cyclopenta[b]triphenylene-3-ol methanesulfonate |
| Compound 22 | (S)-4-chloro-6,7-dimethoxy-9,10,11,12,12a,13-hexahydro-9a-aza-cyclopenta[b]triphenylene-3-ol methanesulfonate |
| Compound 23 | (S)-2,4-dichloro-6,7-dimethoxy-9,10,11,12,12a,13-hexahydro-9a-aza-cyclopenta[b]triphenylene-3-ol methanesulfonate |

TABLE 20

| Compound | Name of Compound |
|---|---|
| Compound 24 | (S)-4-fluoro-6,7-dimethoxy-9,10,11,12,12a,13-hexahydro-9a-aza-cyclopenta[b]triphenylene-3-ol |
| Compound 25 | (S)-2-fluoro-6,7-dimethoxy-9,10,11,12,12a,13-hexahydro-9a-aza-cyclopenta[b]triphenylene-3-ol methanesulfonate |
| Compound 26 | (S)-6,7-dimethoxy-2,4-dimethyl-9,10,11,12,12a,13-hexahydro-9a-aza-cyclopenta[b]triphenylene-3-ol methanesulfonate |

Example 2

Inhibitory Action on the NFκB Activity

The action of the phenanthroindolizidine alkaloid compound of the present invention on the NFκB activity was studied in a luciferase assay. Human colon cancer SW480 cells were transfected with pNFκB-Luc Plasmid (Stratagene), which is a reporter vector in which a five-time tandem repeat of the NFκB responsive element (NRE) is integrated into the upstream of the luciferase gene, using Lipofectamine 2000 (Invitrogen Corporation) in accordance with the attached operating procedure. Subsequently, the cells were cultured in an RPMI1640 medium containing 10% FBS, 100 U/mL penicillin, 100 μg/mL streptomycin, and 0.5 mg/mL G418 to produce SW480 cells having the luciferase gene, the expression of which is regulated by NRE, stably introduced therein (SW480/NRE-Luc cells). Likewise, SW480 cells were transfected with pGL3-Control Vector (Promega Corporation), which is a reporter vector in which the SV40 promoter is integrated into the upstream of the luciferase gene, to produce SW480 cells having the luciferase gene, the expression of which is regulated by the SV40 promoter, stably introduced therein (SW480/SV40-Luc cells). The SW480/NRE-Luc cells or the SW480/SV40-Luc cells were suspended in an RPMI1640 medium containing 10% FBS, 100 U/mL penicillin, and 100 μg/mL streptomycin (10% FBS/RPMI1640), and then seeded in a 96-well microplate, followed by culturing under conditions of 5% $CO_2$ and at 37° C. (5000 cells/well). After an overnight culture, the compound of the present invention was added, followed by culturing for one hour. Further, 50 ng/mL TNFα (Sigma-Aldrich Corporation) was added, followed by culturing for four hours. Subsequently, a Steady-Glo Luciferase Assay reagent (Promega Corporation) was added, and the luminescent intensity was detected by SpectraMax M5e (Molecular Devices, Inc.) to measure the intracellular luciferase activity. It is to be noted that the action of the compound of the present invention on the NFκB activity or the SV40 promoter activity was shown as $IC_{50}$ values (the concentration of a test compound needed for 50% inhibition of the induction of the luciferase expression). The results are shown below.

TABLE 21

| Compound | NFκB inhibitory activity $IC_{50}$ (ng/mL) | SV40 promoter inhibitory activity $IC_{50}$ (ng/mL) |
|---|---|---|
| Compound 1 | 667.7 | >10000 |
| Compound 2 | 1.0 | >1000 |
| Compound 3 | 172.6 | >10000 |
| Compound 4 | 285.7 | >10000 |
| Compound 5 | 27.0 | >100 |
| Compound 6 | 1924.2 | >10000 |
| Compound 7 | 468.0 | >10000 |
| Compound 8 | 8.4 | >10000 |
| Compound 9 | 521.6 | >10000 |
| Compound 10 | 4.1 | >100 |
| Compound 11 | 1.2 | >10 |
| Compound 12 | 18.1 | >10000 |
| Compound 13 | 48.4 | >10000 |
| Compound 14 | 4.7 | >1000 |
| Compound 15 | 2.0 | >10000 |
| Compound 21 | 5.4 | >1000 |
| Compound 22 | 0.41 | >100 |
| Compound 25 | 1.6 | >1000 |
| Compound 26 | 59.7 | >10000 |
| PDTC | 2400 | >10000 |

As shown above, the phenanthroindolizidine alkaloid compound of the present invention exhibited a potent inhibitory activity on the NFκB activity. While pyrrolidine dithiocarbamate (PDTC), which is known to have an NFκB inhibitory activity, was used as a positive control drug in the present experiment, all of the compounds of the present invention studied exhibited a stronger NFκB inhibitory activity than did PDTC. Meanwhile, it was shown that these compounds did not affect the SV40 promoter activity, indicating that they specifically acted on NFκB.

Example 3

Inhibitory Action on the Proliferation of Cancer Cell

The action of the phenanthroindolizidine alkaloid compound of the present invention on the proliferation of human colon cancer SW480 cells, HT-29 cells, and human non-small cell lung cancer A549 cells was studied. The SW480 cells were suspended in a 10% FBS/RPMI1640 and then seeded in a 96-well microplate, followed by culturing in 5% $CO_2$ at 37° C. (2000 cells/well). The A549 cells and the HT-29 cells were each suspended in a DMEM medium containing 10% FBS, 100 U/mL penicillin, and 100 µg/mL streptomycin (10% FBS/DMEM) and a DMEM F-12 HAM medium containing 10% FBS, 100 U/mL penicillin, and 100 µg/mL streptomycin (10% FBS/DMEM F12 HAM), and then seeded in 96-well microplates, followed by culturing in 5% $CO_2$ at 37° C. (1000 cells/well). After an overnight culture, the compound of the present invention was added, followed by further culturing for 48 hours (SW480 cells) and 96 hours (A549 cells and HT-29 cells). After culturing, the number of viable cells was counted using TetraColor ONE (Seikagaku Corporation) in accordance with the attached operating procedure. The results were expressed as the concentration of a test compound needed for 50% inhibition of the proliferation of the cells ($IC_{50}$).

TABLE 22

| Compound | SW480 proliferation inhibitory action $IC_{50}$ (ng/mL) | HT-29 proliferation inhibitory action $IC_{50}$ (ng/mL) | A549 proliferation inhibitory action $IC_{50}$ (ng/mL) |
| --- | --- | --- | --- |
| Compound 1 | 1969.2 | 637.0 | 560 |
| Compound 2 | 3.6 | 4.7 | 2.5 |
| Compound 3 | 405.3 | 140.4 | 107.5 |
| Compound 4 | 503.0 | 218.2 | 152.2 |
| Compound 5 | 5.0 | 2.3 | 0.5 |
| Compound 6 | 3123.5 | 839.0 | 757.0 |
| Compound 7 | 2340.6 | 243.0 | 265.0 |
| Compound 8 | 26.7 | 46.9 | 19.3 |
| Compound 9 | 1955.0 | 184.0 | 350.2 |
| Compound 10 | 6.7 | 0.47 | 0.27 |
| Compound 11 | 3.8 | 0.62 | 0.024 |
| Compound 12 | 50.4 | 50.4 | 12.7 |
| Compound 13 | 38.7 | 260.5 | 48.2 |
| Compound 14 | 15.4 | 12.1 | 2.1 |
| Compound 15 | 4.2 | 56.6 | 34.0 |
| Compound 21 | 6.7 | 6.8 | 8.0 |
| Compound 22 | 0.60 | 4.1 | 0.71 |
| Compound 25 | 3.1 | 7.0 | 2.6 |
| Compound 26 | 32.1 | 50.0 | 100.2 |

As shown above, the phenanthroindolizidine alkaloid compound of the present invention exhibited a potent inhibitory action on the proliferation of SW480 cells, HT-29 cells, and A549 cells.

Example 4

Antitumor Effect in Mice Transplanted with Mouse Fibrosarcoma Meth A Cells

The antitumor effect of the phenanthroindolizidine alkaloid compound of the present invention in vivo was studied using mice transplanted with mouse fibrosarcoma Meth A cells. Meth A cells were transplanted subcutaneously in the inguinal region of male 7-week-old BALB/c mice ($2.5 \times 10^5$ cells/mouse). Subsequently, on days 1, 5, and 9, the compound of the present invention was intravenously administered. To a control group, physiological saline as a solvent, was administered. On day 21 after the cell transplantation, tumor was excised and measured for its weight, and subsequently a tumor growth-inhibition rate IR (%) was obtained by the following formula.

Tumor growth-inhibition rate IR(%)=(1−the weight of the tumor in an administration group/the weight of the tumor in a control group)×100

The results were shown below.

TABLE 23

| Compound | Total dose (mg/kg) | Tumor growth inhibition rate IR (%) |
| --- | --- | --- |
| Compound 11 | 25 | 52.1** |
|  | 50 | 64.6** |
| Compound 12 | 25 | 25.3 |
|  | 50 | 58.8** |
| Compound 13 | 25 | 45.6* |
|  | 50 | 31.5 |

*$P < 0.05$,
**$P < 0.01$; a significant difference in comparison with a solvent (Dunnett's test)

As shown above, the phenanthroindolizidine alkaloid compound of the present invention was shown to exhibit an antitumor effect in mice transplanted with mouse fibrosarcoma Meth A cells.

Example 5

Antitumor Effect in Mice Transplanted with Human Colon Cancer HCT116 Cells

The antitumor effect of the phenanthroindolizidine alkaloid compound of the present invention in vivo was studied using mice transplanted with human colon cancer HCT116 cells. HCT116 cells were transplanted subcutaneously in the inguinal region of male 6-week-old BALB/c nude mice ($2 \times 10^6$ cells/mouse). On days 1 to 5 and on days 8 to 12 after the time at which the estimated tumor volume obtained by $1/2ab^2$ (a and b indicate the major axis and the minor axis of tumor, respectively) reached approximately 100 mm$^3$ (day 0), the compound of the present invention was administered (intraperitoneal administration). To a control group, a 5% glucose solution as a solvent, was administered. On day 21, tumor was excised and measured for its weight, and subsequently a tumor proliferation-inhibition rate IR (%) was calculated. The results are shown below.

TABLE 24

| Compound | Total dose (mg/kg) | Tumor growth inhibition rate IR (%) |
|---|---|---|
| Compound 16 | 100 | 35.7*** |
|  | 200 | 48.7*** |

*P < 0.05,
**P < 0.01,
***P < 0.001; a significant difference in comparison with a solvent (Dunnett's test)

As shown above, the phenanthroindolizidine alkaloid compound of the present invention was shown to exhibit an antitumor effect in mice transplanted with human colon cancer HCT116 cells.

Example 6

Antitumor Effect in Mice Transplanted with Human Promyelocytic Leukemia HL-60 Cells The antitumor effect of the phenanthroindolizidine alkaloid compound of the present invention in vivo was studied using mice transplanted with human promyelocytic leukemia HL-60 cells. HL-60 cells were transplanted subcutaneously in the inguinal region of male 6-week-old BALB/c nude mice ($2 \times 10^6$ cells/mouse). On days 1, 5, and 9 after the time at which the estimated tumor volume reached approximately 100 mm$^3$ (day 0), the compound of the present invention was intravenously administered. To a control group, a 5% glucose solution as a solvent, was administered. On day 15, tumor was excised and measured for its weight, and subsequently a tumor growth-inhibition rate IR (%) was calculated. As a result, as shown in FIG. 1, the phenanthroindolizidine alkaloid compound of the present invention was shown to exhibit an antitumor effect in mice transplanted with human promyelocytic leukemia HL-60 cells. The tumor growth-inhibition rates IR (%) in the groups receiving total doses of 50 and 100 mg/kg of the compound were each found to be 57.4% (p<0.01 vs. control group) and 96.8% (p<0.001 vs. control group), respectively.

Example 7

Anti-Inflammatory Effect in Mice with TPA-Induced Ear Edema

Figure 2:
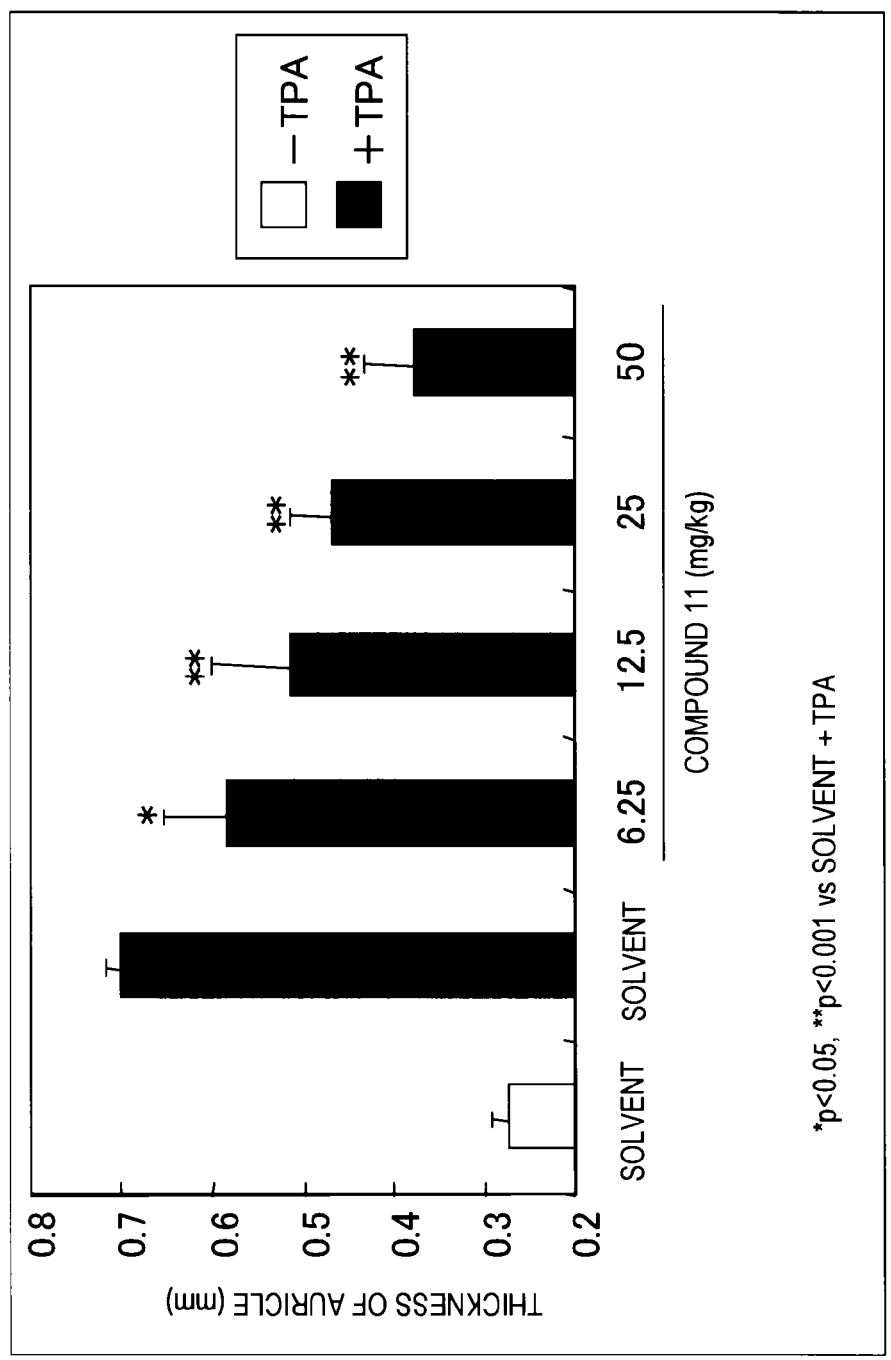
FIG. 2 is a graph showing the anti-inflammatory effect of the compound of the present invention in mice with TPA-induced ear edema.

The anti-inflammatory effect of the phenanthroindolizidine alkaloid compound of the present invention in vivo was studied using mice with phorbol 12-myristate 13-acetate (TPA)-induced ear edema. Compound 11, a compound of the present invention, was intraperitoneally administered to male 6-week-old ICR mice, and after 30 minutes, TPA (Sigma-Aldrich Corporation) dissolved in acetone was applied to the front and back of the right ear of the mice (5 μg/ear). Four hours after application of TPA, the thickness of the auricle was measured by a dial thickness gauge (Ozaki Mfg Co. Ltd.). A control group was administered with a 5% glucose solution as a solvent. As a result, as shown in FIG. 2, it was shown that the compound 11, a phenanthroindolizidine alkaloid compound of the present invention, exhibited an anti-inflammatory effect by inhibiting TPA-induced ear edema in a dose-dependent manner.

Example 8

Animal Toxicity Test

In order to examine the toxicity of the phenanthroindolizidine alkaloid compound of the present invention in animals, the compound of the present invention was intravenously administered to mice transplanted with mouse fibrosarcoma Meth A cells (total doses were 25 and 50 mg/kg) on days 1, 5, and 9 after the day of transplantation (day 0), and its effect on the survival of the mice was observed for three weeks from the initiation of the administration. Also, the toxicity of known phenanthroindolizidine alkaloid compounds in mice, namely (12aS,13S)-6,7-dimethoxy-9,10,11,12,12a,13-hexahydro-9a-aza-cyclopenta[b]triphenylene-3,13-diol (known compound 1; refer to WO01/023384) and (12aS,13S)-3,6,7-trimethoxy-9,10,11,12,12a,13-hexahydro-9a-aza-cyclopenta[b]triphenylene-13-ol (known compound 2; refer to Planta Med., 2002, 68: 186-188), was simultaneously studied. To a control group, a physiological saline solution as a solvent, was administered. The results are shown in the following tables.

TABLE 25

| Compound | Total dose (mg/kg) | Mortality rate |
|---|---|---|
| Solvent | 0 | 0/5 |
| Known compound 1 | 25 | 0/5 |
|  | 50 | 5/5 |
| Known Compound 2 | 25 | 2/5 |
|  | 50 | 5/5 |
| Compound 1 | 25 | 0/5 |
|  | 50 | 0/5 |
| Compound 3 | 25 | 0/5 |
|  | 50 | 0/5 |
| Compound 5 | 25 | 0/5 |
|  | 50 | 0/5 |
| Compound 6 | 25 | 0/5 |
|  | 50 | 0/5 |
| Compound 8 | 25 | 0/5 |
|  | 50 | 0/5 |
| Compound 9 | 25 | 0/5 |
|  | 50 | 0/5 |
| Compound 10 | 25 | 0/5 |
|  | 50 | 0/5 |
| Compound 11 | 25 | 0/5 |
|  | 50 | 0/5 |
| Compound 12 | 25 | 0/5 |
|  | 50 | 0/5 |

TABLE 26

| Compound | Total dose (mg/kg) | Mortality rate |
|---|---|---|
| Compound 13 | 25 | 0/5 |
|  | 50 | 0/5 |
| Compound 15 | 25 | 0/5 |
|  | 50 | 0/5 |

As shown above, all the mice survived in a group administered with the compound of the present invention. On the other hand, all the mice died in a group administered with 50 mg/kg of the known phenanthroindolizidine alkaloid compounds (known compounds 1 and 2). Particularly with the known compound 2, some of the mice also died in a group administered with 25 mg/kg of the compound. From the above results, the phenanthroindolizidine alkaloid compound of the present invention was shown to have reduced toxicity in animals compared to the known compounds 1 and 2.

Example 9

Production of Tablets

The components shown below were mixed and the resulting mixture was tableted.

TABLE 27

| Compound 16 | 100 mg |
|---|---|
| Lactose | 100 mg |
| Potato starch | 39 mg |
| Microcrystalline cellulose | 30 mg |
| Synthetic aluminum silicate | 30 mg |
| Calcium stearate | 1 mg |
| Total (per tablet) | 300 mg |

The invention claimed is:

1. A compound represented by formula (1) or a salt thereof:

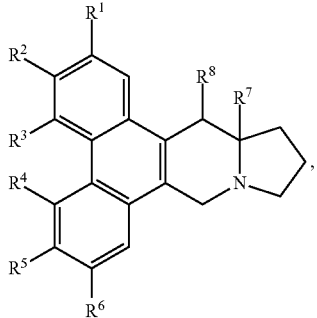

(1)

wherein
$R^1$ represents a hydrogen atom, a lower alkyl group, a lower alkyloxy group, or a halogen atom;
$R^2$ represents a hydroxyl group, or a lower alkyloxy group;
$R^3$ represents a hydrogen atom, a lower alkyl group, or a halogen atom;
$R^4$ represents a hydrogen atom or a lower alkyloxy group;
$R^5$ represents a hydrogen atom, a lower alkyloxy group, a halogen atom, a hydroxyl group, or a methylenedioxy group formed together with $R^6$, or an isopropylidenedioxy group formed together with $R^6$;
$R^6$ represents a hydrogen atom, a lower alkyloxy group, or a methylenedioxy group formed together with $R^5$, or an isopropylidenedioxy group formed together with $R^5$;
$R^7$ represents a hydrogen atom or a lower alkyl group; and
$R^8$ represents a hydrogen atom, a hydroxyl group, or an amino group;
provided that the following cases are excluded:
(A) the case where $R^1$, $R^3$, $R^4$, and $R^7$ are hydrogen atoms, $R^2$ and $R^8$ are hydroxyl groups, and $R^5$ and $R^6$ are methoxy groups;
(B) the case where $R^1$, $R^3$, $R^4$, and $R^7$ are hydrogen atoms, $R^2$, $R^5$, and $R^6$ are methoxy groups, and $R^8$ is a hydroxyl group;
(C) the case where $R^1$, $R^3$, $R^4$, $R^7$, and $R^8$ are hydrogen atoms and $R^2$, $R^5$, and $R^6$ are methoxy groups;
(D) the case where $R^1$, $R^3$, $R^4$, and $R^7$ are hydrogen atoms, $R^2$, $R^5$, and $R^8$ are hydroxyl groups, and $R^6$ is a methoxy group;
(E) the case where $R^1$, $R^3$, $R^4$, and $R^7$ are hydrogen atoms, $R^2$ and $R^6$ are methoxy groups, and $R^5$ and $R^8$ are hydroxyl groups;
(F) the case where $R^1$, $R^3$, $R^4$, $R^7$, and $R^8$ are hydrogen atoms, $R^2$ and $R^6$ are methoxy groups, and $R^5$ is a hydroxyl group;
(G) the case where $R^1$, $R^2$, $R^5$, and $R^6$ are methoxy groups and $R^3$, $R^4$, $R^7$, and $R^8$ are hydrogen atoms;
(H) the case where $R^1$, $R^2$, $R^4$, and $R^5$ are methoxy groups and $R^3$, $R^6$, $R^7$, and $R^8$ are hydrogen atoms;
(I) the case where $R^1$, $R^2$, $R^5$, and $R^6$ are methoxy groups, $R^3$, $R^4$, and $R^7$ are hydrogen atoms, and $R^8$ is a hydroxyl group;
(J) the case where $R^1$ and $R^2$ are methoxy groups, $R^3$, $R^4$, $R^6$, $R^7$, and $R^8$ are hydrogen atoms, and $R^5$ is a hydroxyl group;
(K) the case where $R^1$, $R^2$, and $R^5$ are methoxy groups, and $R^3$, $R^4$, $R^6$, $R^7$, and $R^8$ are hydrogen atoms;
(L) the case where $R^1$, $R^2$, and $R^5$ are methoxy groups, $R^3$, $R^4$, $R^6$, and $R^7$ are hydrogen atoms, and $R^8$ is a hydroxyl group;
(M) the case where $R^1$, $R^2$, and $R^5$ are methoxy groups, $R^3$, $R^4$, $R^6$, and $R^8$ are hydrogen atoms, and $R^7$ is a methyl group;
(N) the case where $R^1$, $R^2$, and $R^5$ are methoxy groups, $R^3$, $R^4$, and $R^6$ are hydrogen atoms, $R^7$ is a methyl group, and $R^8$ is a hydroxyl group;
(O) the case where $R^1$, $R^2$, and $R^6$ are methoxy groups, $R^3$, $R^4$, $R^7$, and $R^8$ are hydrogen atoms, and $R^5$ is a hydroxyl group;
(P) the case where $R^1$, $R^2$, and $R^4$ are methoxy groups, $R^3$, $R^6$, $R^7$, and $R^8$ are hydrogen atoms, and $R^5$ is a hydroxyl group;
(Q) the case where $R^1$, $R^5$, and $R^6$ are methoxy groups, $R^2$ and $R^8$ are hydroxyl groups, and $R^3$, $R^4$, and $R^7$ are hydrogen atoms;
(R) the case where $R^1$ is an isopropyloxy group, $R^2$ and $R^5$ are methoxy groups, and $R^3$, $R^4$, $R^6$, $R^7$ and $R^8$ are hydrogen atoms;
(S) the case where $R^1$ and $R^5$ are methoxy groups, $R^2$ is an isopropyloxy group, and $R^3$, $R^4$, $R^6$, $R^7$ and $R^8$ are hydrogen atoms;
(T) the case where $R^1$ and $R^2$ are methoxy groups, $R^3$, $R^4$, $R^6$, $R^7$, and $R^8$ are hydrogen atoms, and $R^5$ is an isopropyloxy group;
(U) the case where $R^1$ and $R^5$ are methoxy groups, $R^2$ is a hydroxyl group, and $R^3$, $R^4$, $R^6$, $R^7$, and $R^8$ are hydrogen atoms;
(V) the case where $R^1$ and $R^2$ are methoxy groups, and $R^3$, $R^4$, $R^5$, $R^6$, $R^7$, and $R^8$ are hydrogen atoms;
(AE) the case where $R^1$, $R^3$, $R^4$, and $R^8$ are hydrogen atoms, $R^2$, $R^5$, and $R^6$ are methoxy groups, and $R^7$ is a methyl group;
(AH) the case where $R^1$, $R^2$, $R^4$, and $R^5$ are methoxy; $R^3$, $R^6$, and $R^7$ are hydrogen atoms; and $R^8$ is a hydroxyl group; and
(AI) the case where $R^1$, $R^5$, and $R^6$ are methoxy, $R^2$ is a hydroxyl, and $R^3$, $R^4$, $R^7$, and $R^8$ are hydrogen.

2. The compound or salt of claim 1, wherein $R^1$ represents a hydrogen atom, an alkyl group with a carbon number of 1 to 6, an alkyloxy group with a carbon number of 1 to 6, or a halogen atom;
$R^2$ represents a hydroxyl group, or an alkyloxy group with a carbon number of 1 to 6;
$R^3$ represents a hydrogen atom, an alkyl group with a carbon number of 1 to 6, or a halogen atom;
$R^4$ represents a hydrogen atom or an alkyloxy group with a carbon number of 1 to 6;
$R^5$ represents a hydrogen atom, an alkyloxy group with a carbon number of 1 to 6, a halogen atom, a hydroxyl group, or a methylenedioxy group formed together with $R^6$, or an isopropylidenedioxy group formed together with $R^6$;

$R^6$ represents a hydrogen atom, an alkyloxy group with a carbon number of 1 to 6, or a methylenedioxy group formed together with $R^5$, or an isopropylidenedioxy group formed together with $R^5$;

$R^7$ represents a hydrogen atom or an alkyl group with a carbon number of 1 to 6; and $R^8$ represents a hydrogen atom, a hydroxyl group, or an amino group;

provided that the following cases are excluded:

(A) the case where $R^1$, $R^3$, $R^4$, and $R^7$ are hydrogen atoms, $R^2$ and $R^8$ are hydroxyl groups, and $R^5$ and $R^6$ are methoxy groups;

(B) the case where $R^1$, $R^3$, $R^4$, and $R^7$ are hydrogen atoms, $R^2$, $R^5$, and $R^6$ are methoxy groups, and $R^8$ is a hydroxyl group;

(C) the case where $R^1$, $R^3$, $R^4$, $R^7$, and $R^8$ are hydrogen atoms and $R^2$, $R^5$, and $R^6$ are methoxy groups;

(D) the case where $R^1$, $R^3$, $R^4$, and $R^7$ are hydrogen atoms, $R^2$, $R^5$, and $R^8$ are hydroxyl groups, and $R^6$ is a methoxy group;

(E) the case where $R^1$, $R^3$, $R^4$, and $R^7$ are hydrogen atoms, $R^2$ and $R^6$ are methoxy groups, and $R^5$ and $R^8$ are hydroxyl groups;

(F) the case where $R^1$, $R^3$, $R^4$, $R^7$, and $R^8$ are hydrogen atoms, $R^2$ and $R^6$ are methoxy groups, and $R^5$ is a hydroxyl group;

(G) the case where $R^1$, $R^2$, $R^5$, and $R^6$ are methoxy groups and $R^3$, $R^4$, $R^7$, and $R^8$ are hydrogen atoms;

(H) the case where $R^1$, $R^2$, $R^4$, and $R^5$ are methoxy groups and $R^3$, $R^6$, $R^7$, and $R^8$ are hydrogen atoms;

(I) the case where $R^1$, $R^2$, $R^5$, and $R^6$ are methoxy groups, $R^3$, $R^4$, and $R^7$ are hydrogen atoms, and $R^8$ is a hydroxyl group;

(J) the case where $R^1$ and $R^2$ are methoxy groups, $R^3$, $R^4$, $R^6$, $R^7$, and $R^8$ are hydrogen atoms, and $R^5$ is a hydroxyl group;

(K) the case where $R^1$, $R^2$, and $R^5$ are methoxy groups, and $R^3$, $R^4$, $R^6$, $R^7$, and $R^8$ are hydrogen atoms;

(L) the case where $R^1$, $R^2$, and $R^5$ are methoxy groups, $R^3$, $R^4$, $R^6$, and $R^7$ are hydrogen atoms, and $R^8$ is a hydroxyl group;

(M) the case where $R^1$, $R^2$, and $R^5$ are methoxy groups, $R^3$, $R^4$, $R^6$, and $R^8$ are hydrogen atoms, and $R^7$ is a methyl group;

(N) the case where $R^1$, $R^2$, and $R^5$ are methoxy groups, $R^3$, $R^4$, and $R^6$ are hydrogen atoms, $R^7$ is a methyl group, and $R^8$ is a hydroxyl group;

(O) the case where $R^1$, $R^2$, and $R^6$ are methoxy groups, $R^3$, $R^4$, $R^7$, and $R^8$ are hydrogen atoms, and $R^5$ is a hydroxyl group;

(P) the case where $R^1$, $R^2$, and $R^4$ are methoxy groups, $R^3$, $R^6$, $R^7$, and $R^8$ are hydrogen atoms, and $R^5$ is a hydroxyl group;

(Q) the case where $R^1$, $R^5$, and $R^6$ are methoxy groups, $R^2$ and $R^8$ are hydroxyl groups, and $R^3$, $R^4$, and $R^7$ are hydrogen atoms;

(R) the case where $R^1$ is an isopropyloxy group, $R^2$ and $R^5$ are methoxy groups, and $R^3$, $R^4$, $R^6$, $R^7$, and $R^8$ are hydrogen atoms;

(S) the case where $R^1$ and $R^5$ are methoxy groups, $R^2$ is an isopropyloxy group, and $R^3$, $R^4$, $R^6$, $R^7$, and $R^8$ are hydrogen atoms;

(T) the case where $R^1$ and $R^2$ are methoxy groups, $R^3$, $R^4$, $R^6$, $R^7$, and $R^8$ are hydrogen atoms, and $R^5$ is an isopropyloxy group;

(U) the case where $R^1$ and $R^5$ are methoxy groups, $R^2$ is a hydroxyl group, and $R^3$, $R^4$, $R^6$, $R^7$, and $R^8$ are hydrogen atoms;

(V) the case where $R^1$ and $R^2$ are methoxy groups, and $R^3$, $R^4$, $R^6$, $R^7$, and $R^8$ are hydrogen atoms;

(AE) the case where $R^1$, $R^3$, $R^4$, and $R^8$ are hydrogen atoms, $R^2$, $R^5$, and $R^6$ are methoxy groups, and $R^7$ is a methyl group;

(AH) the case where $R^1$, $R^2$, $R^4$, and $R^5$ are methoxy; $R^3$, $R^6$, and $R^7$ are hydrogen atoms; and $R^8$ is a hydroxyl group; and (AI) the case where $R^1$, $R^5$, and $R^6$ are methoxy, $R^2$ is a hydroxyl, and $R^3$, $R^4$, $R^7$, and $R^8$ are hydrogen.

3. The compound or salt of claim 1, wherein $R^1$ represents a hydrogen atom, a methyl group, a methoxy group, a chlorine atom, or a fluorine atom;

$R^2$ represents a hydroxyl group, or a methoxy group;

$R^3$ represents a hydrogen atom, a methyl group, a chlorine atom, or a fluorine atom;

$R^4$ represents a hydrogen atom or a methoxy group;

$R^5$ represents a hydrogen atom, a methoxy group, an ethoxy group, a fluorine atom, a hydroxyl group, or a methylenedioxy group formed together with $R^6$, or an isopropylidenedioxy group formed together with $R^6$;

$R^6$ represents a hydrogen atom, a methoxy group, an ethoxy group, or a methylenedioxy group formed together with $R^5$, or an isopropylidenedioxy group formed together with $R^5$;

$R^7$ represents a hydrogen atom or a methyl group; and $R^8$ represents a hydrogen atom, a hydroxyl group, or an amino group, or an acetoxy group;

provided that the following cases are excluded:

(A) the case where $R^1$, $R^3$, $R^4$, and $R^7$ are hydrogen atoms, $R^2$ and $R^8$ are hydroxyl groups, and $R^5$ and $R^6$ are methoxy groups;

(B) the case where $R^1$, $R^3$, $R^4$, and $R^7$ are hydrogen atoms, $R^2$, $R^5$, and $R^6$ are methoxy groups, and $R^8$ is a hydroxyl group;

(C) the case where $R^1$, $R^3$, $R^4$, $R^7$, and $R^8$ are hydrogen atoms and $R^2$, $R^5$, and $R^6$ are methoxy groups;

(D) the case where $R^1$, $R^3$, $R^4$, and $R^7$ are hydrogen atoms, $R^2$, $R^5$, and $R^8$ are hydroxyl groups, and $R^6$ is a methoxy group;

(E) the case where $R^1$, $R^3$, $R^4$, and $R^7$ are hydrogen atoms, $R^2$ and $R^6$ are methoxy groups, and $R^5$ and $R^8$ are hydroxyl groups;

(F) the case where $R^1$, $R^3$, $R^4$, $R^7$, and $R^8$ are hydrogen atoms, $R^2$ and $R^6$ are methoxy groups, and $R^5$ is a hydroxyl group;

(G) the case where $R^1$, $R^2$, $R^5$, and $R^6$ are methoxy groups and $R^3$, $R^4$, $R^7$, and $R^8$ are hydrogen atoms;

(H) the case where $R^1$, $R^2$, $R^4$, and $R^5$ are methoxy groups and $R^3$, $R^6$, $R^7$, and $R^8$ are hydrogen atoms;

(I) the case where $R^1$, $R^2$, $R^5$, and $R^6$ are methoxy groups, $R^3$, $R^4$, and $R^7$ are hydrogen atoms, and $R^8$ is a hydroxyl group;

(J) the case where $R^1$ and $R^2$ are methoxy groups, $R^3$, $R^4$, $R^6$, $R^7$, and $R^8$ are hydrogen atoms, and $R^5$ is a hydroxyl group;

(K) the case where $R^1$, $R^2$, and $R^5$ are methoxy groups, and $R^3$, $R^4$, $R^6$, $R^7$, and $R^8$ are hydrogen atoms;

(L) the case where $R^1$, $R^2$, and $R^5$ are methoxy groups, $R^3$, $R^4$, $R^6$, and $R^7$ are hydrogen atoms, and $R^8$ is a hydroxyl group;

(M) the case where R¹, R², and R⁵ are methoxy groups, R³, R⁴, R⁶, and R⁸ are hydrogen atoms, and R⁷ is a methyl group;
(N) the case where R¹, R², and R⁵ are methoxy groups, R³, R⁴, and R⁶ are hydrogen atoms, R⁷ is a methyl group, and R⁸ is a hydroxyl group;
(O) the case where R¹, R², and R⁶ are methoxy groups, R³, R⁴, R⁷, and R⁸ are hydrogen atoms, and R⁵ is a hydroxyl group;
(P) the case where R¹, R², and R⁴ are methoxy groups, R³, R⁶, R⁷, and R⁸ are hydrogen atoms, and R⁵ is a hydroxyl group;
(Q) the case where R¹, R⁵, and R⁶ are methoxy groups, R² and R⁸ are hydroxyl groups, and R³, R⁴, and R⁷ are hydrogen atoms;
(R) the case where R¹ is an isopropyloxy group, R² and R⁵ are methoxy groups, and R³, R⁴, R⁶, R⁷ and R⁸ are hydrogen atoms;
(S) the case where R¹ and R⁵ are methoxy groups, R² is an isopropyloxy group, and R³, R⁴, R⁶, R⁷ and R⁸ are hydrogen atoms;
(T) the case where R¹ and R² are methoxy groups, R³, R⁴, R⁶, R⁷, and R⁸ are hydrogen atoms, and R⁵ is an isopropyloxy group;
(U) the case where R¹ and R⁵ are methoxy groups, R² is a hydroxyl group, and R³, R⁴, R⁶, R⁷, and R⁸ are hydrogen atoms;
(V) the case where R¹ and R² are methoxy groups, and R³, R⁴, R⁵, R⁶, R⁷, and R⁸ are hydrogen atoms;
(AE) the case where R¹, R³, R⁴, and R⁸ are hydrogen atoms, R², R⁵, and R⁶ are methoxy groups, and R⁷ is a methyl group;
(AH) the case where R¹, R², R⁴, and R⁵ are methoxy; R³, R⁶, and R⁷ are hydrogen atoms; and R⁸ is a hydroxyl group; and
(AI) the case where R¹, R⁵, and R⁶ are methoxy, R² is a hydroxyl, and R³, R⁴, R⁷, and R⁸ are hydrogen.
4. A compound having a conformation represented by formula (2):

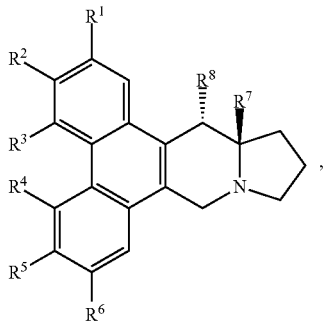

(2)

wherein
R¹ represents a hydrogen atom, a lower alkyl group, a lower alkyloxy group, or a halogen atom;
R² represents a hydroxyl group, or a lower alkyloxy group;
R³ represents a hydrogen atom, a lower alkyl group, or a halogen atom;
R⁴ represents a hydrogen atom or a lower alkyloxy group;
R⁵ represents a hydrogen atom, a lower alkyloxy group, a halogen atom, a hydroxyl group, or a methylenedioxy group formed together with R⁶, or an isopropylidenedioxy group formed together with R⁶;
R⁶ represents a hydrogen atom, a lower alkyloxy group, or a methylenedioxy group formed together with R⁵, or an isopropylidenedioxy group formed together with R⁵;
R⁷ represents a hydrogen atom or a lower alkyl group; and
R⁸ represents a hydrogen atom, a hydroxyl group, or an amino group;
provided that the following cases are excluded:
(A) the case where R¹, R³, R⁴, and R⁷ are hydrogen atoms, R² and R⁸ are hydroxyl groups, and R⁵ and R⁶ are methoxy groups;
(B) the case where R¹, R³, R⁴, and R⁷ are hydrogen atoms, R², R⁵, and R⁶ are methoxy groups, and R⁸ is a hydroxyl group;
(C) the case where R¹, R³, R⁴, R⁷, and R⁸ are hydrogen atoms and R², R⁵, and R⁶ are methoxy groups;
(D) the case where R¹, R³, R⁴, and R⁷ are hydrogen atoms, R², R⁵, and R⁸ are hydroxyl groups, and R⁶ is a methoxy group;
(E) the case where R¹, R³, R⁴, and R⁷ are hydrogen atoms, R² and R⁶ are methoxy groups, and R⁵ and R⁸ are hydroxyl groups;
(F) the case where R¹, R³, R⁴, R⁷, and R⁸ are hydrogen atoms, R² and R⁶ are methoxy groups, and R⁵ is a hydroxyl group;
(G) the case where R¹, R², R⁵, and R⁶ are methoxy groups and R³, R⁴, R⁷, and R⁸ are hydrogen atoms;
(H) the case where R¹, R², R⁴, and R⁵ are methoxy groups and R³, R⁶, R⁷, and R⁸ are hydrogen atoms;
(I) the case where R¹, R², R⁵, and R⁶ are methoxy groups, R³, R⁴, and R⁷ are hydrogen atoms, and R⁸ is a hydroxyl group;
(J) the case where R¹ and R² are methoxy groups, R³, R⁴, R⁶, R⁷, and R⁸ are hydrogen atoms, and R⁵ is a hydroxyl group;
(K) the case where R¹, R², and R⁵ are methoxy groups, and R³, R⁴, R⁶, R⁷, and R⁸ are hydrogen atoms;
(L) the case where R¹, R², and R⁵ are methoxy groups, R³, R⁴, R⁶, and R⁷ are hydrogen atoms, and R⁸ is a hydroxyl group;
(M) the case where R¹, R², and R⁵ are methoxy groups, R³, R⁴, R⁶, and R⁸ are hydrogen atoms, and R⁷ is a methyl group;
(N) the case where R¹, R², and R⁵ are methoxy groups, R³, R⁴, and R⁶ are hydrogen atoms, R⁷ is a methyl group, and R⁸ is a hydroxyl group;
(O) the case where R¹, R², and R⁶ are methoxy groups, R³, R⁴, R⁷, and R⁸ are hydrogen atoms, and R⁵ is a hydroxyl group;
(P) the case where R¹, R², and R⁴ are methoxy groups, R³, R⁶, R⁷, and R⁸ are hydrogen atoms, and R⁵ is a hydroxyl group;
(Q) the case where R¹, R⁵, and R⁶ are methoxy groups, R² and R⁸ are hydroxyl groups, and R³, R⁴, and R⁷ are hydrogen atoms;
(R) the case where R¹ is an isopropyloxy group, R² and R⁵ are methoxy groups, and R³, R⁴, R⁶, R⁷ and R⁸ are hydrogen atoms;
(S) the case where R¹ and R⁵ are methoxy groups, R² is an isopropyloxy group, and R³, R⁴, R⁶, R⁷ and R⁸ are hydrogen atoms;
(T) the case where R¹ and R² are methoxy groups, R³, R⁴, R⁶, R⁷, and R⁸ are hydrogen atoms, and R⁵ is an isopropyloxy group;
(U) the case where R¹ and R⁵ are methoxy groups, R² is a hydroxyl group, and R³, R⁴, R⁶, R⁷, and R⁸ are hydrogen atoms;

(V) the case where $R^1$ and $R^2$ are methoxy groups, and $R^3$, $R^4$, $R^5$, $R^6$, $R^7$, and $R^8$ are hydrogen atoms;

(AE) the case where $R^1$, $R^3$, $R^4$, and $R^8$ are hydrogen atoms, $R^2$, $R^5$, and $R^6$ are methoxy groups, and $R^7$ is a methyl group;

(AH) the case where $R^1$, $R^2$, $R^4$, and $R^5$ are methoxy; $R^3$, $R^6$, and $R^7$ are hydrogen atoms; and $R^8$ is a hydroxyl group; and (AI) the case where $R^1$, $R^5$, and $R^6$ are methoxy, $R^2$ is a hydroxyl, and $R^3$, $R^4$, $R^7$, and $R^8$ are hydrogen.

5. The compound or salt of claim 4, wherein $R^8$ in the formula (2) is a hydrogen atom.

6. A compound or salt thereof, selected from the group consisting of:
- (12aS,13S)-5,6,7-trimethoxy-9,10,11,12,12a,13-hexahydro-9a-aza-cyclopenta[b]triphenylene-3,13-diol;
- (12aR,13R)-5,6,7-trimethoxy-9,10,11,12,12a,13-hexahydro-9a-aza-cyclopenta[b]triphenylene-3,13-diol;
- (12aS,13S)-9,10,11,12,12a,13-hexahydro-9a-aza-cyclopenta[b]triphenylene-3,13-diol;
- (12aS,13 S)-6-fluoro-9,10,11,12,12a,13-hexahydro-9a-aza-cyclopenta[b]triphenylene-3,13-diol;
- 6,7-dimethoxy-12a-methyl-9,10,11,12,12a,13-hexahydro-9a-aza-cyclopenta[b]triphenylene-3,13-diol;
- (S)-13-amino-6,7-dimethoxy-9,10,11,12,12a,13-hexahydro-9a-aza-cyclopenta[b]triphenylene-3-ol;
- (12aS,13S)-6,7-methylenedioxy-9,10,11,12,12a,13-hexahydro-9a-aza-cyclopenta[b]triphenylene-3,13-diol;
- (12aS,13S)-6,7-isopropylidenedioxy-9,10,11,12,12a,13-hexahydro-9a-aza-cyclopenta[b]triphenylene-3,13-diol;
- (12aS,13S)-6,7-diethoxy-9,10,11,12,12a,13-hexahydro-9a-aza-cyclopenta[b]triphenylene-3,13-diol;
- (S)-6,7-dimethoxy-9,10,11,12,12a,13-hexahydro-9a-aza-cyclopenta[b]triphenylene-3-ol;
- (R)-6,7-dimethoxy-9,10,11,12,12a,13-hexahydro-9a-aza-cyclopenta[b]triphenylene-3-ol;
- (S)-6,7-methylenedioxy-9,10,11,12,12a,13-hexahydro-9a-aza-cyclopenta[b]triphenylene-3-ol;
- (S)-6,7-diethoxy-9,10,11,12,12a,13-hexahydro-9a-aza-cyclopenta[b]triphenylene-3-ol;
- (12aS,13S)-2,3-dimethoxy-9,10,11,12,12a,13-hexahydro-9a-aza-cyclopenta[b]triphenylene-6,13-diol;
- (S)-2-chloro-6,7-dimethoxy-9,10,11,12,12a,13-hexahydro-9a-aza-cyclopenta[b]triphenylene-3-ol;
- (S)-4-chloro-6,7-dimethoxy-9,10,11,12,12a,13-hexahydro-9a-aza-cyclopenta[b]triphenylene-3-ol;
- (S)-2,4-dichloro-6,7-dimethoxy-9,10,11,12,12a,13-hexahydro-9a-aza-cyclopenta[b]triphenylene-3-ol;
- (S)-4-fluoro-6,7-dimethoxy-9,10,11,12,12a,13-hexahydro-9a-aza-cyclopenta[b]triphenylene-3-ol;
- (S)-2-fluoro-6,7-dimethoxy-9,10,11,12,12a,13-hexahydro-9a-aza-cyclopenta[b]triphenylene-3-ol; and
- (S)-6,7-dimethoxy-2,4-dimethyl-9,10,11,12,12a,13-hexahydro-9a-aza-cyclopenta[b]triphenylene-3-ol.

7. A medicine, comprising the compound or salt of claim 1 as an active ingredient.

8. An NFκB inhibitor, comprising the compound or salt of claim 1 as an active ingredient.

9. A therapeutic agent, comprising the compound or salt of claim 1 as an active ingredient,
wherein the agent is suitable for treating a disease associated with accelerated NFκB activity,
wherein said disease associated with accelerated NFκB activity is selected from the group consisting of metastatic cancer, rheumatoid arthritis, osteoarthritis, atopic dermatitis, bronchial asthma, psoriasis, inflammatory bowel disease, ischemic disease, vascular restenosis after percutaneous transluminal coronary angioplasty (PTCA), pulmonary fibrosis, diabetes, autoimmune disease, viral disease, Alzheimer's disease, ichorrhemia, and metabolic syndrome.

10. An anticancer agent, comprising the compound or salt of claim 1 as an active ingredient.

11. A therapeutic agent, comprising the compound or salt of claim 1 as an active ingredient, wherein the agent is suitable for treating a inflammatory disease selected from the group consisting of rheumatoid arthritis, osteoarthritis, atopic dermatitis, bronchial asthma, psoriasis, and inflammatory bowel disease.

12. A pharmaceutical composition, comprising:
the compound or salt of claim 1; and
a pharmaceutically acceptable carrier.

13. A medicine, comprising the compound or salt of claim 6 as an active ingredient.

14. An NFκB inhibitor, comprising the compound or salt of claim 6 as an active ingredient.

15. A therapeutic agent, comprising the compound or salt of claim 6 as an active ingredient,
wherein the agent is suitable for treating a disease associated with accelerated NFκB activity,
wherein said disease associated with accelerated NFκB activity is selected from the group consisting of metastatic cancer, rheumatoid arthritis, osteoarthritis, atopic dermatitis, bronchial asthma, psoriasis, inflammatory bowel disease, ischemic disease, vascular restenosis after percutaneous transluminal coronary angioplasty (PTCA), pulmonary fibrosis, diabetes, autoimmune disease, viral disease, Alzheimer's disease, ichorrhemia, and metabolic syndrome.

16. An anticancer agent, comprising the compound or salt of claim 6 as an active ingredient.

17. A therapeutic agent, comprising the compound or salt of claim 6 as an active ingredient, wherein the agent is suitable for treating a inflammatory disease selected from the group consisting of rheumatoid arthritis, osteoarthritis, atopic dermatitis, bronchial asthma, psoriasis, and inflammatory bowel disease.

18. A pharmaceutical composition, comprising:
the compound or salt of claim 6; and
a pharmaceutically acceptable carrier.

19. A method for treating a disease associated with accelerated NFκB activity, comprising administering to a subject in need thereof, an effective amount of the compound or salt of claim 1, wherein said disease associated with accelerated NFκB activity is selected from the group consisting of metastatic cancer, rheumatoid arthritis, osteoarthritis, atopic dermatitis, bronchial asthma, psoriasis, inflammatory bowel disease, ischemic disease, vascular restenosis after percutaneous transluminal coronary angioplasty (PTCA), pulmonary fibrosis, diabetes, autoimmune disease, viral disease, Alzheimer's disease, ichorrhemia, and metabolic syndrome.

20. A method for treating cancer, comprising administering to a subject in need thereof, an effective amount of the compound or salt of claim 1.

21. A method for treating inflammatory disease, comprising administering to a subject in need thereof, an effective amount of the compound or salt of claim 1, wherein said inflammatory disease is selected from the group consisting of rheumatoid arthritis, osteoarthritis, atopic dermatitis, bronchial asthma, psoriasis, and inflammatory bowel disease.

22. A method for treating a disease associated with accelerated NFκB activity, comprising administering to a subject in need thereof, an effective amount of the compound or salt of claim 6, wherein said disease associated with accelerated NFκB activity is selected from the group consisting of metastatic cancer, rheumatoid arthritis, osteoarthritis, atopic dermatitis, bronchial asthma, psoriasis, inflammatory bowel disease, ischemic disease, vascular restenosis after percutaneous transluminal coronary angioplasty (PTCA), pulmonary fibrosis, diabetes, autoimmune disease, viral disease, Alzheimer's disease, ichorrhemia, and metabolic syndrome.

23. A method for treating cancer, comprising administering to a subject in need thereof, an effective amount of the compound or salt of claim 6.

24. A method for treating inflammatory disease, comprising administering to a subject in need thereof, an effective amount of the compound or salt of claim 6, wherein said inflammatory disease is selected from the group consisting of rheumatoid arthritis, osteoarthritis, atopic dermatitis, bronchial asthma, psoriasis, and inflammatory bowel disease.

\* \* \* \* \*